(12) United States Patent
Pryce Lewis et al.

(10) Patent No.: US 7,820,201 B2
(45) Date of Patent: *Oct. 26, 2010

(54) SYSTEM FOR MANUFACTURING CONTROLLED RELEASE DOSAGE FORMS, SUCH AS ZERO-ORDER RELEASE PROFILE DOSAGE FORM MANUFACTURED BY THREE-DIMENSIONAL PRINTING

(75) Inventors: Wendy E. Pryce Lewis, Lexington, MA (US); Charles W. Rowe, Medford, MA (US); Michael J. Cima, Winchester, MA (US); Peter A. Materna, Metuchen, NJ (US)

(73) Assignee: Massachusetts Institute of Technology, Cambridge, MA (US)

( * ) Notice: Subject to any disclaimer, the term of this patent is extended or adjusted under 35 U.S.C. 154(b) by 453 days.

This patent is subject to a terminal disclaimer.

(21) Appl. No.: 11/876,153

(22) Filed: Oct. 22, 2007

(65) Prior Publication Data
US 2008/0220061 A1 Sep. 11, 2008

Related U.S. Application Data

(62) Division of application No. 10/284,039, filed on Oct. 29, 2002, now Pat. No. 7,300,668.

(60) Provisional application No. 60/540,664, filed on Oct. 29, 2001.

(51) Int. Cl.
*A61K 9/24* (2006.01)
*A61K 9/20* (2006.01)
*A61K 9/22* (2006.01)
*A61K 9/48* (2006.01)

(52) U.S. Cl. .................... 424/472; 424/451; 424/453; 424/468; 424/473

(58) Field of Classification Search .................. None
See application file for complete search history.

(56) References Cited

U.S. PATENT DOCUMENTS 3,184,386 A   5/1965   Stephenson (Continued)

FOREIGN PATENT DOCUMENTS

EP   0094123 A2   11/1983

(Continued)

OTHER PUBLICATIONS

Katstra, W.E. et al., "Oral dosage forms fabricated by Three Dimensional Printing," Journal of Controlled Release, 66:1-9, 2000.

(Continued)

*Primary Examiner*—S. Tran
(74) *Attorney, Agent, or Firm*—Rick Matos; Innovar, L.L.C.

(57) ABSTRACT

The present invention includes controlled release dosage forms and methods of designing and manufacturing dosage forms to obtain specific release profiles, for example, zero-order release profiles, escalating release profiles or decreasing release profiles. The dosage forms of the present invention can include spatial variation of API concentration in the dosage form and can include nested regions. Dosage forms according to the present invention may be manufactured by any appropriate method for obtaining the internal structure as disclosed herein for producing zero-order release profiles and increasing or decreasing release profiles. The invention further includes methods of manufacturing such dosage forms, such as by three-dimensional printing, possibly also including compression of the dosage form after three-dimensional printing. The invention further includes methods of designing such dosage forms. Release profiles from non-uniform distributions of API concentration may be predicted based on simple experiments with uniform-concentration dosage forms.

14 Claims, 27 Drawing Sheets

U.S. PATENT DOCUMENTS

| | | | |
|---|---|---|---|
| 4,289,795 A | 9/1981 | Bogentoft et al. | |
| 4,749,576 A | 6/1988 | Lee | |
| 4,892,742 A | 1/1990 | Shah | |
| 5,213,808 A | 5/1993 | Bar-Shalom et al. | |
| 6,514,530 B2 | 2/2003 | Skluzacek et al. | |
| 2002/0015728 A1* | 2/2002 | Payumo et al. | 424/451 |

FOREIGN PATENT DOCUMENTS

| | | |
|---|---|---|
| EP | 0111144 A1 | 6/1984 |
| EP | 0212747 A2 | 3/1987 |
| EP | 0230654 A2 | 8/1987 |
| GB | 793808 | 4/1958 |
| WO | WO 93/05769 | 4/1993 |
| WO | WO95/11007 | 4/1995 |
| WO | WO 97/32570 | 9/1997 |
| WO | WO 98/14168 | 4/1998 |
| WO | WO 98/19668 | 5/1998 |
| WO | WO 98/36739 | 8/1998 |
| WO | WO 01/37813 A2 | 5/2001 |
| WO | WO 01/87272 A2 | 11/2001 |

OTHER PUBLICATIONS

Rowe, C.W. et al., "Multimechanism oral dosage forms fabricated by three dimensional printing," Journal of Controlled Release, 66:11-17, 2000.

* cited by examiner

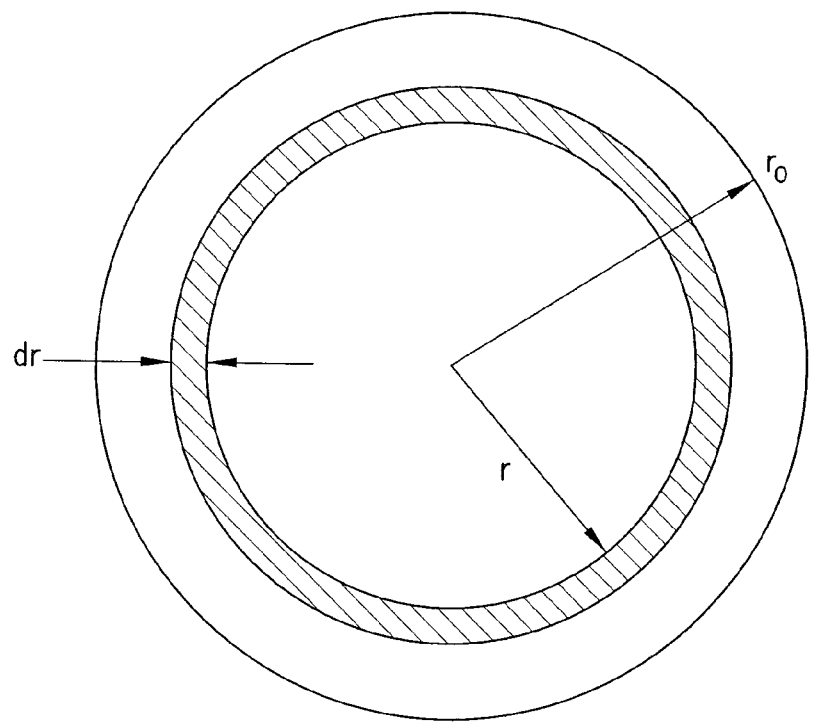
*FIG. 1*
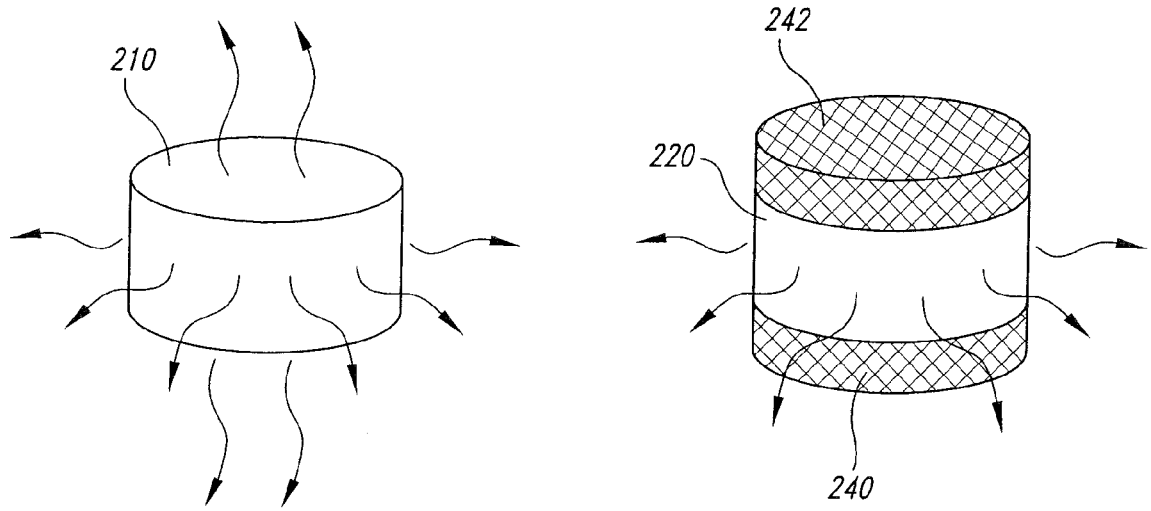
*FIG. 2A*   *FIG. 2B*

SYSTEM FOR MANUFACTURING CONTROLLED RELEASE DOSAGE FORMS, SUCH AS ZERO-ORDER RELEASE PROFILE DOSAGE FORM MANUFACTURED BY THREE-DIMENSIONAL PRINTING

CROSS-REFERENCE TO EARLIER FILED APPLICATIONS

This application is a division of and claims the benefit of priority of U.S. Ser. No. 10/284,039 filed Oct. 29, 2002, which claims the benefit of priority of Provisional application No. 60/540,664 filed Oct. 29, 2001, the entire disclosures of which are hereby incorporated by reference.

FIELD OF THE INVENTION

This invention relates to controlled release dosage forms and to methods of designing such dosage forms and methods of manufacturing such dosage forms, and more particularly a controlled release dosage form manufactured by three-dimensional printing.

DESCRIPTION OF THE RELATED ART

There are at least two physical mechanisms that can be important in controlled release drug delivery: erosion and diffusion.

Diffusion involves the passage of interior contents of a dosage form out through the surface of the dosage form while the surface is not removed, or, more generally, it involves motion of contents within the dosage form. It is governed by concentration gradients and diffusivities.

As an example of diffusion-controlled dosage forms, oral dosage forms have been fabricated conventionally such as by tablet pressing, and then have been coated with a release barrier coating. The coating has been permeable to water and gastric fluids, while not being soluble in these liquids. Ingestion of the dosage form by the patient has resulted in water penetrating the film and beginning dissolution of the Active Pharmaceutical Ingredient (API) inside the tablet. The dissolved form of the API has then been able to diffuse through the film material. The natural release profile of a dosage form governed by diffusion is that the cumulative amount of API released is proportional to the square root of time since initiation of release, i.e., $Q=k*t^{0.5}$. The release rate of such a dosage form is the derivative of this function, namely: $r=k'*t^{-0.5}$, which is a release rate that decreases with time.

The other release mechanism, erosion, involves the physical removal of material from the surface of a dosage form, such as by its dissolution in bodily fluids or by its degradation by bodily fluids. Release of API occurs because of this removal of material from the dosage form. Erosion-controlled dosage forms, when made with uniform composition throughout, have had a release rate that is proportional to the instantaneous surface area of the dosage form. Therefore, as the dosage form has become smaller, the release rate has also decreased.

Another controlled release dosage form has been a device known as an osmotic pump. Such devices have been constructed from a core containing the API, a selectively impermeable coating with a defined exit orifice, and a hygroscopic salt or other material that swells when wet and squeezes the API out through the orifice. This type of dosage form has suffered from the need for an exact size orifice and the need for the film to be defect free other than at the defined exit orifice.

An erodible dosage form made by three-dimensional printing, which has included geometric design and compositional variation in the interior of the dosage form, has been described in U.S. Pat. No. 6,280,771. The dosage form of that patent has provided bursts or phases of API release but did not teach a method or dosage form for providing zero-order release of API.

Various APIs work best with specific release profiles that are optimum for that particular API. One commonly required release profile is zero-order release, which is a release rate of API that is constant with respect to time. Such a release profile is desirable in cases where the API must be delivered to the patient's body at a constant rate in order to maintain constant or nearly constant concentration of API in the blood to maintain therapeutic effectiveness. This is particularly useful for APIs with short half-lives in the patient's bloodstream. A zero-order controlled release dosage form can maintain constant concentration of API in a patient's bloodstream with fewer doses administered to the patient than would be necessary with conventional burst release dosage forms, and this could improve patient compliance.

Other APIs may require an escalating release profile, wherein the release rate starts off relatively low and then increases over the course of the release. Escalating release may be desirable for APIs where the patient develops a tolerance over the course of medication. An example of this type of API is nitrates for treating angina. Another type of API for which escalating release would be helpful is H-2 inhibitors, because they are absorbed by the body more easily in the upper portion of the gastrointestinal tract than in the lower portion.

Other APIs may require a decreasing release profile, wherein the release rate starts off relatively high and then decreases over the course of the release. Decreasing release may be appropriate for APIs where an initial high dose is desirable followed by slower release. An example of this type of treatment would be APIs for arthritis, where initially a high blood level of API is needed to eliminate morning pain and stiffness, followed by lower levels to keep the patient pain-free during the day.

True zero-order release has been difficult to obtain with traditional dosage forms. For erosion-based dosage forms, the surface area has become smaller as time progressed, and thus the API release rate has become slower as the release progressed. For diffusion-based dosage forms, the surface area has been essentially constant, but the API inside the dosage form has not been available in infinite supply, and therefore the driving force for diffusion of API out of the dosage form has decreased as the release progressed because the concentration of API within the dosage form decreased. For both types of processes, the usual tendency has been for release rate to decrease as time progressed.

Researchers have claimed zero-order release from other geometries and dosage forms. Langer (*Annals of Biomedical Engineering* (1995) 23 pp. 101-111) has achieved zero-order release in surface-erodible thin slabs of uniform API distribution. Kerč (*Proceed. Int'l Symp. Control. Rel. Bioact., Mater.*, Controlled Release Society, Inc., (1998) 25, p 912-913) has approximated zero-order release using a three phase dosage form in which the different phases degraded at different rates. A device has recently been invented by Odidi (OROS™ technology, Alza Corp. http://www.alza.com), which features an osmotic "push-pull" mechanism as a means to achieve zero-order release. Yet another method of delivering an API in an approximately zero-order release has been a method wherein the dosage form uses a swellable cylindrical central core covered with insoluble caps that cover the axial faces of the tablet, but not the circumference. When ingested by the patient, the core of the tablet has swelled over time, maintaining a constant tablet surface area for release, leading to zero-order release.

In general, all of these designs attempting to produce zero-order release have both with respect to performance as well as from manufacturing complexity. In addition, some prior art solutions are limited to a relatively small dose of API, because of the amount of space occupied by other components of the dosage form. Many of the dosage forms have also been limited as far as not being able to provide an arbitrary release profile, but rather have been essentially designed around one very specific release profile with little ability to adjust that release profile.

Accordingly, it would be desirable to provide dosage forms, such as erosion-based dosage forms, capable of providing zero-order release, and also, in general, capable of providing any desired release profile such as escalating release or decreasing release. It would also be desirable to provide associated methods of manufacture. It would also be desirable to provide a generalized methodology for designing such dosage forms that allows the desired release profile to be achieved with a minimum amount of trial-and-error iteration of designs of dosage forms.

BRIEF SUMMARY OF THE INVENTION

The present invention includes dosage forms which release API in a zero-order release profile, or in some other desired release profile such as escalating release or decreasing release, or in general, any desired release profile. The dosage forms of the present invention can include spatial variation of API concentration in the dosage form and can include nested regions. The invention further includes methods of manufacturing such dosage forms, such as by three-dimensional printing, possibly also including compression of the dosage form after three-dimensional printing. The invention further includes methods of designing such dosage forms. Release profiles from non-uniform distributions of API concentration may be predicted based on simple experiments with uniform-concentration dosage forms.

BRIEF DESCRIPTION OF THE SEVERAL VIEWS OF THE DRAWINGS

The invention is illustrated in the following figures, in which:

FIG. 1 is a schematic illustration of geometric terms used herein.

FIGS. 2A and 2B illustrate dosage forms exposed to a surrounding liquid in accordance with principles of the present invention.

DETAILED DESCRIPTION OF THE INVENTION

Figure 3A:
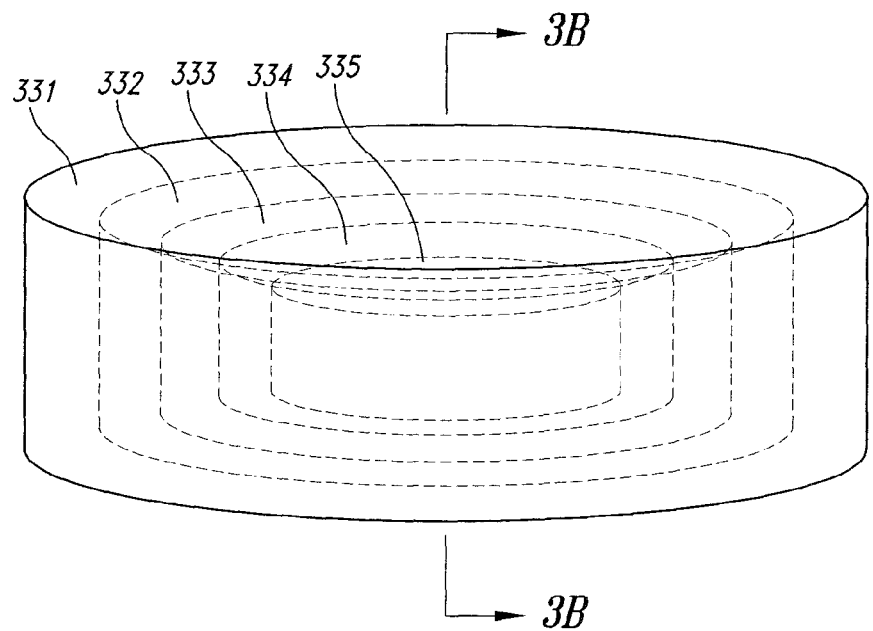
FIGS. 3A and 3B illustrate a dosage form of the present invention having nested internal regions and having a cylindrical geometric shape with release from all surfaces in accordance with principles of the present invention.

The present invention relates to controlled release dosage forms and methods of designing and manufacturing dosage forms to obtain specific release profiles, for example, zero-order release profiles. Dosage forms according to the present invention may be manufactured by any appropriate method for obtaining the internal structure as disclosed herein for producing zero-order release profiles and increasing or decreasing release profiles. One example of a suitable manufacturing process is three-dimensional printing as is known in the art and further defined herein.

Designing Release Rates

The release of Active Pharmaceutical Ingredient (API) from many dosage forms can be described by the assumption that the instantaneous release rate of API is related to the instantaneous external surface area of the dosage form and to the concentration of API at the surface of the dosage form. These assumptions apply most specifically to erodible dosage forms, in which the dosage form loses mass and becomes smaller as time progresses, but they could also apply to dosage forms operating under other release mechanisms or combination(s) of release mechanisms that at least approximately satisfy these assumptions. For example, the overall kinetic process could be purely erosion or could include dissolution, swelling, chemical reaction of a host polymer, etc., or a combination of more than one of these individual phenomena ultimately leading to the surface degradation of the dosage form material, as long as the overall process can be described by the above assumptions. Analytical relationships describing the kinetics of API release from infinite cylinders under these assumptions have been derived by Hopfenberg (*American Chemical Society Series* 33 (eds. D R Paul, F W Harris, ACS, E 26-32). In Hopfenberg's analysis, the overall kinetic process is characterized using one rate constant, $k_o$.

The analysis considers the cross-section of a cylinder perpendicular to the cylinder axis. The cylinder is assumed to undergo surface erosion or degradation, with the surface receding according to $$\frac{dr}{dt} = -\frac{k_o}{C_o} \quad \text{(Eq. 1)}$$

For this situation, the normalized amount of API or additive released from the dosage form as a function of time is $$\frac{Q}{Q_T} = 1 - \left(1 - \frac{k_o t}{C_o r_o}\right)^2 \quad \text{(Eq. 2)}$$

In this equation $k_o$ is the rate constant, which may be measured in mg/hr-cm², $C_o$ is the initial concentration of API within the dosage form (assumed to be uniform and constant), which may be measured in mg/cc, and $r_0$ is the initial radius of the cylindrical dosage form, which may be measured in cm. In the rate constant and in the concentration, the units "mg" refer to amount of API. Any other consistent set of units can also be used. Q is the cumulative amount of API or similar additive released from initiation of release up until a time t. $Q_T$ is the total amount of API or similar additive available to be released from the dosage form. The time t is the time measured from initiation of exposure to liquid, and is allowed to have values between 0 and the time it takes for the dosage form to completely disappear (which for the one-dimensional cylindrical case is defined as radius equaling zero).

This model, however, is only one-dimensional, describing only radial release of API, and does not consider the possible release of API from the top or bottom surfaces of a cylindrical dosage form. Accordingly, Katzhendler et al. (*J. Pharm. Sci.* (1997) 86(1), 110-115) have developed a more detailed two-dimensional model to describe API release from erodible or degradable dosage forms which are circular cylinders undergoing surface erosion or degradation on all of their surfaces. The model starts from the Hopfenberg equation (6.1) and then modifies it to account for both radial and axial directions of release. Using this model, Katzhendler was able to successfully predict the release of amoxicillin from dosage forms consisting of two different viscosity grades of HPMC.

In the Katzhendler model, the kinetics of API release from erodible cylindrical dosage forms are analyzed using two coordinates: r, radial, and h, axial. In the radial direction, it is assumed that the erosion front, whose location is represented by the coordinate r, moves radially inward perpendicular to the local surface with a constant velocity. This velocity is equal to a radial erosion constant, $k_r$, divided by a dosage form's API concentration, $C_o$ (assumed to be uniform and constant).

$$\frac{dr}{dt} = -\frac{k_r}{C_o} \quad \text{(Eq. 3)}$$

A similar equation is established for the axial coordinate, h, using axial erosion constant, $k_h$, and because the erosion occurs from two surfaces, a factor of 2 is included:

$$\frac{dh}{dt} = -2\frac{k_h}{C_o} \qquad \text{(Eq. 4)}$$

Integration with respect to time, and substitution of initial conditions, yields the following relationships for r and h:

$$r(t) = r_o - \frac{k_r t}{C_o} \qquad \text{(Eq. 5)}$$

$$h(t) = h_o - 2\frac{k_h t}{C_o} \qquad \text{(Eq. 6)}$$

The normalized amount of API released from the dosage form over time, $Q/Q_T$, is given by:

$$\frac{Q}{Q_T} = 1 - \frac{\pi r^2 h}{\pi r_o^2 h_o} \qquad \text{(Eq. 7)}$$

By substituting equations (5) and (6) into the above expression (Eq. 7), a new expression, similar to Hopfenberg's equation (Eq. 2) is obtained:

$$\frac{Q}{Q_T} = 1 - \left(1 - \frac{k_r t}{C_o r_o}\right)^2 \left(1 - \frac{2k_h t}{C_o h_o}\right) \qquad \text{(Eq. 8)}$$

Equation 8 describes the API release from a flat-ended cylindrical dosage form eroding at all of its surfaces. If it is further assumed that the erosion rate constants in the radial and vertical directions are similar, i.e., $k_r \approx k_h \approx k_o$, then Equation 8 can be further simplified:

$$\frac{Q}{Q_T} = 1 - \left(1 - \frac{k_o t}{C_o r_o}\right)^2 \left(1 - \frac{2k_o t}{C_o h_o}\right) \qquad \text{(Eq. 9)}$$

In the use of this equation, t is intended to have values ranging from zero at the start of exposure to liquid, to a final time which is determined by whichever dimension (radial or axial) of the dosage form reaches zero first.

A frequent goal in controlled-release dosing is to produce a zero-order release, i.e., a constant release rate. In order to gain some insight into how to achieve this situation, it is convenient to consider a cylindrical geometry that releases in the radial direction only, since this is one-dimensional and hence easily tractable analytically. (Spherical shells would also be one-dimensional but would involve greater practical difficulties in manufacturing and especially in compressing the shapes.) The Hopfenberg model can be used to derive what would be the ideal distribution of API concentration as a function of radius in order to achieve a constant release rate as a function of time. It is assumed that the radial surface erosion/degradation rate of such a cylinder, in units of length/ time, is independent of the radius at which erosion/degradation is occurring, and also is the same everywhere along the length of the cylinder. For the case of erosion from the perimeter of a circular cylinder, the incremental volume eroded is illustrated in FIG. 1.

It can be seen that the incremental volume of material eroded (per unit length) is 2*pi*r*dr, and the API released is C*2*pi*r*dr. A zero-order release system, or a system with constant API delivery rate, is obtained when the API distribution complements the volumetric non-uniformity of the eroding layers. The radial increment dr is assumed constant for constant time increments. Thus, the criterion for achieving constant release rate is that C, the local concentration of API, should be proportional to 1/r. The API release rate will be a constant if and only if the initial API distribution, C(r), has the form $$C(r) \sim \frac{1}{r} \qquad \text{(Eq. 10)}$$

where r is the radial coordinate of a particular location.

For a flat-ended cylindrical dosage form that releases API from all of its surfaces, which is a two-dimensional situation, there is not such a simple analytical prediction available. A similar derivation may be done for a spherical dosage form, and it indicates that for a sphere the ideal concentration dependence predicted to give zero-order release is a concentration whose dependence on radius is of the form $$C(r) \propto \frac{1}{r^2} \qquad \text{(Eq. 11)}$$

Among the useful dosage form shapes are cylindrical shapes. In accordance with these concepts, cylindrical dosage forms of the present invention, for zero-order or other release profile, may be designed with either of two geometries describing their release, i.e., either radial-release or 3-D release. For each case, FIGS. 2A and 2B illustrate which surfaces of the dosage form are exposed to bodily fluids or dissolution fluids. 3-D release is the type of release experienced if no special design steps are taken to prevent release in specific places, i.e., if all of the exposed surfaces of the dosage form 210 were exposed to bodily fluid or dissolution fluid and hence were able to release API.

On the other hand, radial-release may be desired, and there are two ways of achieving it. One way is to make the cylinder so much longer than its radius that the curved surface area is much larger than the end surface area. Cylindrical shapes may be described by an aspect ratio, which is a ratio of length to radius, and cylindrical dosage forms of the present invention may be designed with any aspect ratio. However, cylinders with long length-to-radius ratio may not be convenient for ease of swallowing (in the case of oral dosage forms) or for other practical reasons.

Accordingly, another way of achieving radial release is illustrated in FIG. 2B and includes a dosage form of shape such as cylindrical may be fabricated having an API-releasing portion 220 which is exposed to bodily fluid or dissolution fluid and also having end caps 240 and 242, attached to API-releasing portion 220, which are resistant to releasing API or which are substantially slower to erode or degrade than are the API-releasing portion 220 of the dosage form. This leaves the curved side surfaces exposed to be eroded or degraded, while preventing contact of bodily fluid or dissolution fluid with any end surfaces of the API-releasing portion 220 of the dosage form. Other shapes of dosage forms are also possible in accordance with the present invention, including rectangular prismatic and spherical, as discussed elsewhere herein.

Internal Design of Dosage Forms

Further in accordance with these concepts, dosage forms of the present invention may be designed to have multiple internal regions, with each region having its own respective API concentration. In such a dosage form having multiple internal regions, each respective region may have a regional API concentration that is different from the API concentration of the region(s) adjacent to it. The API concentration of individual regions may in general be non-zero except that the innermost region of the dosage form may have a finite concentration of API or may have zero concentration of API as described elsewhere herein, and it is also possible for some (not all) of the non-innermost regions to have zero API concentration if desired. It is possible that the dosage form may be designed with in general any relative placement or topology of regions, such as having nested regions or non-nested regions or both. One of the last Examples in the Examples section describes a not-completely-nested dosage form design, while many other Examples herein describe nested dosage form designs.

The dosage form may be designed such that the regions release in chronological succession, thereby defining a release profile. The release of regions in chronological succession may be attained by a design such that regions intended for later release are blocked from access to bodily fluids or dissolution fluids by a release-preventing region at least some of which eventually disappears due to erosion/degradation. This can result in a design having regions that are successively nested within each other. Nesting can be the situation where a given region has all of its surfaces in contact with an earlier-dissolving region. Nesting can also be accomplished if a region has some of its surfaces in contact with an earlier-dissolving region and the rest of its surfaces in contact with a region that is substantially non-dissolving (approximately insoluble or extremely slow to dissolve). Both situations are illustrated later herein.

Further in accordance with this concept of release in chronological succession from various regions, it can be understood that the regions may be arranged, dimensioned and manufactured so that a particular region becomes extinct (due to erosion, degradation etc.) at approximately the same time everywhere around the dosage form.

In this situation, the dosage form may be designed such that the multiple internal regions with their respective API concentrations form a stepwise approximation of a continuous distribution of API such as may be suggested by an analytical prediction.

Figure 3B:
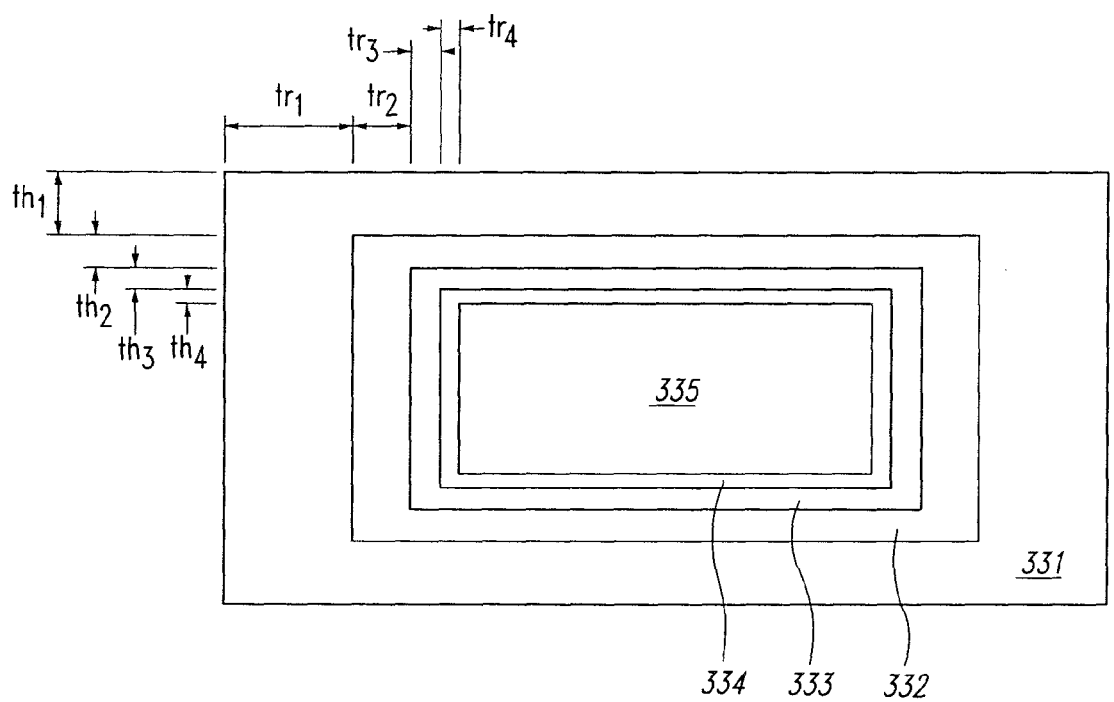

The successively nested design of the present invention is further illustrated using the cylindrical geometry with 3-D release. FIG. 3 illustrates a dosage form of the present invention that has a cylindrical shape with flat ends and is exposed to surrounding liquid on all of its surfaces and is able to release API from all of its surfaces. FIG. 3 illustrates concentrically nested shapes, alternatively, the shapes may be eccentric or some combination thereof. The release dosage form of FIG. 3 may comprise a plurality of nested regions, each region being completely surrounded in all directions by the region immediately outside it. There may be an innermost region, and, at least one additional region, with each region except the innermost region being configured so as to surround the innermost region and any other region located interiorly of the region. Each region may have its own respective regional concentration of API which is different from the API concentration in adjacent region(s) and which may in general be non-zero except that, as explained elsewhere herein, the innermost region may be designed to have either a finite concentration of API or zero concentration of API and some of the non-innermost regions could also if desired have zero concentration.

FIG. 3 shows, for sake of illustration, five nested regions. The innermost region 335 is surrounded in all directions by a next region 334, which is in turn surrounded by another region 333, which is in turn surrounded by yet another region 332, which is in turn surrounded by the outermost region 331. In the cylindrical geometry illustrated in FIG. 3, the innermost region 335 has solid dimensions in the radial and axial dimensions and then all of the other regions have an axial-direction wall thickness ($th_1$, $th_2$, $th_3$, $th_4$) and a radial wall thickness ($tr_1$, $tr_2$, $tr_3$, $tr_4$).

This dosage form, when immersed in a bodily fluid or dissolution fluid, may have a rate at which the release-determining feature, of the dosage form recedes in the radial direction, and a rate at which the release-determining feature, of the dosage form recedes in the axial direction. (Example 1 explains that the rate of recession may most appropriately refer to the rate of recession at which a release-determining feature of the dosage form, such as the solid/hydration front, recedes in a particular direction. In a relatively simple material system, the release-determining feature might simply be the surface.)

In the design of such a dosage form it may be desired that a given region should become extinct and a next region should begin to contact the surrounding liquid at a time which is, as nearly as possible, simultaneous everywhere around the surface of the dosage form. Accordingly, the dosage form may be designed so that in both the radial direction and the axial direction, the thickness of the region in a given direction, divided by the rate of surface recession in that direction, has a value which is equal to the corresponding value for any other direction. In many cases the rate of surface recession is considered to be identical for all directions. If this is the case, it implies that the dosage form may be designed such that the wall thickness of an individual region may be the same in all directions, for example, in a cylindrical geometry, the radial wall thickness equaling the axial wall thickness. The same considerations also apply to other shapes and other numbers of dimensions.

Figure 25:
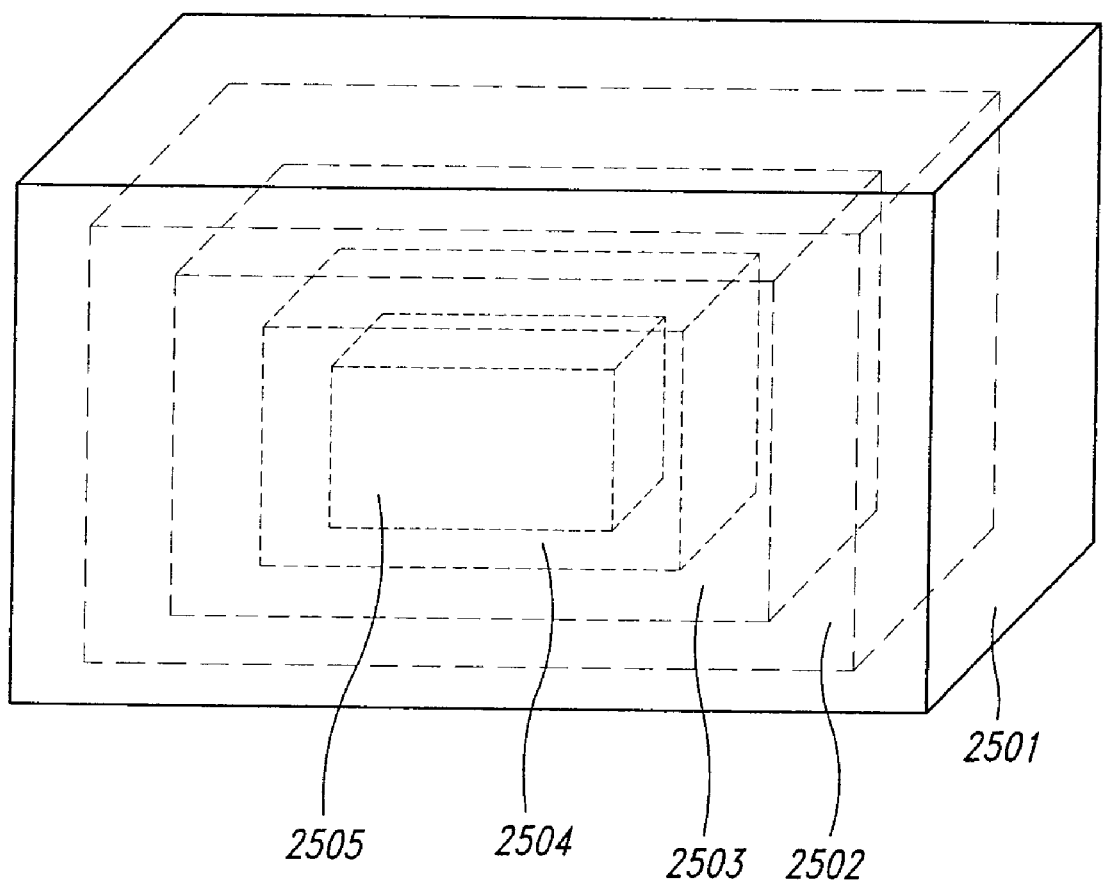
FIG. 25 illustrates a schematic of a cylindrical dosage form having five nested regions that is 3-D release, i.e., release from all surfaces in accordance with principles of the present invention.

In addition to the cylindrical design of dosage form illustrated in FIG. 3, a dosage form could also be manufactured in the form of a rectangular prism. If such a dosage form were constructed for 3-D release, i.e., release from all surfaces of the dosage form, each rectangular prismatic region may be surrounded in all directions by another rectangular prismatic region outside it. This is illustrated in FIG. 25 for the case where there are five nested regions. In this case the dosage form and each individual region within it would have three individual orthogonal dimensions and each individual region, except for the innermost region, would have a wall thickness for each of those directions. In that case, it may be desirable to satisfy the condition in all directions that the local wall thickness divided by the local rate of surface recession have a value which is the same for all directions. In the simple case of uniform rate of surface recession, this implies uniform wall thicknesses in all three of those directions.

Figure 4:
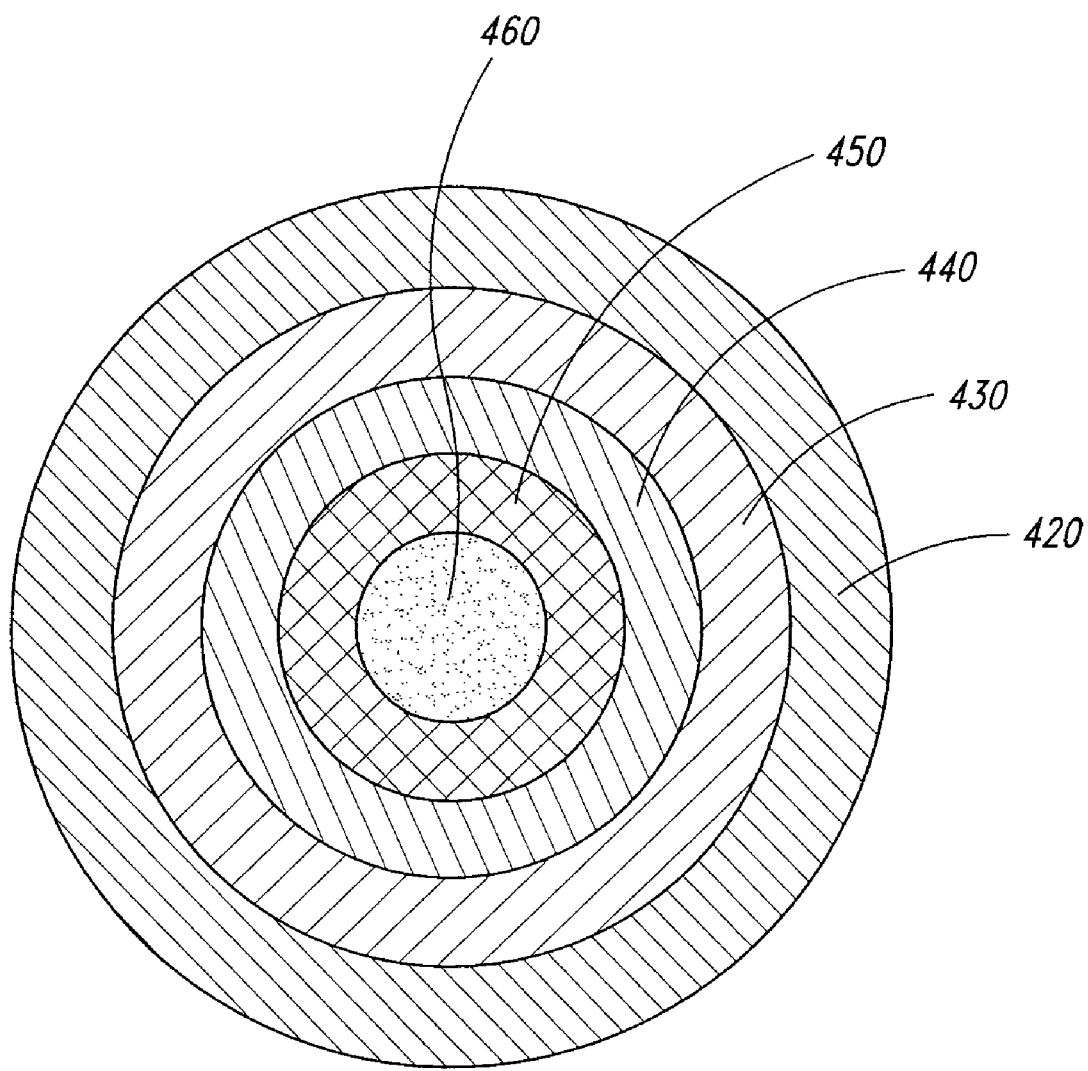
FIG. 4 illustrates a cross-section of a dosage form having a spherical geometric shape with nested regions in accordance with principles of the present invention.

A dosage form could also be in the shape of a sphere, as illustrated cross-sectionally in FIG. 4. FIG. 4 illustrates concentric spheres of decreasing size nested within one another. In this embodiment, the largest sphere 420 has four smaller spheres therein, namely, 430, 440, 450 and 460. FIG. 4 illustrated spheres of decreasing size such that the distance between boundary layers is approximately equal. Alternatively, the boundary layer thickness may be thinner, thicker or variable. Alternatively, the dosage form shape could be an ellipsoid, in which case the nested regions would be spherical shells (spherical annuli) or ellipsoidal shells.

In a dosage form manufactured by three-dimensional printing, as described elsewhere herein, there would be layers within the dosage form at least during some stages of three-dimensional printing, corresponding to the layers in which powder is deposited during 3DP, although these layers may or may not be detectable in the finished product. In the direction of build, i.e., the direction in which layers are added, the wall thickness of an individual region is constrained to be either the thickness of a 3DP layer or an integer multiple of the thickness of a 3DP layer, because a 3DP layer can have only one composition across its layer thickness in the build direction.

Thus, the wall thickness corresponding to the 3DP build direction, which for the illustrated orientation is the axial direction of the cylindrical dosage form or one of the three mutually orthogonal principal directions of a rectangular prismatic dosage form, may be constrained to be either the 3DP layer thickness or an integer multiple of the 3DP layer thickness. Accordingly, the other wall thickness(es) of the dosage form may also be constrained to be the same dimension as the wall thickness in the build direction, which is either the 3DP layer thickness or an integer multiple of the 3DP layer thickness. Although in three-dimensional printing it is typical to use equal 3DP layer thicknesses throughout a print job, this is not absolutely necessary and it would be possible to use unequal layer thicknesses, if desired, in different layers of a 3DP print job, so as to allow more freedom in the dimensioning of individual regions of the dosage form. The use of unequal layer thicknesses would in turn require other adjustments in printing parameters to correspond to variations in the thickness of individual layers.

Alternatively, it is also possible that the various wall thicknesses of regions having two-wall thickness might not be chosen with a view toward simultaneous extinction of all surfaces of a region. For example, it is possible that a dosage form may be arranged, dimensioned and manufactured such that a given region becomes extinct at some of its exposed surfaces at a certain time and becomes extinct at other of its exposed surfaces at a different time. A dosage form may be deliberately designed with unequal wall thicknesses in different directions of any given region. Cylindrical dosage forms have two different wall thicknesses that could be independently chosen.

Regions of a cylindrical dosage form may be dimensioned such that the axial surfaces of a region might extinguish themselves and result in the erosion/degradation front entering the next region in the axial direction, while the radial surfaces of a region are still releasing API from that region. The opposite order (radial surfaces extinguishing before axial) is similarly possible, of course. Rectangular prismatic dosage forms have three wall thicknesses that could be independently chosen, to similarly give changeover at different times. Such a design would provide more changeover points in the release profile than simply the number of regions, and therefore might provide a smoother release profile than would be predicted from a dosage form whose discrete regions extinguish simultaneously all around a given region. This could be useful in particular for dosage forms having fairly small numbers of regions. The fact that in certain directions a wall thickness might have to be an integer number of 3DP layers means that some wall thicknesses might have to be adjusted from a preferred dimension and for that reason might not be able to be designed to extinguish simultaneously with some other wall thickness.

Another possibility is to design the dosage form according to a criterion relating surface areas of individual regions and the regional API concentrations of individual regions, as described in one of the Examples. This might determine the thickness of certain walls and might not allow equality of wall thicknesses.

Still another possibility is a dosage form whose regions have wall thicknesses which vary in a continuous manner and which therefore become extinct gradually, such as the extinction location moving gradually around a region within the dosage form. This would provide an even greater degree of smoothing of a release profile from a dosage form that might be manufactured having discrete regions. A way to achieve a wall thickness with a continuous variation would be with a region that is annular, defined by two boundaries which are circular but which are positioned eccentrically with respect to each other. Similar continuous variation of wall thickness could also be achieved with other shapes as well.

The dosage forms just described released from all of their surfaces. A dosage form of the present invention may also be constructed so as to release from less than all of its surfaces. For example, a cylindrical dosage form may be constrained to release essentially only in the radial direction, which makes modeling and analysis essentially one-dimensional and hence more tractable.

Figure 5:
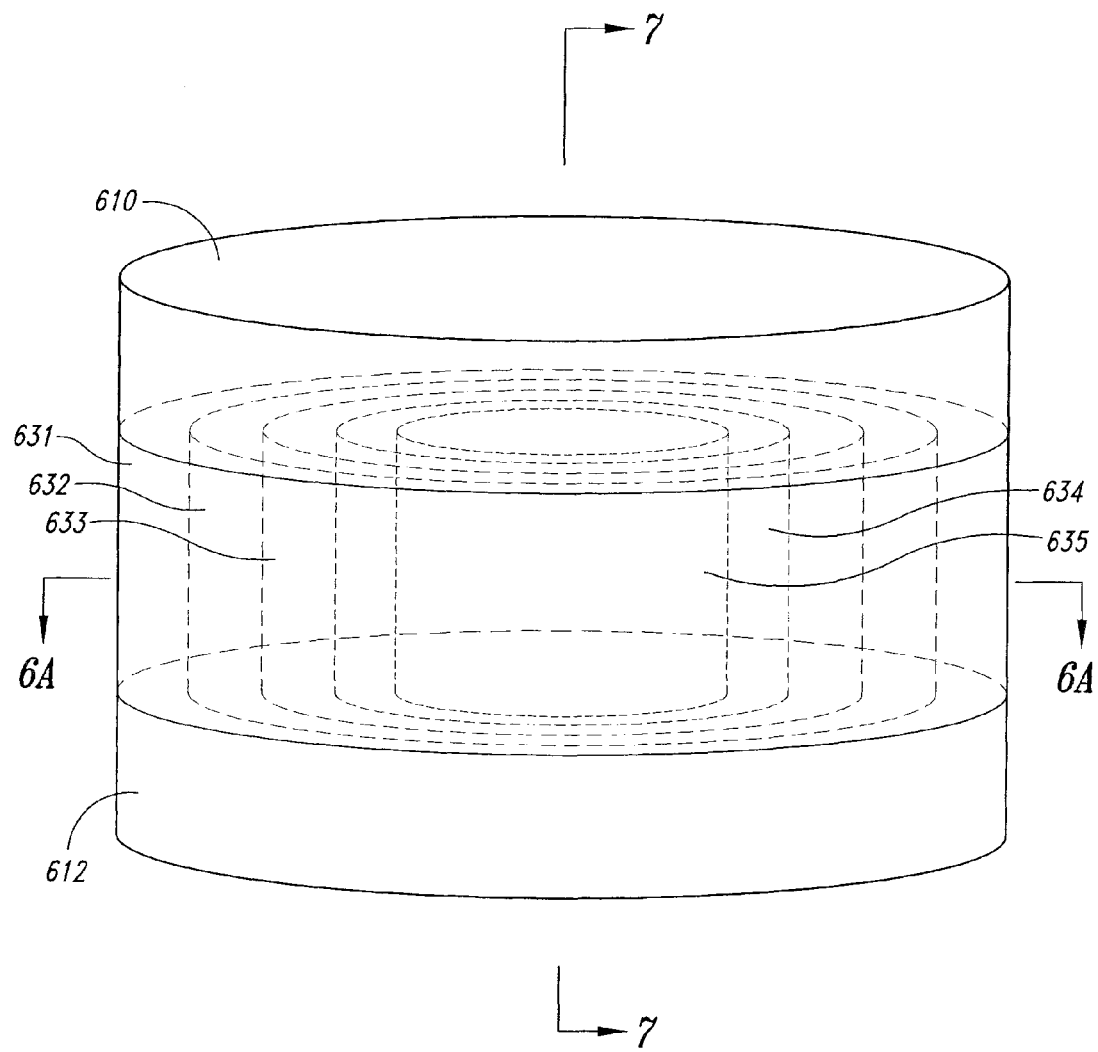
FIG. 5 illustrates a dosage form of the present invention having nested internal regions and having a cylindrical geometric shape with release only from the curved surfaces of the cylinder in accordance with principles of the present invention.
Figure 6A:
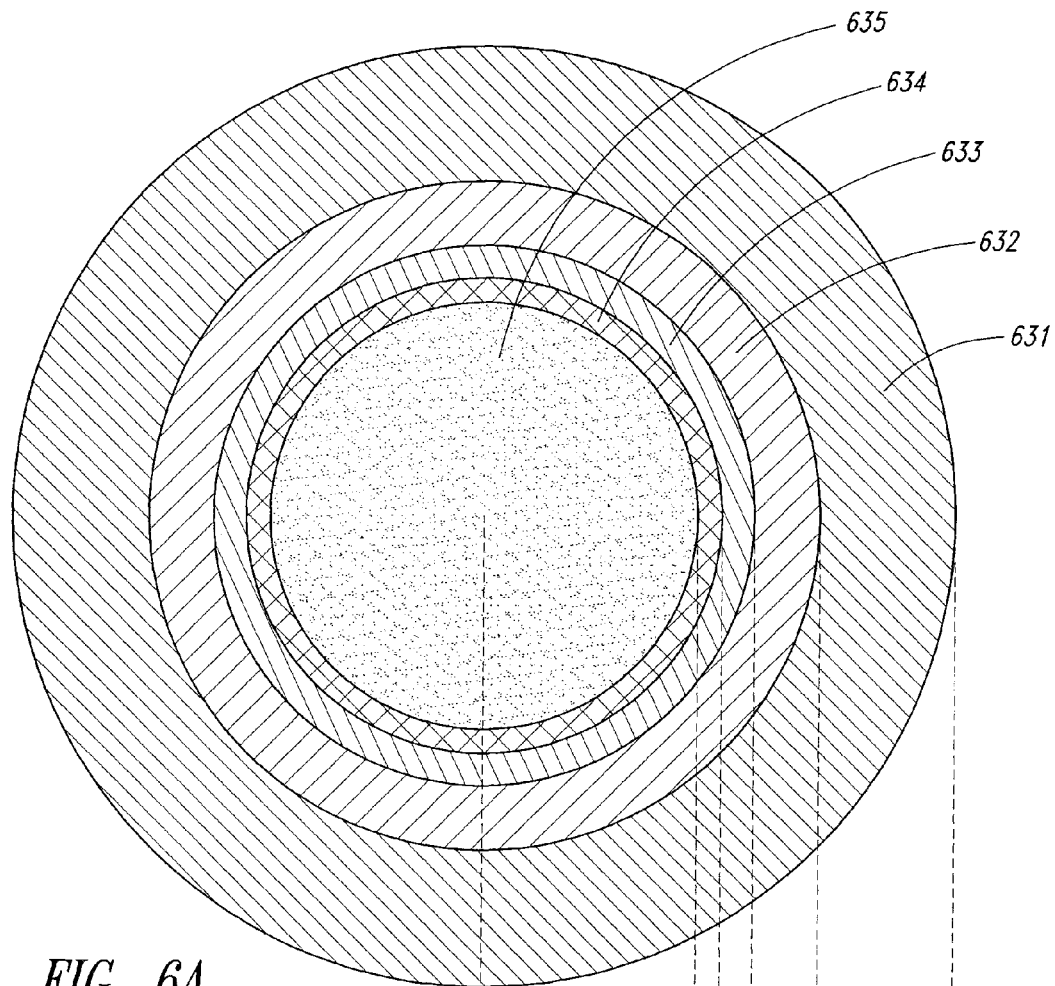
FIG. 6A illustrates a cross-section of FIG. 5 along line 6A-6A.
Figure 6B:
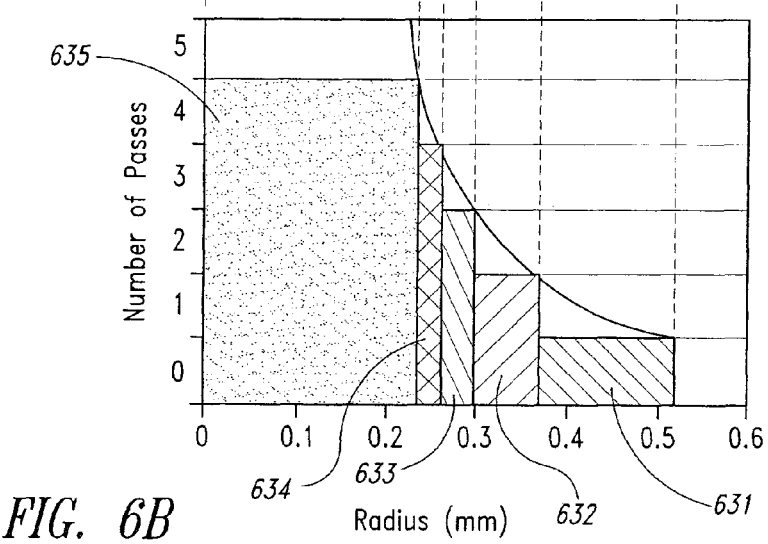
FIG. 6B illustrates a graph of the radius of each internal region of the dosage form of FIG. 5.

Such a dosage form is shown in FIG. 5 and in cross-section in FIGS. 6A and 6B. In order to prevent release of API from the end surfaces, such a dosage form 600 may include end caps 610 and 612. Between the two end caps 610 and 612 may be a central portion 620. End caps 610 and 612 may be such that, upon exposure to a liquid, they may be non-erodible or least substantially less erodible than the regions in the central portion 620 of the dosage form. End caps 610 and 612 may be constructed so as to be free of API. At least some of the central portion 620 may contain API.

In FIGS. 5 and 6, the number of regions illustrated in the central portion 620 of the dosage form is five. The central portion 620 of the dosage form may comprise an innermost region 635 extending between the two end caps 610 and 612, surrounded by another region 634 which also extends between the two end caps 610 and 612 and surrounding the first region 635, and subsequent regions 633, 632 and 631 continuing in a similar nesting pattern. Each region may have its own respective concentration of API that is different from the API concentration of whatever regions are adjacent to the region. The API concentration of each region may in general be non-zero except that the innermost region either may contain a finite concentration of API or may contain substantially zero concentration of API (or of at least one API), and it is also possible for some of the other regions to have zero concentration of API if desired.

In any of these geometries, the API concentrations of the respective regions may be chosen so as to give a desired release profile as the regions successively are exposed and release their contents. For example, desired release profiles may be zero-order, or escalating, or decreasing. For example, the regional concentrations may form a pattern which is monotically or stepwise monotonically increasing as one goes from the outside of the dosage form to the most central or last-to-erode portion of the dosage form (again, with the realization that the innermost region in particular may either contain API or be free of API).

Figure 7:
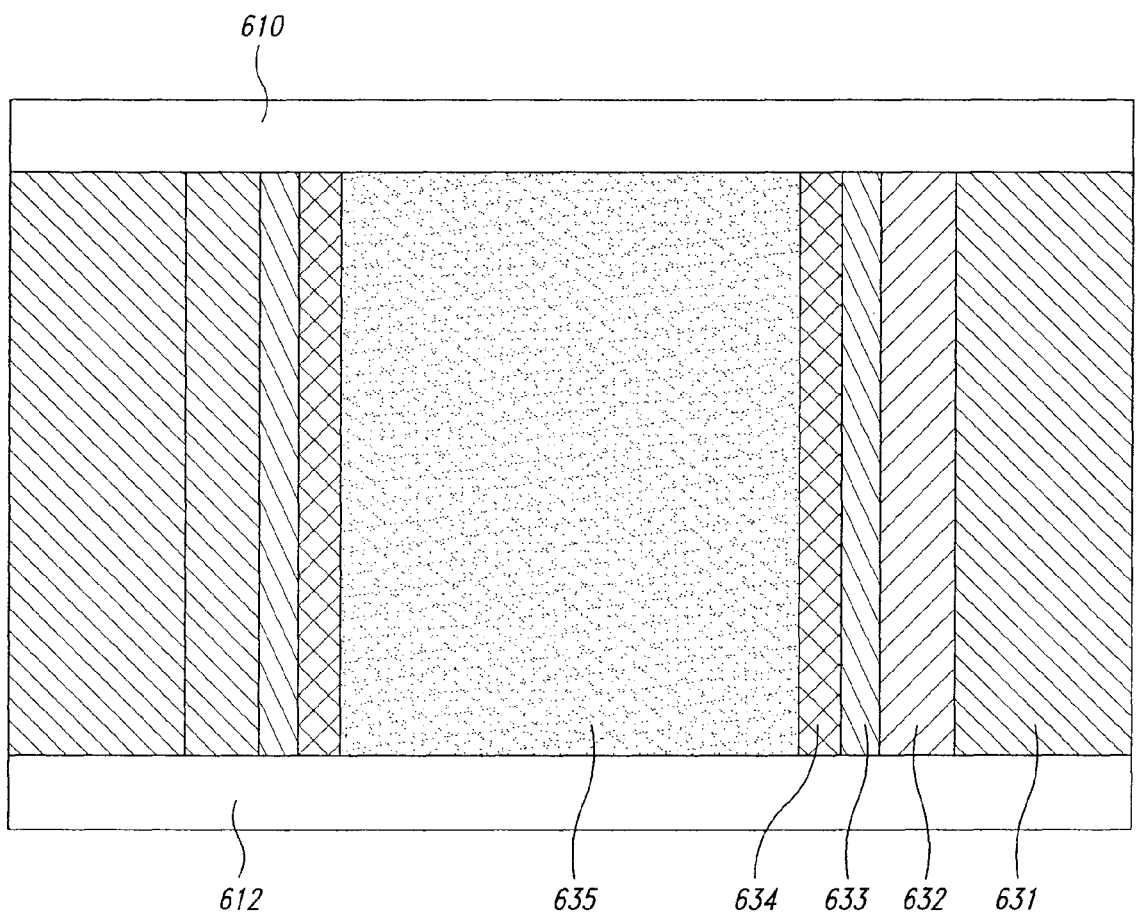
FIG. 7 illustrates a cross section of the dosage form of FIG. 5 along line 7-7 in accordance with principles of the present invention.

FIG. 7 is a cross-section of the dosage for of FIG. 5 along line 7-7 and illustrates a set of regions such that the regional concentration of API increases monotonically from the outermost to the innermost of five discrete nested regions. Similarly, the regional concentration could monotonically decrease as one goes from the outside of the dosage form to the most central or last-to-erode portion of the dosage form (again, with the realization that the innermost region may either contain API or be free of API). Further details are provided in the Examples. It is also possible to create distributions of API concentration of nested regions that are more complicated than monotonic distributions. Such distributions could be used to provide release profiles that are more complicated than zero-order or escalating or decreasing release profiles mentioned. More than one API could each have individual, different release profiles.

A rectangular prismatic dosage form could also be constructed with capped ends, if desired, so that there would be certain surfaces that do not recede or release API. In this case each region would be surrounded by the region outside it except for the ends of the regions that could touch the end caps similar to what has already been illustrated for a cylindrical dosage form with end caps. Similar considerations apply to any other shape of dosage form.

Each region has one or more wall thicknesses describing it, and each region also has overall dimensions describing the exterior dimensions of the region (such as an overall axial dimension and an overall diameter or radius, in the case of cylindrical regions). The regional wall thickness(es) may be chosen such that they are small compared to the overall dimension(s) of the particular region, such as less than one-third of the overall dimension of the particular region. If this is done it will insure that the surface area of the region does not change by a very large fraction during the release from that region, from the beginning of erosion/degradation of that region to the end of erosion/degradation of that region. This, in turn, helps in achieving zero-order release. This is not required, however.

It will be seen in the Examples that using the designs of the present invention with all regions including the innermost region containing API, it is possible to achieve release which is close to zero-order (constant rate), except that near the end of the release there may be a departure from this ideal in that the release rate exhibits a decrease during a brief period of time shortly before extinction of the dosage form. This slight departure from zero-order occurs because as the innermost region erodes or degrades, having what may be assumed to be a uniform API concentration throughout its volume, this innermost region does experience a decrease of surface area without a compensating increase of API concentration. This causes a decreasing-with-time release during the later portions of the release from the innermost region. This experiencing of a substantial decrease in surface area during release from a particular region is in contrast to what is experienced with nested thin-walled regions, for which the surface area may be approximately constant during the time when any individual region or shell is being eroded or degraded and for which the regional API concentration may be adjusted to match the regional surface area. As one comes closer to the very center of the dosage form, such as at the innermost region which for purposes of achieving zero-order release would be required to have the greatest concentration of API, there is a practical limitation in that it is not possible for the API concentration to become infinite as would be required by the theoretical suggestion (Eq. 10).

Accordingly, if it is an overriding concern that the release of API be very close to zero-order, it would be possible to leave the innermost region free of API. In such a design, all of the actual release of API would occur from regions whose release is governed by the wall thickness of relatively thin-walled regions and which therefore can release in a manner which is very close to zero-order (constant rate). In such a design, the innermost region, because of its non-ideal release behavior, may simply be manufactured so as to contain no API, so that its erosion/degradation characteristics simply do not matter for purposes of release of API, because no API is being released as the innermost region erodes/degrades. Such inertness of the innermost region may decrease the overall API-carrying capacity of the dosage form, in terms of the total amount of API that may be packed into the overall dimensions of the dosage form. Nevertheless, such a design may still be useful because of its extremely close approximation of zero-order release. Such a design may be most suitable for low-dose API in which it is not critical to pack the largest possible amount of API into a dosage form. Of course, such a design may also be useful for release profiles other than a purely zero-order release profile.

Discussion so far has described dosage forms that have discrete regions, with each region being characterized by its own concentration of API that is different from that of neighboring regions, resulting in a distribution of API concentration that is described by discrete steps. It is also possible that the API concentration might vary with position in a manner that is somewhat more continuous, i.e., in which the variation does not have discrete sharply-defined steps. For example, the variation of API concentration could be somewhat stepwise but including somewhat of a gradual transition where steps meet each other, or the variation could be essentially a gradient with essentially no stepping effect, or anywhere between these two situations. Such situations can be achieved or adjusted as a function of the thickness of powder layer used in the 3DP printing process, the wall thickness(es) of individual regions, and/or the saturation parameter used during 3DP, such as by adjusting the printing situation so that a significant amount of bleeding occurs, as will be described later.

As far as materials of construction, the bulk of the dosage form may comprise a pharmaceutical excipient material that is subject to erosion or degradation upon immersion in a liquid such as water. It may, for example, be a material that forms a gel upon exposure to water. One example of such a material that may be used in the practice of the present invention is hydroxypropyl methylcellulose (HPMC), which is a hydrophilic polymer that is a well-characterized pharmaceutical excipient. The behavior of HPMC when exposed to water includes formation of a gel layer at the water-HPMC surface, as described further in Example 1. The bulk material may further include an adjuvant, such as lactose, which accelerates the degradation of erosion or dissolution of the bulk material when it is in contact with a liquid, as is also described in Example 1. Possible adjuvant materials include lactose, other sugars, sodium chloride, other salts, and in general other water-soluble materials.

The API may be essentially any API including API having any degree of water solubility, ranging from highly soluble to substantially insoluble. The dosage form may further include a binder substance that is suitable to bind powder particles together, such as polyvinyl pyrrolidone (PVP) or methacrylate polymers or other polymers, as long as the dosage form displays release characteristics of the type described herein.

Method of Manufacturing Dosage Form

The dosage form of the present invention may be manufactured by three-dimensional printing. Three-Dimensional Printing, described in U.S. Pat. No. 5,204,055 and elsewhere, provides the ability to distribute API non-uniformly throughout a dosage form, which is useful for achieving desired release profiles.

Figure 8:
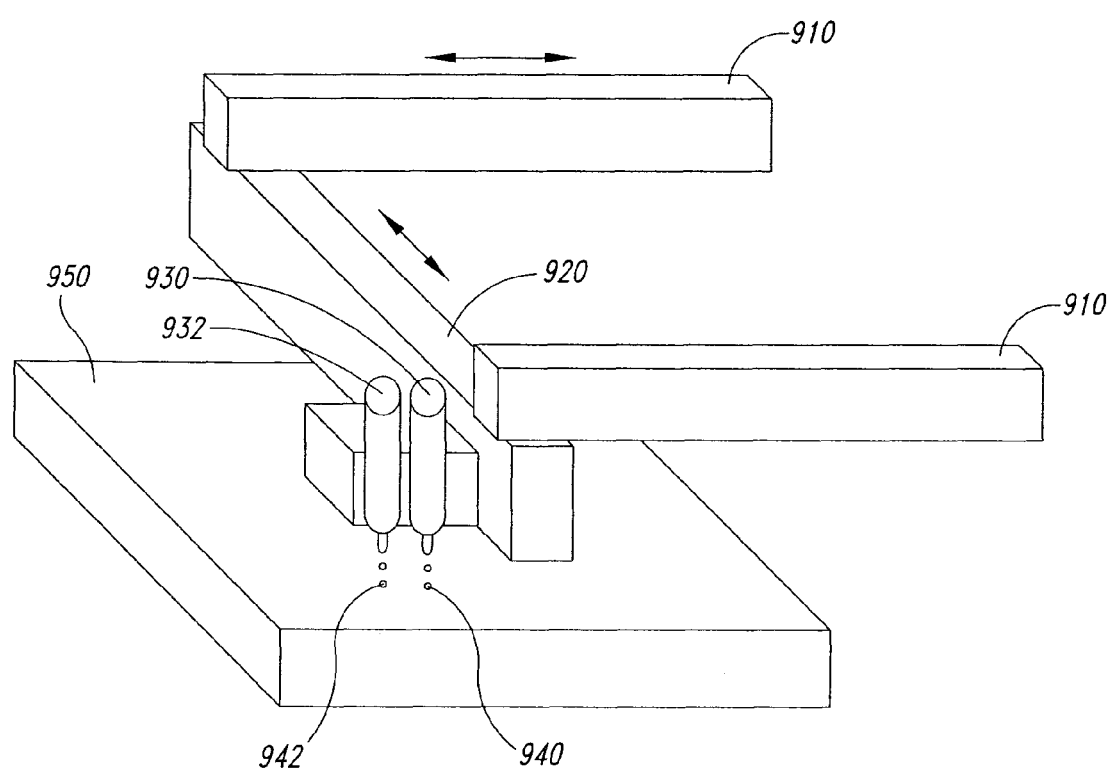
FIG. 8 illustrates the basic three-dimensional printing (3DP) process according to the prior art.

FIG. 8 illustrates the basic three-dimensional printing process. As shown in FIG. 8, drops of a binder liquid 940, 942 may be dispensed by dispensers 930, 932 onto a layer of powder 950 by a technique similar to ink-jet printing. The dispensers may be moved by motion control apparatus that may include rails or axes 910, 920. Either raster printing or vector printing, or both, in any combination, may be used. Powder particles may be joined together by the action of the binder liquid. Subsequent powder layers may be sequentially deposited and drops of binder liquid dispensed until the desired three-dimensional object is created. Unbound powder supports printed regions until the article is sufficiently dry and then the unbound powder is removed. When a dosage form is being made by 3DP, API may be contained in the binder liquid that is dispensed onto the pharmaceutical excipient powder.

One possible purpose of the binder liquid is to carry the desired substances, which may include dissolved or even suspended API, to the powder layer 950, in selected places and in selected quantities. Another possible purpose of the binder liquid is to cause particles to bind to each other. The binder liquid may further serve both of these functions or some portion thereof. Binding of the particles can occur through any one or more of several mechanisms. One mechanism is that the binder liquid may act as a solvent of at least some of the bulk material or powder, in which case the liquid actually dissolves some of the powder. As the solvent in the liquid evaporates, the particles may resolidify such that they are joined together. Another possible mechanism is that the binder liquid simply solidifies around solid particles or solidifies such that it is connected to solid particles, thereby binding them. The binder liquid may contain a dissolved binding substance that is left behind when the volatile part of the binder liquid evaporates, and upon evaporation of the volatile, the dissolved binder substance may solidify around solid particles or solidify such that it is connected to solid particles, thereby binding solid particles together. The dissolved substance may be an inorganic substance or a low molecular weight (non-polymeric) organic substance or may be a polymer.

Figure 9:
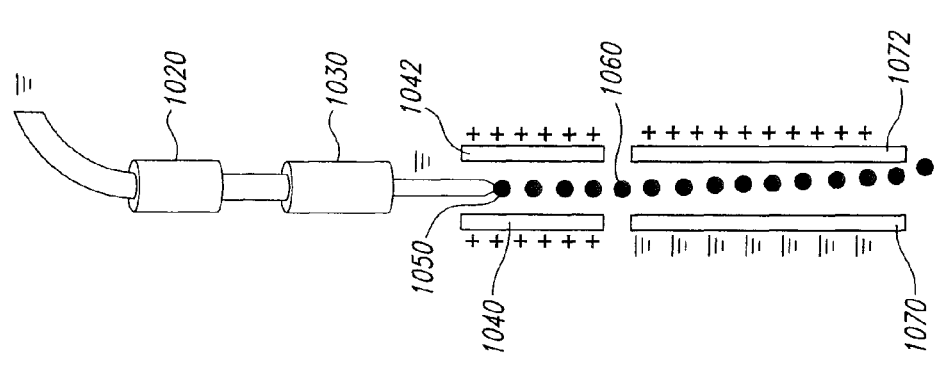
FIG. 9 illustrates the basic operation of a Continuous-Jet Charge-and-Deflect printhead according to the prior art.

The binder liquid may be dispensed onto the powder by any one or more of several types of printheads or dispensers. FIG. 9 schematically illustrates a Continuous Jet printhead with Charge and Deflection. In such a printhead, a continuous stream of pressure-driven flow may flow through an orifice and may be modulated using an excitation device located slightly upstream of the orifice, resulting in a controlled droplet break off. Individual droplets are either allowed to travel to the powder bed, or are instead "caught" by a system that applies a charge to droplets and then deflects them selectively into a collection system where they may be recycled.

The first of these steps may be stream modulation. The fluid 1010 may be forced through a piezoelectric tube actuator 1020 which may be electrically powered by a function generator (not shown). The piezoelectric actuator 1020 of the present invention may for example operate at 30 to 60 KHz. The mechanical vibration introduced into the fluid stream may induce droplet break off after the liquid exits the orifice 1030. The orifice diameter may be approximately 50 micrometers.

In order for droplets to be controlled using computer instructions, individual droplets may be charged electrostatically. The stream may pass between two substantially parallel charging plates 1040, 1042 such that breakup of the stream into individual droplets 1050 occurs between the plates 1040, 1042. If the charging cell is "on," droplets 1050 may acquire an electrostatic charge just before or at the time when they break off from the stream between the plates. The stream may be grounded to assist in this. Droplets assume the charge that the fluid in the charging cell had at the moment of droplet breakoff from the stream. Downstream of the point at which droplets break off from the stream, the individual droplets are electrically isolated from one another and retain the charge they had at the time of breakoff from the continuous stream. The charging cell is "off" when the plates are neutral or uncharged. In this situation, droplets 1050 breaking off from the jet remain neutral or uncharged.

Droplets 1060 exiting the charging cell may then travel between two approximately parallel deflection plates 1070, 1072. These deflection plates may create an electrostatic field between them. For example, one deflection plate may carry a substantial voltage and the opposite plate may be grounded. Uncharged droplets exiting the charging cells, for example, when the charging cell is "off," may pass through this electric field and continue straight to the powder bed to be printed. Thus, when the charging cell is "off," the printhead may dispense fluid to the powder bed downstream of it. Droplets exiting the charging cell when the charging cell has voltage, for example, when the charging cell is "on," may be deflected towards one of the deflection plates. A catcher 1080, which may be cylindrical, may be located near the deflection plate towards which the deflected drops travel and directly in the path of a deflected droplets. Droplets which strike the catcher 1080 may be removed such as by being vacuumed into a collection unit for later recycling. In the operation of a Continuous Jet Charge and Deflection printhead, typically much of the liquid is recycled rather than being printed onto a print job. It is also possible in a continuous jet charge and deflect printhead for drops to be given a charge which varies continuously within a range so that even drops which proceed to the powder bed may be partially deflected. This provides opportunity for detailed individual control of the placement of those drops that do travel to the powder bed.

Figure 10:
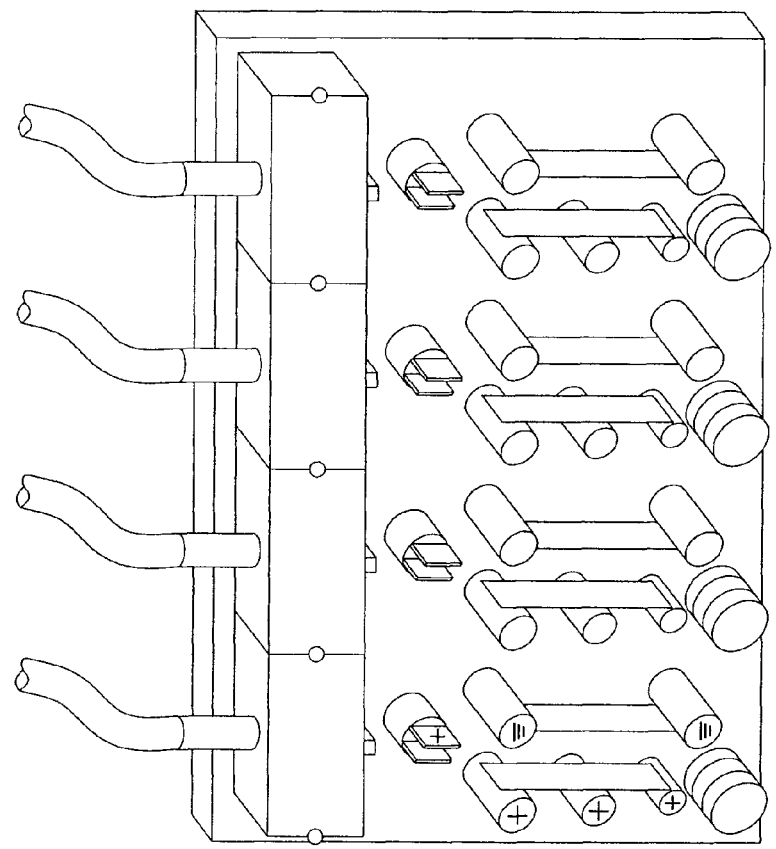
FIG. 10 illustrates a Continuous-Jet Charge-and-Deflect printhead suitable for the practice of the present invention according to the prior art.

FIG. 10 illustrates a Continuous Jet Charge and Deflection printhead suitable for the practice of the present invention, containing four individual dispensers of the type illustrated in FIG. 9. In this printhead, each dispenser is a complete unit which may be independently operated and which may be supplied by its own fluid supply having its own fluid composition etc. Other types of printheads are also possible, such as microvalves and piezoelectric dispensers.

Dispensing of different concentrations of API into different regions of a dosage form may be achieved by dispensing a single API-containing binder liquid of fixed composition but dispensing it a prescribed number of times in certain places on any given powder layer. Between repeated dispensings, some time may be allowed for earlier-deposited liquid to at least partially dry. This would result in regional API concentrations being either the API concentration that would occur in a one-time-printed region or integer multiples of the API concentration that would occur in a one-time-printed region. Alternatively, it would be possible to dispense more than one binder liquid, wherein the various binder liquids might all contain the same chemical species of API or other constituents but might contain them in different concentrations. In this case it would be possible to create essentially any desired relationship among the numerical values of API concentration in various regions. A printhead containing several separate dispensers and fluid supply systems, as shown in FIG. 10, would facilitate this. Of course, it would also be possible to dispense more than one binder liquid, each binder liquid containing different species or constituents.

After completion of three-dimensional printing, the dosage form may be dried for a sufficient period of time and then may be separated from unbound powder, and, if necessary, attached loose powder may be removed from the dosage form. Another follow-up step that may optionally be used in the present invention is compression of the dosage form at this point. In the present invention compression is not absolutely required, although it is helpful in certain respects. For example, a material system such as uncompressed HPMC/Lactose would still be porous following printing. In the uncompressed state, the dosage form would not have followed the erosion/degradation release profiles as effectively as it does in the data reported herein, since the porosity would have acted as increased surface area and made the release time quite short (<1 hour), and the porosity might have allowed particular places in the interior of the dosage form to be exposed to liquid by seepage of liquid before the degradation/erosion front actually reached the particular places.

Figure 11:
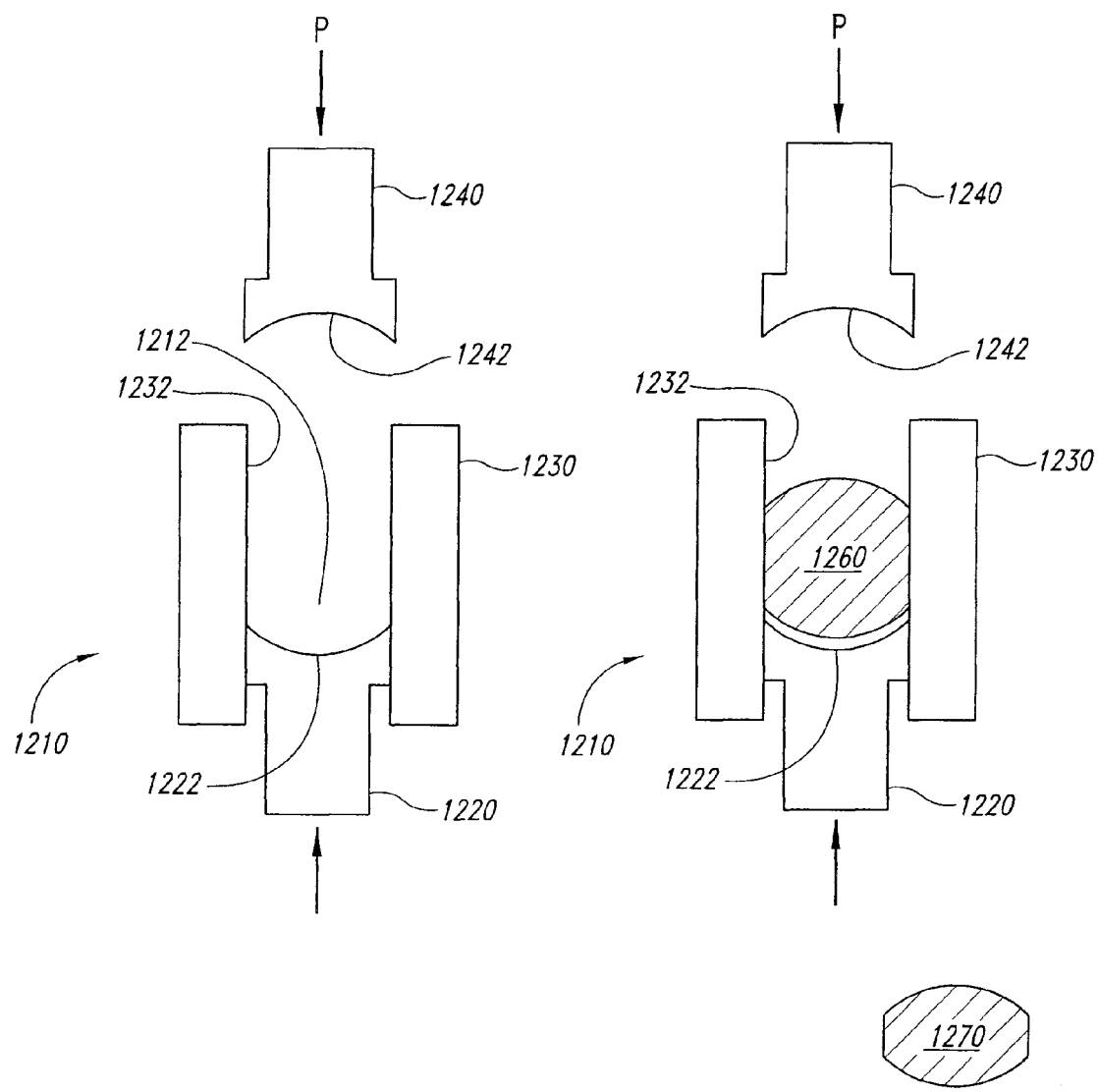
FIG. 11 illustrates uniaxial compression of a dosage form after the dosage form has been made by three-dimensional printing according to a copending application.

Compression of a dosage form after 3DP is illustrated in FIG. 11. In order to perform compression, the 3DP printed article may be placed individually into a cavity in a press suitable to exert significant compressive force on the printed article from one direction such as by means of a ram, while in substantially all other directions the printed article is confined against rigid surfaces. For a shape of dosage form comprising a cylindrical portion and possibly curved end portions, all having cylindrical symmetry, the easiest axis along which to perform uniaxial compression on the article such as a 3DP printed article may be the cylindrical axis. Even if the article lacks cylindrical symmetry or even any symmetry, it can still be compressed according to the present invention.

The article may be manufactured with a dimension, along the axis of compression, which is greater than the desired final dimension of the dosage form by a factor that is determined by the expected extent of compression. The dimensions of the article in a cross-section perpendicular to the pressing axis may be just slightly smaller than the interior dimensions of the die assembly, so as to allow for easy insertion of the article into a die cavity. The axis of compression may coincide with the vertical (layer-to-layer) build direction of the 3DP printing process, although it does not have to.

As shown in FIG. 11, the press may comprise a die 1210 having a receiving cavity 1212 whose lower features correspond to the desired shape of the bottom of the compressed dosage form. The die 1210 may be made of two close-fitting parts, i.e., a lower die 1220 and a sleeve 1230. A design in which lower die 1220 is separate from the sleeve 1230 allows for ejection of the dosage form after pressing by moving the lower die 1220 and the sleeve 1230 relative to each other.

Alternatively, it is possible to perform compression using a single-piece cavity where the lower die 1220 and the sleeve 1230 are integral with each other rather than being separate pieces as illustrated. The lower die 1220 has a lower die surface 1222 facing the article 1260. A ram 1240 having a ram surface 1242 facing the article 1260 presses on the surface of article 1260 that is away from lower die 1220. The die or receiving cavity 1212 may have a bore of constant cross-section for at least part of its distance. Ram 1240 may be adapted to slide in a close-fitting manner into the bore of die 1210. The bore and the ram may have cylindrical symmetry with the axis of the cylindrical symmetry being parallel to the axis of motion.

The bottom die 1220, sleeve 1230 and ram 1240 may closely confine the printed article 1260 from all directions with no significant holes or leakage. The outside diameter or shape of the ram 1240 and the inside diameter or shape of the sleeve 1230 may be such as to provide a close sliding fit, and the same may be true for the outside diameter or shape of the lower die 1220 and the inside diameter or shape of the sleeve 1230 if these are separate parts from each other.

Non-circular cross-sections of the ram and die are possible, including shapes without symmetry. The ram, die and sleeve may fit closely with respect to each other such that the only places facing the printed article which are not perfectly solid are those small gaps where sliding motion takes place between closely-fitting parts.

Surfaces 1222 and 1242 define the lower and upper surfaces of the eventual compressed dosage form 1270 and may be shaped according to the desired final shape of the dosage form. Either or both of these surfaces may be made curved in order to produce curved surfaces of the dosage form. Alternatively, either or both of these surfaces may be flat.

Lower die 1220, sleeve 1230 and ram 1240, or at least their surfaces 1222, 1232 and 1242 which contact the article, may be made so as to be harder than the hardness of the article produced by the 3DP process. All of the surfaces 1222, 1232 and 1242 that contact the printed article during compression may be smooth with a specified surface finish so that the after-compression surfaces of the dosage form are similarly smooth to the degree or smoothness desired.

A non-smooth surface may sometimes be desirable to produce identifying characters or similar markings, known as trade dress, on some surfaces of tablets by means of the pressing operation as is sometimes done in conventional tabletting. To accomplish this, features such as projections or recesses can be incorporated into lower die surface 1222 or ram surface 1242 or both. The article 1260 may be printed from 3DP printing instructions such that its shape and dimensions correspond to the shape and dimensions of the lower die surface 1222 and ram surface 1242, which will result in relatively little rearrangement of printed material occurring during compression.

After the article 1260 such as a 3DP printed article is placed in the cavity 1212, the ram 1240 may be brought down upon the article 1260. A suitable pressure for pressing the article such as a 3DP printed article in order to eliminate essentially all the void space is approximately 15,000 lbf/inch^2 (psi), which is defined as compression force P divided by the cross-sectional area of the bore of the cavity 1212 or the maximum cross-sectional area of the printed article 1260 in any cross-section taken perpendicular to the axis of pressing.

For typical excipient powders, binder substances, and the like, such a pressure may compact most of the void space which remains after 3DP and may maintain or cause adhesion of the particles and deposited substances to each other resulting in a dosage form which is almost fully dense. It is believed that smaller compressing pressures even in the range of approximately 5,000 lbf/inch^2 (psi) would still be suitable to smooth the surface and remove almost the entire void, at least for some powders. Compression times on the order of seconds are more than adequate to accomplish the desired compaction. Compression to an extent such as to remove only some of the void space is also possible. This compression operation transforms article 1260 such as a 3DP printed article into dosage form 1270.

Another possible method of compression is isostatic pressing. This involves enclosing the article to be compressed in a flexible bag, and then applying hydrostatic pressure directly to the outside of the bag.

Compression can eliminate much or essentially all of the void space between powder particles and can change the rate of erosion of the dosage form in bodily fluids, making the erosion rate slower. In particular, compression can make the erosion rate less dependent on details of the three-dimensional printing process and can prevent liquid from seeping into interior locations inside the dosage form before the erosion/degradation front actually reaches those locations.

Method of Design of Dosage Form

The present invention also includes a method of designing a dosage form to achieve a desired release profile of the API. The design method makes use of the principles contained in the Hopfenberg and Katzhendler models, but it further includes the modeling of arbitrary distributions of API concentration within the dosage form, and such models could further be generalized to arbitrary geometries of dosage form. In order to use the Hopfenberg and Katzhendler models for this purpose, a first step is to determine numerical values for the release rate constants (the various k) that appear in the equations of those models. This can be done using relatively simple experiments with dosage forms having uniform concentration distribution, as described in Example 2. The erosion/degradation process and the release rate constants may be a function of the materials themselves and also of the manufacturing methods, e.g., compression. Then, a proposed design of a dosage form may be described in terms of the geometry and spatial distribution of API concentration. As discussed elsewhere herein, at least some of the dimensions of regions may be selected so that they correspond to integer numbers of thicknesses of powder layers in the three-dimensional printing process. Concentrations of API in various regions may be selected as described elsewhere herein.

Figure 12:
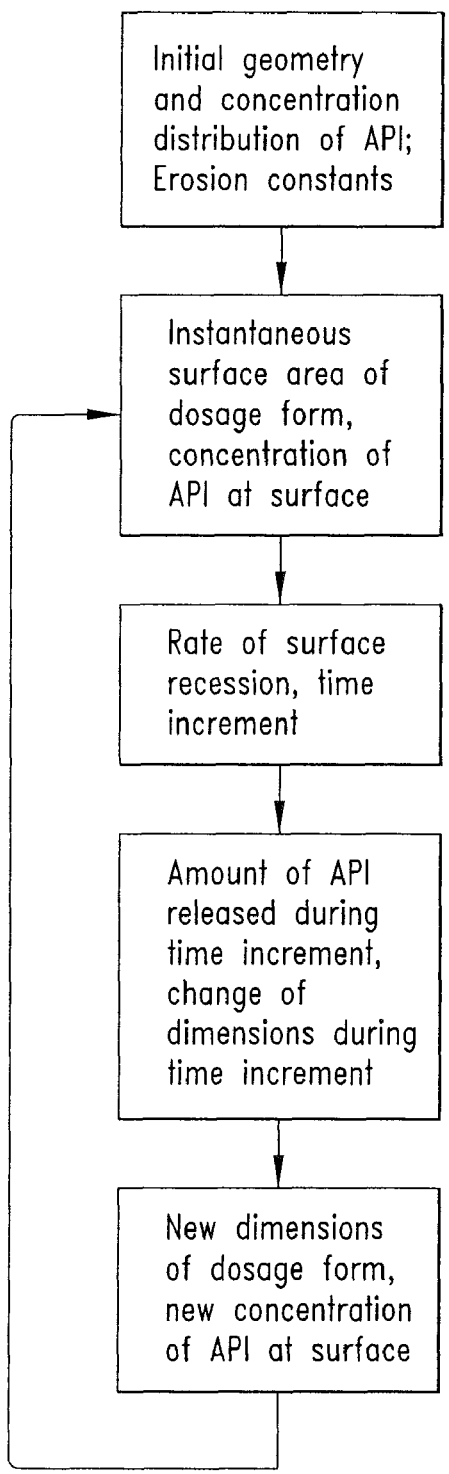
FIG. 12 is a flowchart of an analytical model that may be used to predict the release profile of dosage forms in accordance with principles of the present invention.

This information may serve as initial conditions for a modeling procedure that marches forward in time such as by explicit timewise integration. This modeling process is illustrated in the flowchart of FIG. 12. At the beginning of any particular timestep, there is a known instantaneous surface area of the dosage form (or of the release-determining feature of the dosage form) and a known instantaneous concentration of API at the surface (or release-determining feature) of the dosage form. (Discussion of a release-determining feature of a dosage form is given in Example 1.) This information, together with timestep duration and the surface recession rate that determines the rate of dimensional change of the dosage form, determines the overall amount of material removed from the dosage form during a given timestep and the amount of API released during a given timestep.

For purposes of analytical modeling, if there is no data indicating otherwise, it may be assumed that the surface recession rates or release rates in all directions are constant and equal. The instantaneous surface area of the dosage form may be denoted by A, and the API concentration in that volume element may be denoted by C. At every time interval, delta t, the front or effective surface of the dosage form moves a fixed distance, delta I, into the dosage form, and the incremental volume released is A*delta I. The incremental API release from each element is C*A*delta I. The surface area, A, of the front typically decreases as the erosion or degradation process progresses, and therefore the volume increments, A*delta I, also typically decrease as the erosion or degradation process progresses.

At the end of a timestep, the calculated dimensional change of the dosage form during a particular timestep can be used to calculate new dosage form dimensions at the end of the timestep. The new concentration of API at the location of the dosage form surface at the end of the timestep can be obtained from tabular or other relational data describing local API concentration as a function of the instantaneous dimensions of the dosage form. Amounts of API released during the timestep can be added to amounts previously released to provide a cumulative amount of API released from the dosage form to the surrounding liquid. Then, with new dosage form dimensions and API concentration at the surface as of the end of the timestep, a new iteration can be begun for the next timestep. Such calculations can be executed on a spreadsheet or with a custom-written computer program, as is known in the art.

Figure 13:
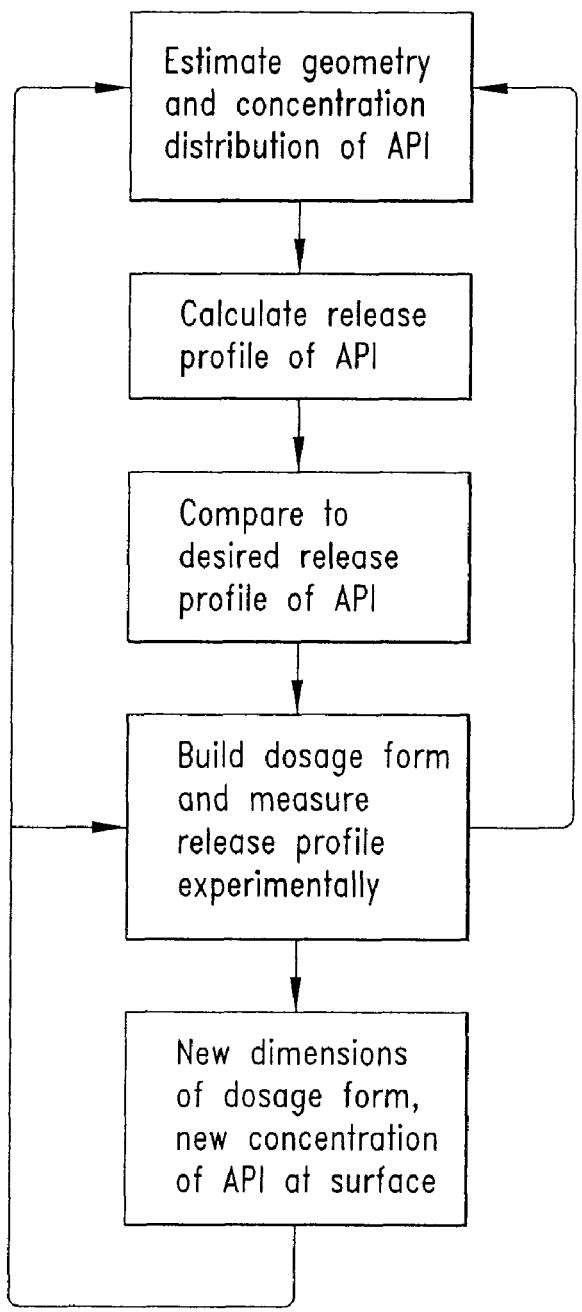
FIG. 13 is a flowchart of a dosage form design method of the present invention for attaining a desired release profile in accordance with principles of the present invention.

The flowchart of FIG. 13 illustrates an iterative procedure for the complete process of designing a dosage form to give a desired release profile, according to the present invention. After a calculated release profile has been obtained from this modeling procedure, the calculated release profile may be compared to a desired release profile. Then, as part of the process of designing a dosage form, adjustments may be made to dimensions of regions or to concentrations of API in regions of the dosage form, in order to bring the calculated release profile closer to the desired release profile.

FIG. 13 shows this iteration that may be performed as many times as desired. At some point, when the release profile predicted by the model is sufficiently similar to the desired release profile, dosage forms could be fabricated, such as by three-dimensional printing, and could be tested by being dissolved under controlled conditions, as described elsewhere herein. The experimentally determined release profile could then be compared to the desired release profile. If the experimentally determined release profile is not sufficiently close to the desired release profile, then further changes could be made to the design, and a dosage form incorporating such design changes may again be modeled and then made, or may simply be made, and can be tested further. With the techniques described herein, it should be possible to achieve a desired release profile with very few such iterations of experimentation, i.e., actually building a dosage form and conducting dissolution experiments. In fact, it may be possible to achieve a desired release profile on the first experiment, with no repetition of experiments being necessary.

The invention is further described but is in no way limited by the following Examples.

EXAMPLES

Example 1

Basic Observations about Degradation Characteristics of Dosage Forms Based on Hydrophilic HPMC The Hopfenberg and Katzhendler models describe the release of API based on the assumption that erosion/degradation of the dosage form material, or more specifically release of API, occurs at the surface of the dosage form with constant rates of recession of the surface. It is therefore important to determine if the erosion/degradation in a particular materials system satisfies these assumptions.

The materials system chosen to fabricate Examples of the dosage forms of the present invention included the hydrophilic bulk material component hydroxypropyl methylcellulose, or Methocel® HPMC (Dow Chemical Company, Midland, Mich.). This HPMC powder was, in most cases, further mixed with an adjuvant substance that was lactose monohydrate (Pharmatose DCL11) (DMV International, The Netherlands) to make up the powder bed onto which the binder liquid possibly containing API was printed. An adjuvant is a material that is added, such as to modify properties. In this case the adjuvant was a material that was more quickly water-soluble than HPMC, so as to change the time scale for erosion or degradation or API release from a dosage form made of the mixture, compared to what would be obtained using pure HPMC. It was observed that the larger the fraction of lactose, the faster the dosage form degraded or dissolved. In this case the adjuvant was lactose, but it would also be possible to use other sugars, sodium chloride, other water-soluble salts and, in general, other water-soluble materials.

It was observed that when HPMC was used as a bulk material or excipient for a dosage form, either with or without an adjuvant material being mixed together with it, an outermost layer of the HPMC quickly hydrated to form a protective gel barrier layer. As water diffused into the HPMC-based dosage form, the HPMC concentration in the hydrated gel layer decreased. The outermost layer of the dosage form became dilute enough for individual chains of polymer to disentangle from the surface by reptation and go into bulk solution. This occurred when the polymer concentration became diluted below a critical polymer concentration, resulting in surface erosion from the dosage form. Release kinetics can be described as a coupling of API diffusion and polymer dissolution, i.e., surface erosion.

The release of highly water-soluble API from such a system has been shown to depend on movement of the diffusion front in the gel layer. It is this relaxation front moving into the center of the dosage form that dictates the kinetics of release from the inner gel boundary. For release of water-insoluble APIs and/or the use of lower viscosity grades of HPMC, the bulk dissolution of the HPMC, or the erosion of the gel itself from the outer regions of gel, may contribute significantly to the overall release kinetics. In any event, whatever the water solubility of the API and the viscosity grade of the HPMC, it appears that HPMC based formulations have the ability to maintain API release at the surface of the dosage form, which means that the API release may be modeled as advancement of the surface of the dosage form at a constant rate with release of whatever API was at the surface of the dosage form, which are the assumptions of the Hopfenberg and Katzhendler models.

Dosage forms using this materials system were fabricated by 3DP and tested. The powder was 70% lactose 53-74 micrometers and 30% HPMC K4M 53-74 micrometers, and the API solution was 18 wt % diclofenac sodium+0.05 wt % fluorescein sodium in methanol+1 wt % polyvinyl pyrrolidone. Fluorescein is useful as a marker substance. It is a highly water-soluble compound with strong fluorescence under UltraViolet light even at very dilute concentrations. These dosage forms were printed with uniform concentration of API everywhere, 32 layers high, and were pressed under uniaxial compression to yield dosage forms 11 mm in diameter and 4.8 mm in height. The overall API content in the dosage forms was 101.8 mg.

The dosage form thus made was sandwiched between two glass microscope slides, and the assembly was clipped together using standard 1.9 cm binder clips. The assembly was then placed in a standard United States Pharmacopeia (USP) Type I dissolution cell using the USP paddle technique with a speed of 100 rotations/minute in 900 mL of phosphate buffer of pH 7.4 at 37° C. At various time points the assembly was removed from the dissolution cell and was photographed under UV light and white light to show the location of the dissolution front as a function of time. The assembly was then returned to the dissolution cell for continued testing.

Figure 14:
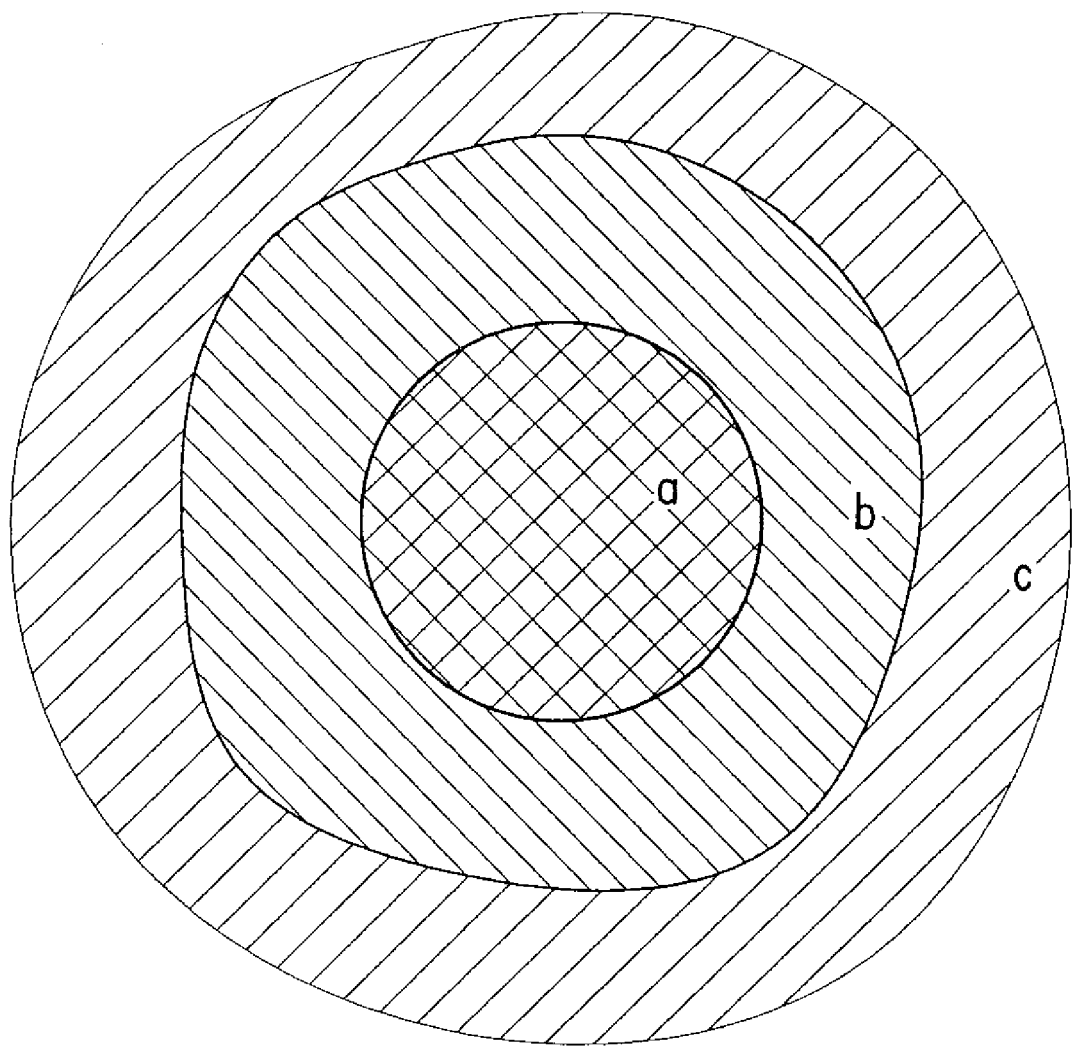
FIG. 14 illustrates a dosage form after 30 minutes of immersion in a liquid, showing formation of a layer of gel at the surface of the dosage form in accordance with principles of the present invention.

FIG. 14 shows an illustration of a photograph of the assembly at t=0.5 hr after immersion in the phosphate buffer aqueous solution. Degradation was observed to occur at the surface of the dosage form as a gel layer was almost immediately formed around the edge, preventing the diffusion of water further into the interior of the dosage form. Chemically and rheologically, the gel layer was very complex. The gel layer began at the solid/hydration front where the HPMC chains began to disentangle, and continued outward where the gel was increasingly weaker and easy to shear. The solid/hydration front can be clearly discerned visually. In FIG. 14 the solid/hydration front is labeled at the boundary between regions a and b. This was the point at which the HPMC began to hydrate and reptation began. The solid portion of the dosage form, not yet affected by the dissolution liquid, is represented by region a. The complex gel region is represented by region b, and the weak diffuse gel/water solution is represented by region c. The outermost visible circle is the water meniscus.

It has been shown that polymer relaxation stress at the solid/hydration front contributes to transport of API for both high aqueous solubility API and low aqueous solubility API and for varying API loadings. Under UV light, very little fluorescein was observed at any radius larger than the solid/hydration front. In all cases, the fluorescent yellow coloration disappeared quickly, at a distance less than 1 mm outside (greater radius than) the solid/hydration front. This suggests that what determines the release of water-soluble API from a dosage form based on a gel-forming material is the position of the solid/hydration front. The diameter and radius of the solid region (the region inside the solid/hydration front) were optically measured in four angularly spaced directions and the results were averaged to give the position of the solid/hydration front as a function of time. The results are shown in FIG. 15.

Figure 15:
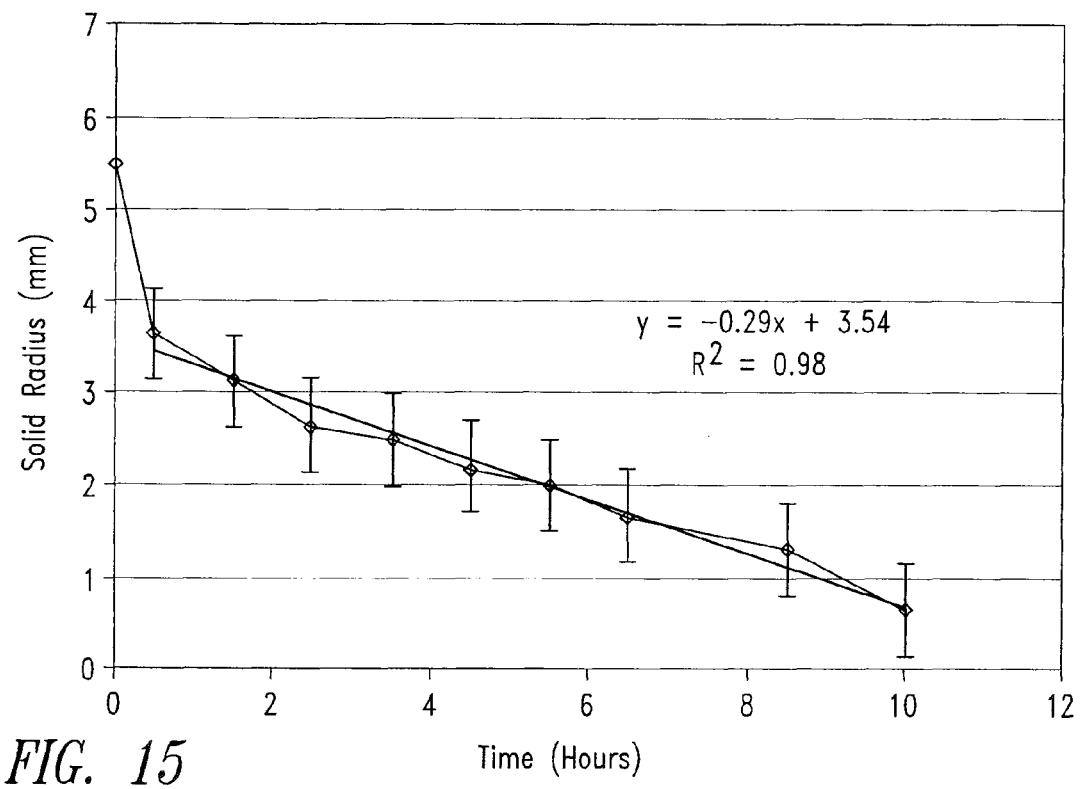
FIG. 15 graphically illustrates the position of the solid/hydration front as a function of time, for the dosage form of FIG. 14 in accordance with principles of the present invention.

In the data of FIG. 15 there appears to be a brief initial stage during which the behavior is different from the behavior during later times. This initial stage corresponds to the initial establishment of the gel as water diffuses rapidly into the surface of the dosage form. This initial effect is also known as the burst effect, and in dosage forms based on similar hydrophilic materials this effect has been shown to result in some immediate API release before the gel layer is established. After completion of this initial stage, this solid/hydration front was observed to move radially inward at an essentially constant rate. A linear regression through the data of FIG. 15 after the initial stage gives a rate of approximately 0.29+/−0.09 mm/hr for the inward motion of the solid/hydration front. This rate, which follows the solid/hydration or polymer relaxation front, has been shown to provide a good estimate of the actual API release rates for diclofenac sodium and chlorpheniramine maleate. When reference is made elsewhere herein to the surface of an eroding dosage form, such as for purposes of modeling, it may be understood to refer to location of a release-controlling feature such as the solid/hydration front.

Example 2

Degradation Characteristics of Dosage Forms of HPMC/Lactose of Various Compositions, Having Uniformly-Distributed API, and Determination of Erosion/Degradation/Release Constants This Example includes manufacturing some dosage forms having their API uniformly distributed (at least within an API-releasing portion of the dosage forms), and then determining the erosion/degradation/release constants that describe the dissolution of those dosage forms. In some cases, these dosage forms have been made by the relatively easy method of tablet pressing of loose powder. This Example serves several purposes. First of all, it shows that the release obtained from conventionally produced (gradient-free) dosage forms is not zero-order, thus illustrating the problem addressed by an aspect of the present invention. Similarly, it provides a comparison for later results obtained for dosage forms that do contain API concentration gradients so as to produce release profiles that are closer to zero-order. Further, this result provides values, for a particular materials system, of rate constants describing erosion/degradation/release, which are used in the later modeling for dosage forms in attempts to produce specific release profiles. Finally, these results illustrate the effect of a design variable which can be used to influence the overall time scale of the erosion/degradation/release process, namely the fractional composition of a bulk material containing both HPMC and an adjuvant material, in this case lactose.

The dosage forms for this baseline case were mostly made by compression of powder, except that those dosage forms having end caps presented near the end of this Example were made by 3DP. The dosage forms for all of these baseline experiments in this Example had the same overall dimensions as the eventual dosage forms manufactured later with compositional nonuniformity to achieve specific release profiles.

The materials system investigated here was based on the hydrophilic bulk material component hydroxypropyl methylcellulose, or Methocel® HPMC with varying percentages of an adjuvant lactose monohydrate (Pharmatose DCL11) added to the HPMC. In cases where 3DP was used, HPMC powder mixed with adjuvant was spread as the powder upon which API-containing binder liquid was dispensed. In cases of compression-formed tablets, this powder containing both HPMC and lactose was further mixed with API and was pressed to form tablets. API release rates were obtained using, as an API, either chlorpheniramine maleate or diclofenac sodium.

Figure 16:
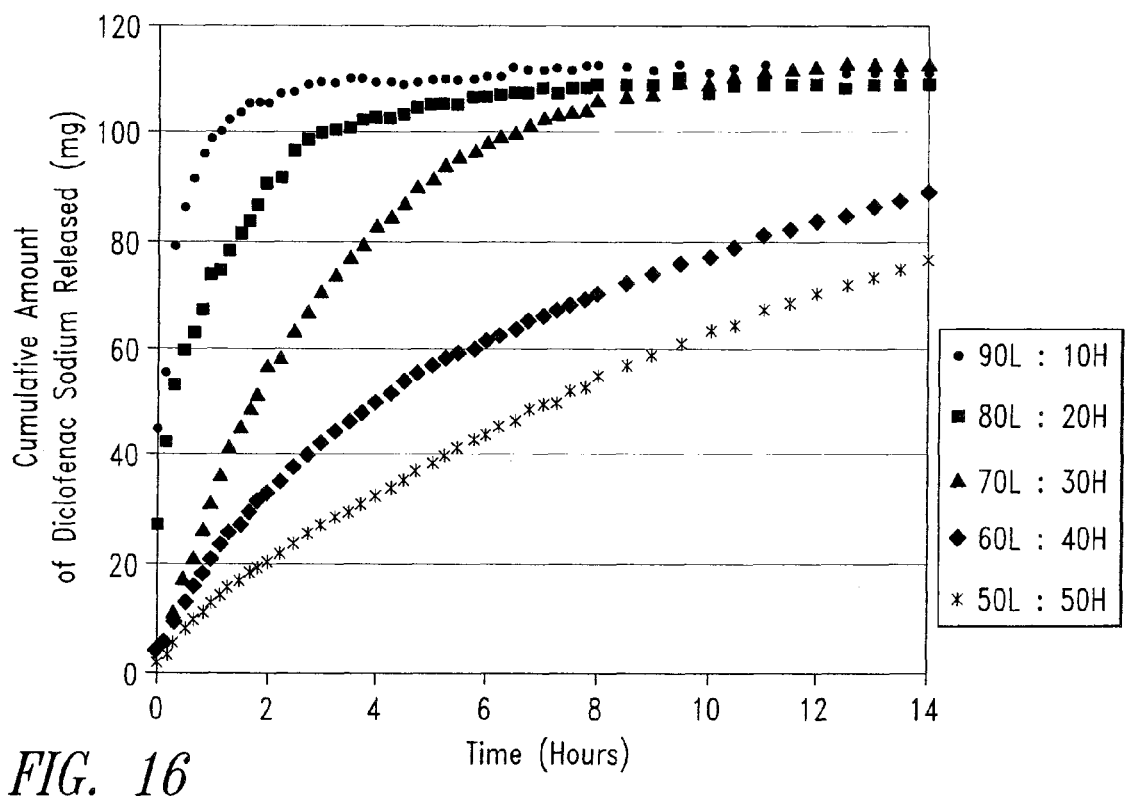
FIG. 16 graphically illustrates experimentally determined release profiles of conventionally produced (uniform-composition or gradient-free) diclofenac sodium dosage forms with varying ratios of Lactose and HPMC, with release from all of their surfaces.

First, an investigation was performed of 3-D release of conventionally pressed uniform-composition dosage forms. Conventional tablets containing varying proportions of lactose and HPMC K4M were fabricated, each containing either 100 mg of diclofenac sodium (solubility limit, $c_s$=50 mg/ml in water) (Sigma-Aldrich Corp., St. Louis Mo.) or 100 mg of chlorpheniramine maleate ($c_s$=100 mg/mL in water) (Sigma-Aldrich). Combinations of powders of Lactose, HPMC K4M, and API, as given in Table 1, were ground together with a mortar and pestle, and then were pressed using a tablet die of 11 mm in inside diameter at a pressure of 15000 psi. After compression each dosage form was 11.16 mm in diameter and 3.65 mm tall as measured by digital calipers. The concentration $C_0$ refers to the amount of API per unit volume in the dosage form after compression. These dosage forms were then dissolved using the USP Type I dissolution basket method in simulated intestinal fluid having pH 7.4 at 37° C. with a speed of 100 rotations/minute for 12 hours. The API release profiles are shown in FIG. 16 for only those dosage forms containing diclofenac sodium. This illustrates the dependence of release kinetics on the fraction of lactose in the HPMC/Lactose material. Varying the fraction of lactose adjuvant can significantly change the time scale of the erosion/degradation/release process.

TABLE 1

Composition of conventionally pressed tablets

| API | mg API | mg Lactose | mg HPMC | Lactose:HPMC | $C_o$ mg$_{API}$/cc |
|---|---|---|---|---|---|
| diclofenac sodium | 100 | 279 | 31 | 90:10 | 280 |
| diclofenac sodium | 100 | 248 | 62 | 80:20 | 280 |
| diclofenac sodium | 100 | 217 | 93 | 70:30 | 280 |
| diclofenac sodium | 100 | 186 | 124 | 60:40 | 280 |

TABLE 1-continued

Composition of conventionally pressed tablets

| API | mg API | mg Lactose | mg HPMC | Lactose:HPMC | $C_o$ mg$_{API}$/cc |
|---|---|---|---|---|---|
| diclofenac sodium | 100 | 155 | 155 | 50:50 | 280 |
| chlorpheniramine maleate | 100 | 248 | 62 | 80:20 | 280 |
| chlorpheniramine maleate | 100 | 217 | 93 | 70:30 | 280 |
| chlorpheniramine maleate | 100 | 186 | 124 | 60:40 | 280 |

Figure 17:
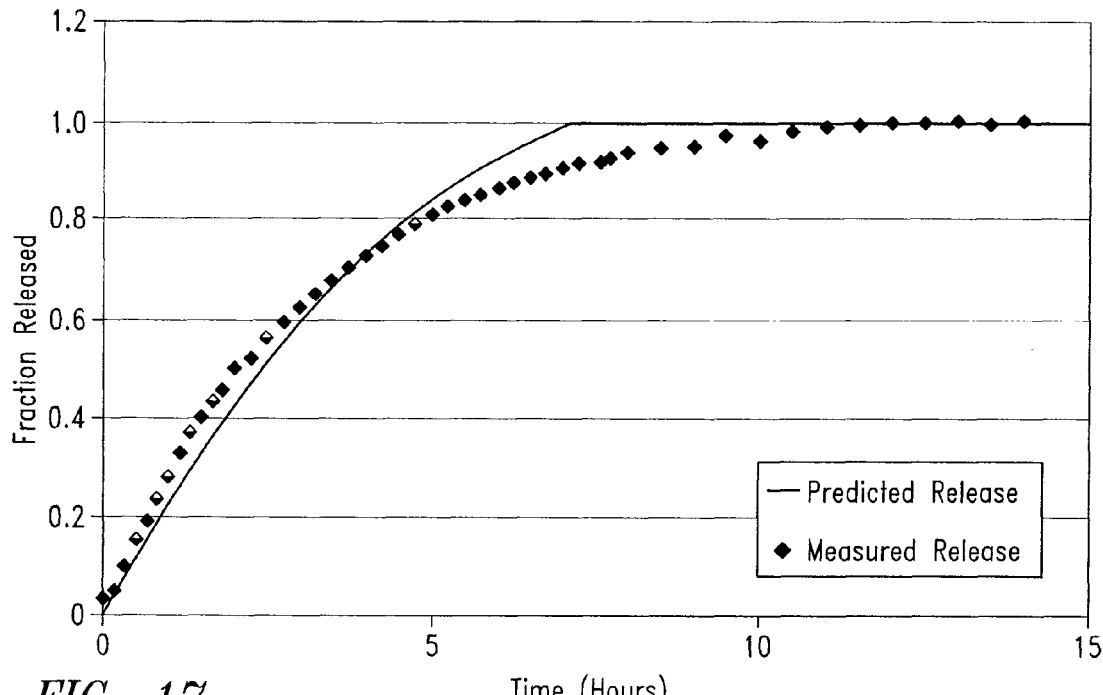
FIG. 17 graphically illustrates a comparison between the data of FIG. 16 and a curve-fit using an appropriate value of the release rate constant.

Each of the API release curves in FIG. 16 was fit to Equation 9 by performing a least-squares fit between the empirical data and model. This was done to determine the relevance of the model, and to determine rate constants for the powder/API systems for later use. FIG. 17 shows one of the data sets (70:30 Lactose:HPMC) from FIG. 16 together with a curve-fit to that data using an appropriately chosen rate constant in the Katzhendler equation. For this purpose, the rate constants in the two different directions were assumed to be equal. This case is for dosage forms containing 100 mg of diclofenac sodium in a powder system of 70% lactose and 30% HPMC using a degradation/erosion rate having a value of 9.54 mg/cm^2 sec. The agreement between the data and the result from the Katzhendler equation is good.

TABLE 2

Best fit parameters for equation 9

| API | Lactose:HPMC | $k_o$ mg/hr·cm$^2$ | $R^2$ |
|---|---|---|---|
| diclofenac sodium | 60:40 | 6.092 | 0.9886 |
| diclofenac sodium | 70:30 | 9.540 | 0.9919 |
| diclofenac sodium | 80:20 | 22.238 | 0.9871 |
| Chlorpheniramine maleate | 60:40 | 6.921 | 0.9901 |
| Chlorpheniramine maleate | 70:30 | 10.021 | 0.9876 |
| Chlorpheniramine maleate | 80:20 | 23.971 | 0.9872 |

Table 2 summarizes the results of the dissolution tests and gives the best-fit parameters for Equation 6.9 for both API for three different Lactose:HPMC ratios. The erosion rate constants are given in units of mg/hr cm$^2$ where mg is mg of API released into the dissolution fluid. $R^2$ is a statistical measure of correlation, with a value of 1 indicating perfect correlation. Table 2 shows that Equation 9 (using one $k_o$ parameter) correlates well with the data obtained from the erosion/degradation of these conventional tablets in 3-D release. The constants are used elsewhere herein for modeling predictions of other more complicated designs of dosage forms.

It can be seen in Table 2 that the addition of lactose to the bulk material of a dosage form greatly accelerated the release rates for both the diclofenac sodium and chlorpheniramine maleate dosage forms. For both API, an increase of 33% in lactose content (going from 60 grams of Lactose per 100 grams of mixture to 80 grams of Lactose per 100 grams of mixture) made the API release rate approximately three times as large.

For identical composition of the dosage form (i.e., the ratio of Lactose to HPMC), the release rates of chlorpheniramine maleate were approximately 10% higher than the corresponding release rates of diclofenac sodium. This is believed to be due to the higher solubility constant in water for chlorpheniramine maleate as compared to that for diclofenac sodium. The release of API from HPMC-based dosage forms has been shown to occur within the outer gel layer by a complicated mechanism involving API diffusion and polymer relaxation of the gel. For the two different API, the polymer relaxation of the dosage forms of equal fractions of HPMC and lactose were probably similar, but the API diffusion near the outermost portion of the gel layer probably promoted faster release of chlorpheniramine maleate due to its higher solubility in water compared to diclofenac sodium.

The linear erosion rate constants for 70% Lactose: 30% HPMC were delta r/delta t=0.341 mm/hr for diclofenac sodium, and delta r/delta t=0.358 mm/hr for chlorpheniramine maleate. These erosion rates were similar to the velocity of the solid/hydration degradation front as measured by the visual experiment in Example 1, which was 0.29+/−0.09 mm/hr. In that experiment the sample was bound between two glass slides and the convection of liquid around the sample may have been restricted because of the shielding effect of the glass microscope slides which may have interfered with motion of dissolution liquid near the dosage form, which may help to account for the front velocity from that experiment being slightly smaller.

All of the data presented so far in this Example were obtained for 3-D release (release from all surfaces) from flat-ended cylindrical dosage forms.

Next, some baseline experiments and rate constant determinations are presented using uniform-composition cylindrical dosage forms that were radial-release rather than 3-D release. Radial-release means that the ends of the cylindrical dosage forms were prevented from contacting the dissolution fluid. This resulted in a situation in which erosion/degradation was one-dimensional in a cylindrical coordinate system. In some cases the dosage forms for these experiments were made by tablet-pressing a uniform-concentration API-containing dosage form and then physically attaching separately made erosion-resistant end caps. In other cases the dosage forms were made by making an entire dosage form integrally by 3DP, comprising a uniform-composition API-containing portion sandwiched by erosion-resistant end caps. For the dosage forms made by compression which then had end caps attached to them, conventional diclofenac sodium dosage forms were pressed containing varying concentrations of diclofenac sodium in the powder systems of 70:30 and 80:20 (Lactose:HPMC). This set of data included varying API concentration, a variable which was not included in the 3-D release data of Table 2 and FIGS. 16 and 17. Ten dosage forms, all approximately 3 mm tall and 11.15 mm in diameter, were pressed using a pressure of 15000 psi. End caps were then fabricated by pressing 100 mg of pure HPMC powder. These end caps, being made of HPMC with no lactose, were much less permeable or erodible than the portion of the dosage forms made of the Lactose:HPMC mixture. The end caps were then slightly wetted on one side with water and adhered to the tops and bottoms of the pressed API-containing dosage forms to form ensembles. The ensembles were then allowed to dry for 30 minutes at 35° C. in a drying oven (VWR). The ensembles were then tested using the USP dissolution basket method in simulated intestinal fluid of pH 7.4 at 37° C. with a speed of 100 rotations/minute for 6 hours. It was observed that during the testing, the caps stayed in place and erosion or degradation occurred only from the curved cylindrical surfaces of the samples, not from the ends. The fraction of API released over time was then modeled with the Hopfenberg equation (Eq. 2) for infinite cylinders to obtain radial erosion/degradation/release rate constants, $k_r$. The best-fit erosion/degradation/release rate constants thus obtained are plotted in FIG. 18 as a function of the concentration of diclofenac sodium for each of five diclofenac sodium concentrations for each of the two powder systems. For any given powder system, the erosion constants obtained from the Hopfenberg equation (Eq. 2) seem to scale linearly with the concentration of diclofenac sodium. These constants are labeled $k_r$, because they were obtained for a situation in which degradation was limited to the radial direction.

80% Lactose: 20% HPMC: $k_r$(mg/hr cm$^2$)=22.127 ($C_{diclo}$)+2.0481 (Eq. 12)

70% Lactose: 30% HPMC: $k_r$(mg/hr cm$^2$)=7.4647 ($C_{diclo}$)+0.9216 (Eq. 13)

In these experiments, the direction of release was radial, and the concentration of diclofenac sodium was uniform everywhere within the dosage form except that it was of course zero in the end caps. Rate constants obtained through all of these described experiments were later used in mathematical models in later Examples to predict the release profile of dosage forms.

Data were also taken, as a baseline case, of radial release of similar constant-concentration dosage forms that were made by a different technique. These dosage forms were made by 3DP followed by compression, rather than by separate tablet pressing of the body and the end caps followed by a joining. This involved making dosage forms (by 3DP) having end caps to prevent erosion at the end surfaces. The end caps were made of pure HPMC powder which was printed on by a 3DP binder substance which was 3% Eudragit L100 in ethanol. The API-containing central portion of the dosage form was made of powder of 70 wt % Lactose (53-74 micrometers): 30 wt % HPMC K4M (53-74 micrometers) and had a constant uniform diclofenac sodium distribution and an overall loading of 44.1 mg of diclofenac sodium. Switching of powder composition between the end caps and the central portion of the dosage form was achieved by physically changing the powder which was spread to form a particular layer, i.e., removing one powder from the spreading mechanism and replacing it with another. The API concentration and dimensions for the API-containing portion of these dosage forms are given in Table 3.

TABLE 3

Constant uniform API distribution for dosage form with 70:30 Lactose:HPMC and diclofenac sodium

| Region | Radius (mm) | Volume (mm$^3$) | # Times saturated | Concentration of API (mg/mm$^3$) | Loading (mg) |
|---|---|---|---|---|---|
| 1 | 0.521 | 411.03 | 1X | 0.099 | 44.1 |
| Total | | | | | 44.1 mg |

Figure 19:
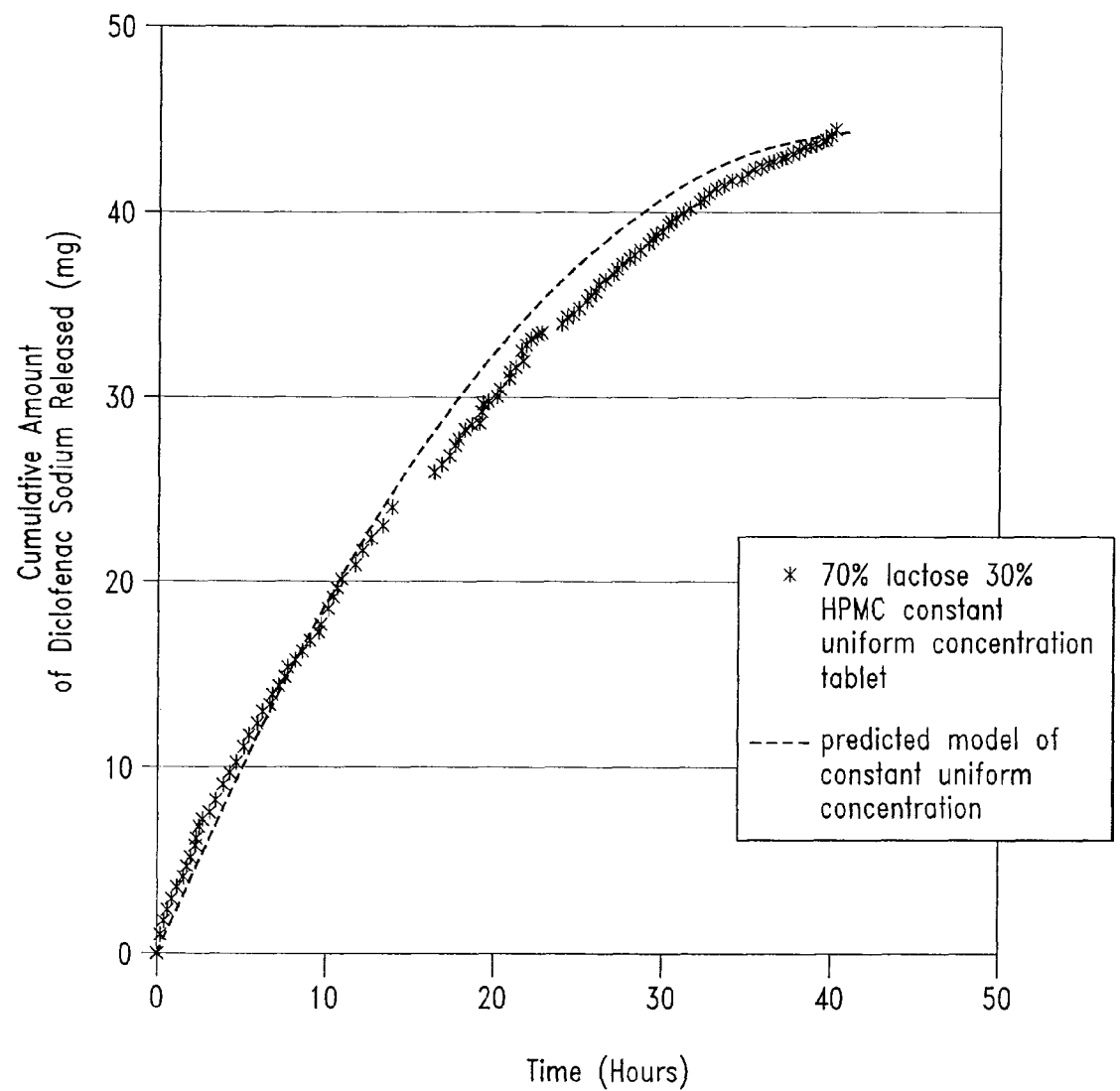
FIG. 19 graphically illustrates for one concentration of diclofenac sodium, a comparison between the measured release profile and the release profile predicted by a model with a best-fit rate constant, for a radial-release geometry in accordance with principles of the present invention.

In this case also, the API release as a function of time was measured and compared to predictions from the model. FIG. 19 shows the release results for this set of dosage forms. The data in FIG. 19 shows a typical non-zero-order release profile. The release rate decreases as time progresses, due to the decrease in volume of API released per unit time, which is due to the decreasing surface area as the erosion or degradation front progresses into the dosage form. In FIG. 19, the data is compared to the Hopfenberg model for release from an infinite cylinder of constant uniform API distribution (Equation 2) using a rate constant determined for best fit. Similar to what was observed in FIG. 17, there was good agreement between measurement and model.

It can be seen in both FIG. 17 and FIG. 19 that although the release profile starts out approximately linear, in the later part of the release there is a definite curving-over of the release profile (slowing down of the release rate). This curvature of the release profile is the feature that is not desired for zero-order release applications.

Example 3

Approximately Zero-Order Release Dosage Forms by Radial Release

In this Example, cylindrical dosage forms were produced having an API concentration that stepwise approximated a concentration that was proportional to $1/r^2$ (r being the distance from the central axis of the cylindrical dosage form). This distribution is not exactly the theoretically suggested distribution for achieving zero-order release, but it is how the particular dosage form was manufactured, and this particular distribution does achieve a fairly high loading of drug, compared to a strictly $1/r$ distribution. This distribution of API was approximated by defining, in a cross-section perpendicular to the cylindrical axis of the dosage form, five concentric circles with corresponding radii to establish five concentration regions as shown in FIGS. 6A and 6B. The outer four regions were annular, and the innermost region was circular. These five concentric regions constituted printed areas within any individual printed layer in the 3DP process, and the pattern was repeated identically for a number of layers in the build direction. The API concentrations in individual regions were chosen to be integer multiples of the API concentration in the outermost region. This allowed the variation of API concentration to be achieved by choosing the number of times a particular region was printed (repetitively) at a fixed dispensing rate from a single dispenser with a single fluid source. (This integer-multiple pattern is not, however, a necessary limitation.)

In manufacturing these dosage forms, the first print pass deposited API-containing binder liquid into the entire interior of the largest circle, meaning it deposited API-containing binder liquid into all of the regions. The second print pass further deposited API-containing binder liquid into the entire interior of the second largest circle, meaning it deposited API-containing binder liquid into the second, third, fourth and fifth regions. The third pass deposited API-containing binder liquid into the entire interior of the third circle, meaning it deposited API-containing binder liquid into the third, fourth and fifth regions. The fourth pass deposited API-containing binder liquid into the entire interior of the fourth circle, meaning it API-containing binder liquid into the fourth and fifth regions. Finally, the fifth pass deposited API-containing binder liquid into the fifth circle or fifth region. The order of deposition could of course have been reversed. The result of this printing operation was a printed powder layer in which the centermost and smallest circular region was printed 5 times, and had a concentration that was 5 times as great as the concentration in the outermost and largest circular region, and other regions had API concentrations which were other integer multiples (respectively, 4, 3, 2 and 1) of the concentration in the outermost region. This two dimensional pattern is illustrated in FIGS. 6A and 6B.

Top and bottom end cap portions were also printed. The top and bottom end caps were made so as to be low permeability with slow erosion rate, containing no API, and were constructed so as to prevent API release from the end surfaces of the dosage form. The portion of the dosage form between the end caps had the above-described five concentration regions to allow radial release from the lateral surface of the cylindrical dosage form. The entire dosage form is shown in FIG. 7. This dosage form was designed to release API radially from the portion between the end caps, but not through the end caps, thus allowing the dosage form to be modeled by Equation 2 (the Hopfenberg model) for an infinite cylinder.

The end caps were printed using a 3 wt % L100 in ethanol solution printed onto powder layers which were composed entirely of 100% high viscosity blend HPMC K4M powder, in the size range 74-106 micrometers. The saturation parameter used for printing the end caps was 1.2. These end caps were essentially impermeable in water. (In a separate experiment, similar discs pressed from 100% HPMC took weeks to swell and/or erode.) At the time of three-dimensional printing, each of the end caps was 4 layers tall with a 300-micrometer thickness of each individual layer used in 3DP. The API-containing portion was printed onto 32 layers of Lactose/HPMC powder of the same layer thickness (300 microns). In the finished product after compression, all dimensions in the direction of compression were shrunk by an expected factor due to compression. Typically, post-compression dimensions in the axial direction were approximately 55% of pre-compression dimensions in the axial dimension. The printing of the end caps actually required changing the powder that was spread. The powder spread for the lowest portion of the print job, which included making the lower end cap, was pure HPMC. Then the powder was changed to the Lactose/HPMC mixture for making the API-containing central portion. Then the powder was changed again, back to pure HPMC, to print the top end cap.

Two sets of these dosage forms were fabricated, differing in the composition of the powder used for making the central (API-containing) portion. One set was fabricated with a center portion composed of powder of 80% Lactose (53-74 micrometers): 20 wt % HPMC K4M (53-74 micrometers) and had a total diclofenac sodium content of 101.8 mg distributed radially in the five concentration regions. Another set was fabricated with a center portion composed of powder of 70% Lactose (53-74 micrometers): 30 wt % HPMC K4M (53-74 micrometers) and had a total diclofenac sodium content of 100.7 mg distributed radially in the five concentration regions. In each case the distribution of API concentration as a function of radius was as given in FIG. 6B. The distribution of diclofenac sodium in these dosage forms is also given in Table 4 and Table 5.

All of the dosage forms were allowed to dry for a minimum of 48 hours in a nitrogen glove box and then were pressed in an 11 mm inside diameter die to a pressure of 15000 psi. The resulting dosage forms had outside diameters of 11 mm and cap thicknesses of 1.21 mm and center portions (API-containing portions) having a height of 4.82 mm. The printing parameters for the API-containing portions of the above dosage forms are listed in the last Example herein.

TABLE 4

API Distribution as a Function of Radius for Dosage Forms Made Using 80:20 Lactose:HPMC

| Region | Outer radius (mm) | Inner radius (mm) | Volume (mm³) | # Times saturated | Concentration of API (mg/mm³) | Loading (mg) |
|---|---|---|---|---|---|---|
| 1 | 5.21 | 3.68 | 205.96 | 1X | 0.108 | 22.34 |
| 2 | 3.68 | 3.01 | 67.87 | 2X | 0.217 | 14.72 |
| 3 | 3.01 | 2.61 | 34.04 | 3X | 0.325 | 11.08 |
| 4 | 2.61 | 2.33 | 20.95 | 4X | 0.434 | 9.09 |
| 5 | 2.33 | — | 82.21 | 5X | 0.542 | 44.58 |
| Total | | | | | | 101.8 mg |

TABLE 5

API Distribution as a Function of Radius for Dosage Forms Made Using 70:30 Lactose:HPMC

| Region | Outer radius (mm) | Inner radius (mm) | Volume (mm³) | # Times saturated | Concentration of API (mg/mm³) | Loading of API (mg) |
|---|---|---|---|---|---|---|
| 1 | 5.21 | 3.68 | 205.96 | 1X | 0.107 | 22.1 |
| 2 | 3.68 | 3.01 | 67.87 | 2X | 0.215 | 14.56 |
| 3 | 3.01 | 2.61 | 34.04 | 3X | 0.322 | 10.96 |
| 4 | 2.61 | 2.33 | 20.95 | 4X | 0.429 | 8.99 |
| 5 | 2.33 | — | 82.21 | 5X | 0.536 | 44.10 |
| Total | | | | | | 100.7 mg |

For testing to determine release profiles, the dosage forms represented in Tables 4 and 5 were dissolved in 1000 mL of phosphate buffer solution, pH 7.4, at 37° C. in a USP dissolution apparatus (Logan Instruments D400) using the USP Type I basket method at 100 rotations/minute. UV absorbance was measured on a sample drawn from the bath by a recirculating sampling apparatus at a wavelength of 275 nm, which was the peak absorbance wavelength for diclofenac sodium. The UV absorbance was referenced to the absorbance of 100 mg of diclofenac sodium dissolved in 1000 mL of the buffer solution.

Figure 18:
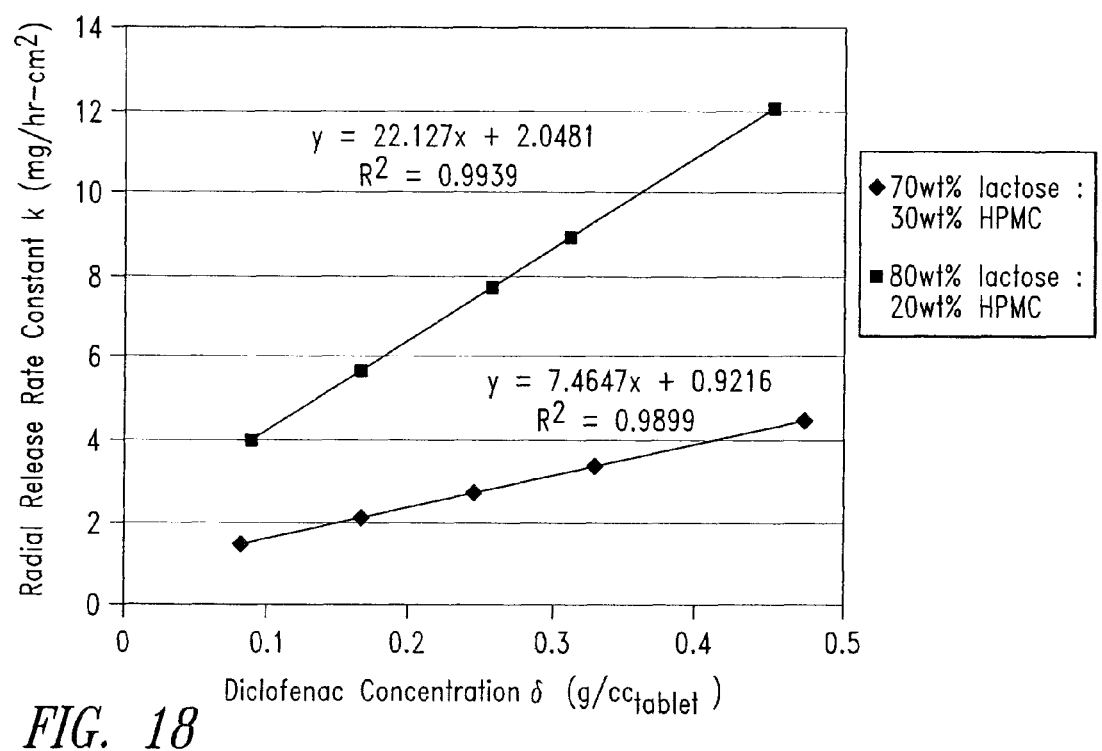
FIG. 18 graphically illustrates release rate constants for radial erosion or degradation as a function of the concentration of diclofenac sodium in the dosage form.

For modeling purposes, to create a modeling prediction to compare with experimental data, the linear dependence of radial erosion rate constant on diclofenac sodium concentration, presented in FIG. 18 in Example 2, was used to approximate erosion/degradation/release rate constants for each of the five concentration regions of these radial distribution dosage forms. The erosion rate constants used for the five regions are given in Table 6 (for the 80:20 composition of the bulk material used in making the dosage form) and Table 7 (for the 70:30 composition).

TABLE 6

Erosion rate constants used in modeling the five concentration regions in the 80:20 Radial-Release dosage forms

| Region | $C_{diclo}$ (mg/mm³) | $k_r$ (from Eq. 12) |
|---|---|---|
| 1 | 0.108 | 4.26 |
| 2 | 0.217 | 6.47 |
| 3 | 0.325 | 8.68 |
| 4 | 0.434 | 10.90 |
| 5 | 0.542 | 13.11 |

TABLE 7

Erosion rate constants for the five concentration regions in the 70:30 Radial-Release dosage forms

| Region | $C_{diclo}$ (mg/mm³) | $k_r$ (from eq. 6.16) |
|---|---|---|
| 1 | 0.107 | 1.67 |
| 2 | 0.215 | 2.41 |
| 3 | 0.322 | 3.16 |
| 4 | 0.429 | 3.91 |
| 5 | 0.536 | 4.65 |

Using these constants and the dosage form dimensions, the predicted release profile was calculated as a composite of several individual release curves, with each individual release curve describing the release from an infinite cylinder in a particular concentration region. The release curves were combined together such that the appropriate concentration and erosion rate constants were used at the appropriate radial locations. It can be understood in the below equation that the times t refer to the time when a particular region was actively releasing, as defined by the radius, and the times used in individual terms of the equation are the times during which that region is releasing API.

The API release predicted according to the model was calculated using the following equation.

$$\frac{Q}{Q_{TOTAL}} = 1 - \left(1 - \frac{k_{r,region1}t}{C_{region1}r_1}\right)^2\Big|_{r_1}^{r_2} + 1 - \left(1 - \frac{k_{r,region2}t}{C_{region2}r_2}\right)^2\Big|_{r_2}^{r_3} + 1 - \left(1 - \frac{k_{r,region3}t}{C_{region3}r_3}\right)^2\Big|_{r_3}^{r_4} + 1 - \left(1 - \frac{k_{r,region4}t}{C_{region4}r_4}\right)^2\Big|_{r_4}^{r_5} + 1 - \left(1 - \frac{k_{r,region5}t}{C_{region5}r_5}\right)^2$$

Figure 20:
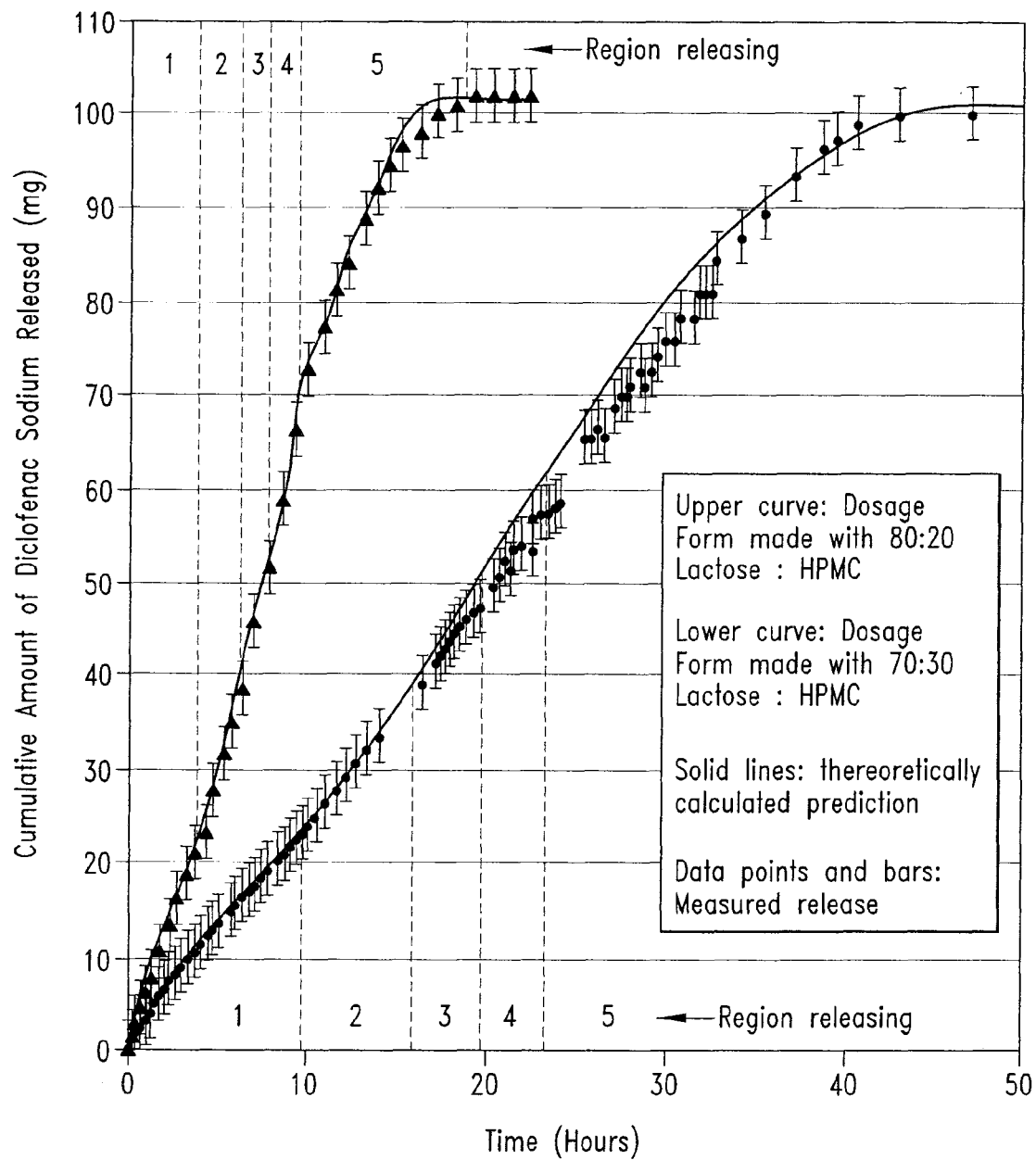
FIG. 20 graphically illustrates measured and predicted release profiles of diclofenac sodium for radial-release cylindrical dosage forms having the design of FIGS. 6A, 6B and 7, for two different compositions of the bulk material of the dosage form, in accordance with principles of the present invention.

FIG. 20 shows both the experimental dissolution results and the predictions of the model for these sets of dosage forms. The agreement between model and experiment is very close, which supports the use of the flowchart procedures of FIGS. 12 and 13 for designing controlled release dosage forms to achieve specific desired release profiles.

A linear regression instead of a time-dependent prediction of a model, illustrates that fit to that portion of the experimental data is nearly linear. For this fit, the bending-over portion of the release profile in the latest portion of the release profile was omitted. The fit for the 80:20 dosage form shows a release rate, for the 1-15 hours portion of the curve, of approximately 6.8 mg/hr. After 15 hours, the release tails off due to the constant concentration and decreasing surface area of the innermost region of the dosage form. The fit for the 70:30 dosage form shows a release rate, for the 1-36 hours portion of the curve, of approximately 2.5 mg/hr. After 36 hours the release also tails off for this dosage form for the same reasons. Typically the mouth-to-exit transit time in an adult human is 35 hours for approximately 50% of the population, and about 10% have transit times shorter than 20 hours. The releases obtained in these two samples are of the appropriate time scales for such use. The overall time scale of the release profile has been shown in an earlier Example herein to depend on the proportion of lactose adjuvant present in the powder, and so the release rate could easily be adjusted to achieve faster or slower release rates.

The linearity of this release profile over almost all of its duration can be compared with the data presented in FIG. 19 at the end of Example 2, which was radial-release from a dosage form of uniform concentration, which had more of a curving-over (departure from zero-order appearance) in the later part of the release profile. It can be seen that this release profile of the present invention maintains its linearity much better in the later portion of the release, as compared to the results shown in FIG. 19.

The curve for uniform concentration with radial release (FIG. 19) can be compared to the release curves in FIG. 20 for the Radial-Release dosage forms fabricated with radial distributions of diclofenac sodium. The erosion/degradation front enters these samples and encounters higher concentration of diclofenac sodium as the radius decreases in size. The competition between decreasing volume released and increasing concentration in those elements has been balanced in the dosage form design and has resulted in cumulative release that has been nearly linear as a function of time.

The modeled curves in FIG. 20 (from Equation 14) are based on the assumption that the concentration regions are discretely defined. For this reason the predicted curves can be observed to have, in certain places very slight discontinuities of slope. (In order to help in observing this, the times of changing over from one region to another have been indicated in FIG. 20.) However, it can also be observed in the experimental data of FIG. 20 that the release is fairly continuous or monotonic and does not display any discontinuities of slope or other features that might correspond to the discrete steps by which the printing of the dosage form was defined. It is possible that some smoothing-out of API release occurred in the gel layer during dissolution. It is also possible that some smoothing of the concentration distribution in the dosage form occurred during the three-dimensional printing process as a result of bleeding of binder liquid. It is plausible that some migration of binder liquid would occur during the 3DP process, especially between concentration regions. This would result in more diffuse concentration steps, and a more continuously variable concentration gradient within the dosage form. Bleeding of binder liquid can be influenced by controlling the saturation parameter during 3DP, i.e., the ratio which describes how much of the available inter-particle empty space is actually filled by binder liquid.

A continuous gradient would be an improvement of the dosage form in this case, since the theoretically suggested concentration distribution for achieving any smoothly-curved release profile would be a continuously variable concentration distribution. Thus, bleeding of the binder liquid in the powder bed is not necessarily detrimental for this purpose and can be encouraged by an appropriate choice of local saturation parameter during 3DP, such as greater than approximately 1.0. A saturation parameter greater than approximately 1.0 is known to encourage bleeding of binder liquid in the powder, which would tend to smooth the API distribution. Bleeding is also influenced by other factors such as binder liquid evaporation rate.

Example 4

Zero-Order Release from Radial-Release Dosage Forms Having Concentration Varying as 1/r This Example, again, is for a radial-release dosage cylindrical-geometry form, and again, it uses five radially nested regions. However, in this Example the distribution of API concentration is a stepwise approximation of a 1/r distribution, rather than a $1/r^2$ distribution as in the previous Example. A 1/r distribution is the exact theoretically suggested distribution for zero-order release in a radial-release cylindrical geometry. For this example, the concentrations chosen are 1×, 1.5×, 2×, 3× and 4×. However, the radial locations of the boundaries between regions have been chosen appropriately to provide the 1/r distribution. Just as in the previous Example, this Example continues to use the innermost region (region 5) as being fully printed with the highest concentration of API, even though it is known that this results in a slight period of time near the end of the release profile where the release profile departs from linearity.

Figure 21:
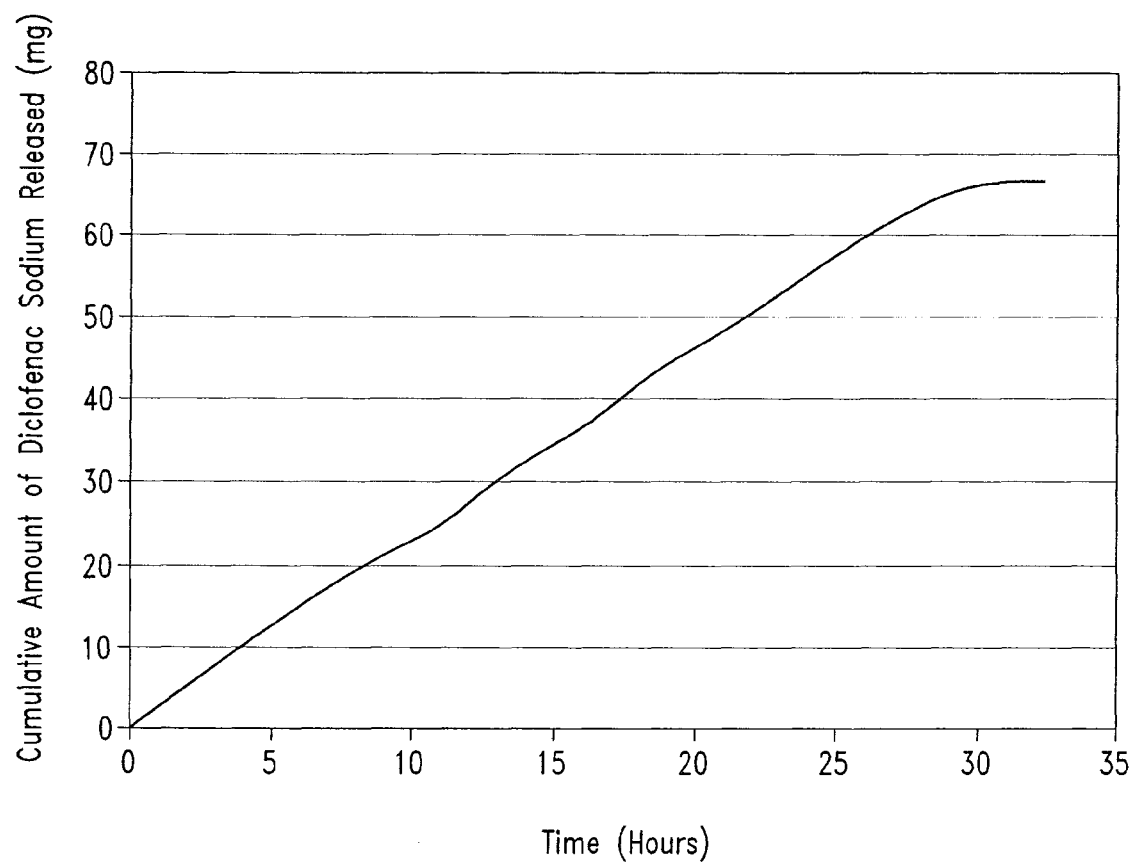
FIG. 21 graphically illustrates the predicted release profile from a radial-release cylindrical dosage form having an API concentration distribution that is a stepwise approximation of a 1/r distribution in accordance with principles of the present invention.

The numerical values defining the concentration regions are given in Table 8. The release profile predicted by the model for this concentration distribution is given in FIG. 21.

TABLE 8

Radial API distribution for 1/r dosage forms

| Region | Outer radius (mm) | Inner radius (mm) | Volume (mm³) | # Times saturated | Concentration of API (mg/mm³) | Loading of API (mg) |
|---|---|---|---|---|---|---|
| 1 | 5.21 | 3.47 | | 1X | 0.107 | 24.43 |
| 2 | 3.47 | 2.61 | | 1.5X | 0.161 | 12.83 |
| 3 | 2.61 | 1.74 | | 2X | 0.214 | 12.22 |
| 4 | 1.74 | 1.30 | | 3X | 0.321 | 6.41 |
| 5 | 1.30 | −0.00 | | 4X | 0.428 | 11.00 |
| Total | | | | | | 66.89 |

Example 5

Zero-Order Release from Radial-Release Dosage Forms Having Concentration Varying as $1/r^2$ and having an inert innermost region This Example uses the same 1/r concentration distribution of API as in Example 4, but it leaves the innermost region free of API. As discussed elsewhere, this is done because in a design such as Example 3 or 4, the innermost region can be expected suffer a substantial decrease of surface area as it erodes or degrades, without being able to have a compensating increase of API concentration, and this results in a departure from zero-order release. The design of this Example, with an inert innermost region, means that the degradation characteristics of the innermost region are irrelevant to the API release profile, and so this design is expected to avoid the slight departure from true zero-order release which in the previous Examples was associated with the erosion of the innermost region. Thus, it is expected to have a release profile that is even closer to truly zero-order release than the release profiles of Example 4.

Figure 22:
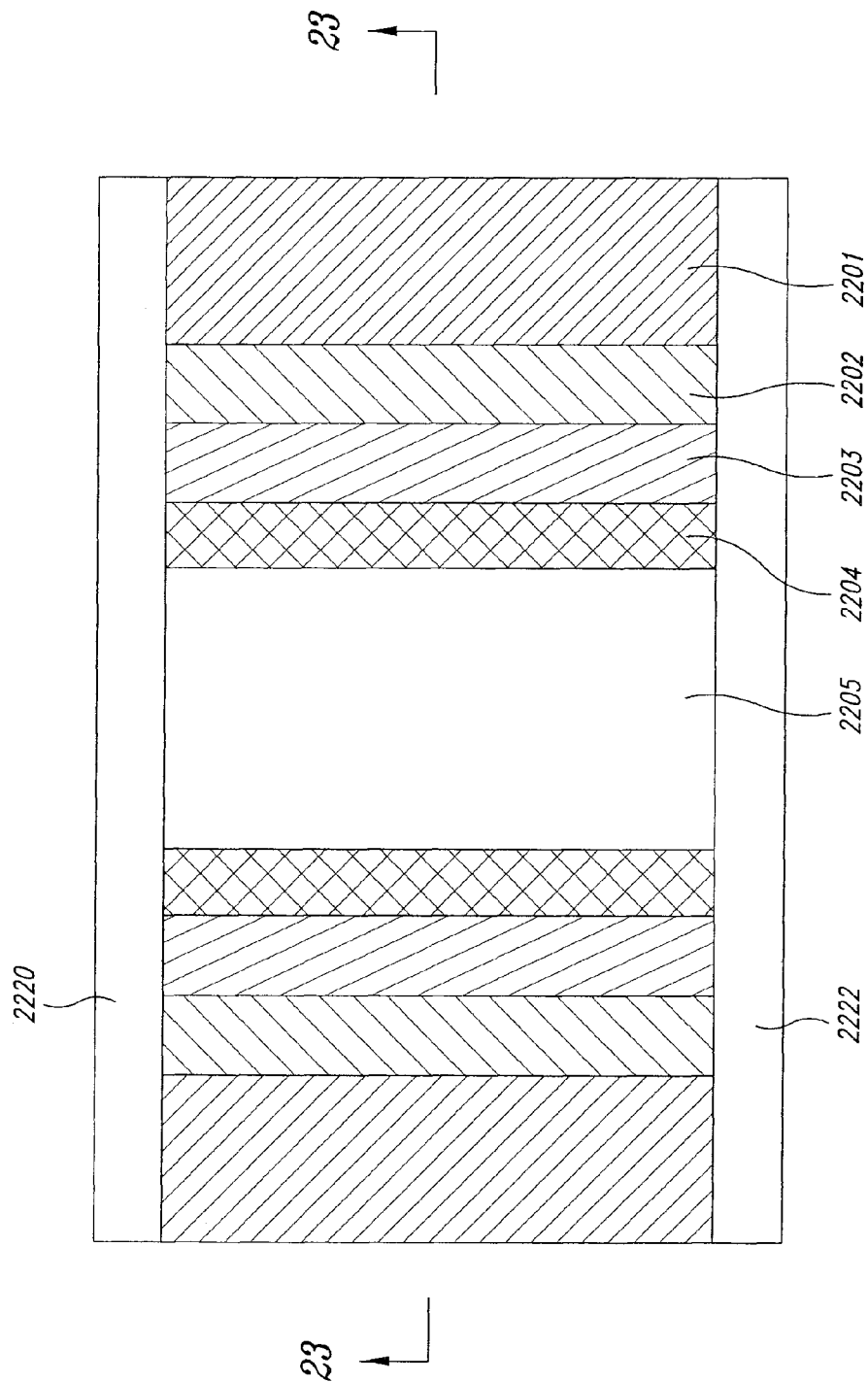
FIG. 22 illustrates the geometric construction of a radial-release cylindrical dosage form having an API concentration distribution which is a stepwise approximation of a 1/r distribution, and which additionally has an inert innermost region in accordance with principles of the present invention.
Figure 23:
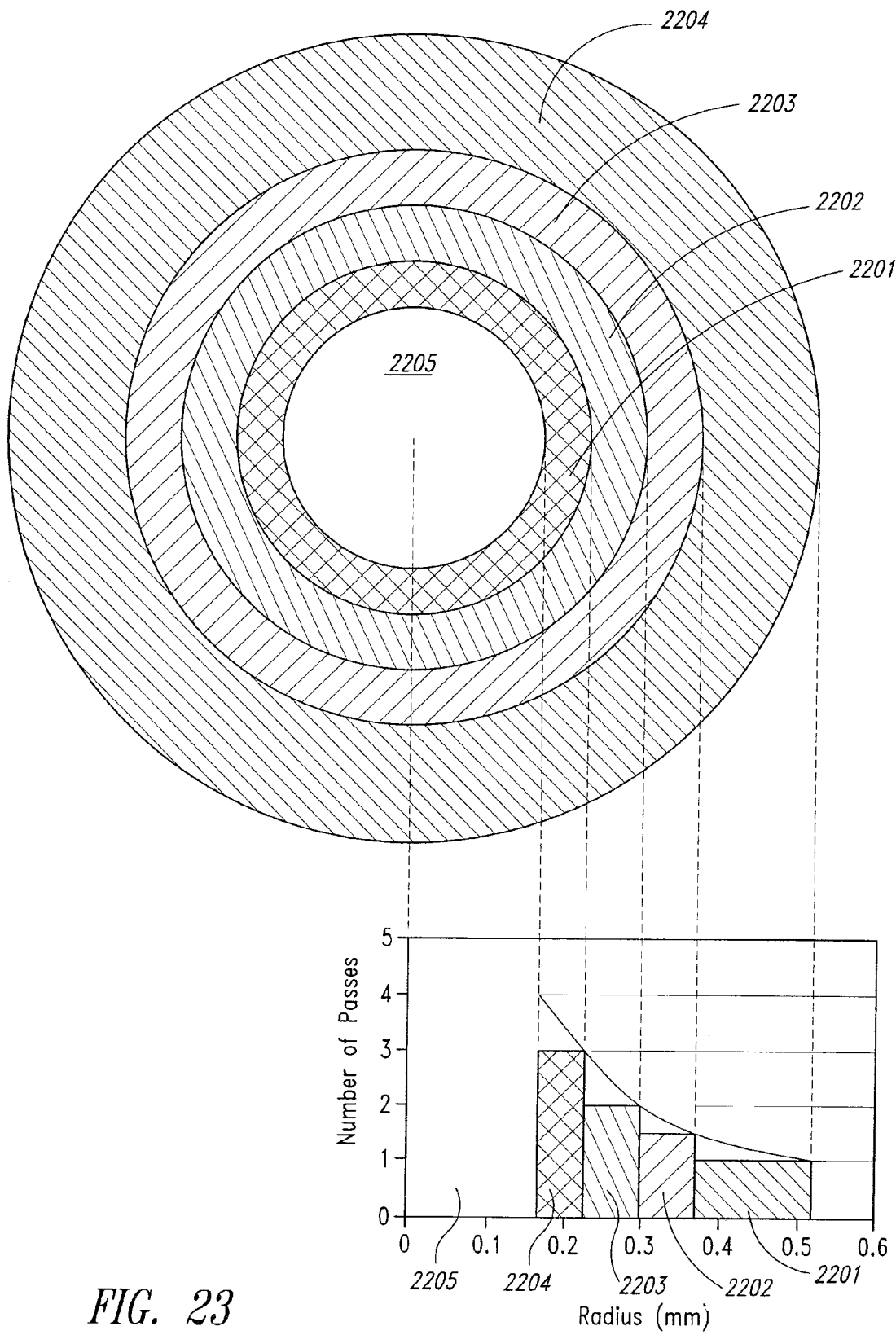
FIG. 23 illustrates the geometric distribution of API concentration of the dosage form of FIG. 22 along line 23-23 in accordance with principles of the present invention.

The numerical values defining the concentration regions are given in Table 9. The distribution of API concentration is illustrated in FIGS. 22 and 23. In FIGS. 22 and 23, the innermost region 2205 is free of API, and the concentric layers expanding outward 2204, 2203, 2202, 2201 contain varying concentrations of API in order to produce a zero-order release profile. FIG. 22 illustrates a dosage form with a top cap 2220 and a bottom cap 2222. As a result of leaving the innermost region free of API, the total amount of API that is contained in this dosage form is less than what was contained in the previous Example. However, the linearity of release is expected to be better than what is available from the designs of previous Examples. The release profile predicted by the model for this concentration distribution is given in FIG. 24.

TABLE 9

Radial API Distribution for 1/r Dosage Forms With Inert Center Region

| Region | Outer radius (mm) | Inner radius (mm) | Volume (mm³) | # Times saturated | Concentration of API (mg/mm³) | Loading of API (mg) |
|---|---|---|---|---|---|---|
| 1 | 5.21 | 3.47 | | 1X | 0.108 | 24.43 |
| 2 | 3.47 | 2.61 | | 1.5X | 0.161 | 12.83 |
| 3 | 2.61 | 1.74 | | 2X | 0.214 | 12.22 |
| 4 | 1.74 | 1.30 | | 4X | 0.321 | 6.41 |
| 5 | 1.30 | — | | 0X | 0.000 | 0.00 |
| Total | | | | | | 55.92 |

Of course, such an inert innermost region could also be used with a dosage form design having a 1/r distribution.

Example 6

Zero-Order Release from Cylindrical Dosage Forms with Release on all Surfaces (3-D Release)

The dosage form of this Example is cylindrical but allows erosion or degradation of all surfaces, rather than shielding certain surfaces with end caps as in preceding Examples. The geometry and concentration distribution of the dosage form of this Example are shown in FIG. 25.

It is assumed that the surface erosion rates in the radial and vertical directions are constant and equal to each other. During every time interval, $\Delta t$, during erosion/degradation, the erosion front moves a distance, $\Delta I$, into the dosage form. As erosion/degradation continues, the surface area, $A$, of this erosion/degradation front decreases and the volume elements, $A\Delta I$, also decrease over time. The incremental API release from any given element during a given time increment is $C*A*\Delta I$ where C is the API concentration in that element. In order to achieve a constant release rate, the amount of API released in one element must equal the amount of API released from all subsequent elements, or $$C_o A_o = C_1 A_1 = C_2 A_2 = C_3 A_3 \ldots = C_n A_n \quad (6.14)$$

Figure 24:
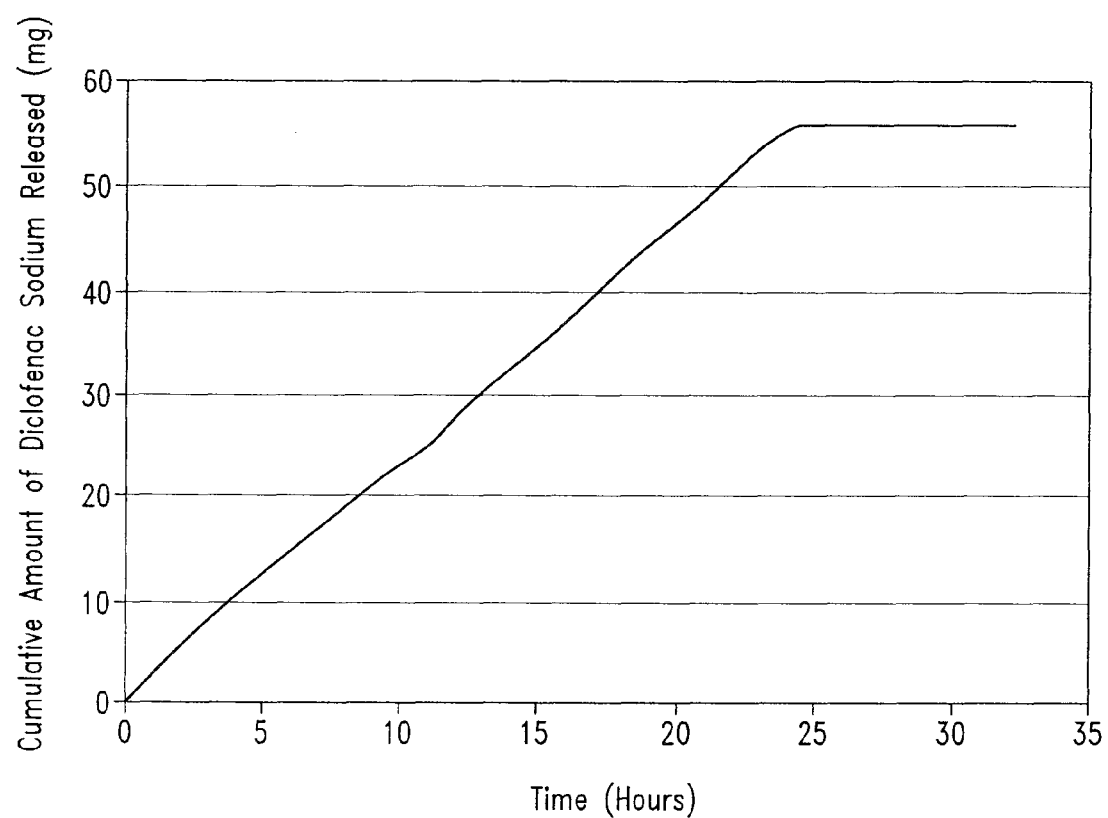
FIG. 24 graphically illustrates the predicted release profile from the dosage form illustrated in FIGS. 22 and 23 in accordance with principles of the present invention.

This criterion for zero-order release from flat-ended cylinders was used to design dosage forms for fabrication by 3DP. The API concentrations in individual regions were chosen to be integer multiples of the API concentration in the outermost region. This allowed the variation of API concentration to be achieved by the number of times a particular region was printed (repetitively). Five concentration sections, $C_1$, $C_2=2C_1$, $C_3=3C_1$, $C_4=4C_1$, and $C_5=5C_1$, were used to define the printed API distribution for 3D-Release Zero-order dosage forms. The fact that these concentrations were integer multiples of the smallest concentration meant that the dosage form could be printed by varying the number of print passes used in a given region in any given layer. The dimensions of individual regions were determined by starting with a dosage form's outer dimensions and surface area, $A_1$, and the concentration obtained from one print pass, $C_1$, and solving for $A_2$ through $A_5$ according to the relation $C_1A_1=C_2A_2=C_3A_3=C_4A_4=C_5A_5$, where the A's are the exposed surface area of an individual region counting all exposed surfaces. The radial and axial dimensions of the individual regions were found by assuming that the surface erosion rates were equal in the radial and vertical directions. The ideal axial dimensions were then modified slightly to take into account the discrete layer thicknesses of the three-dimensional printing process. The radial dimensions were modified to take into account the discrete line-to-line and drop-to-drop spacing of the three-dimensional printing process and also the consideration of equaling the spacing in the axial direction which was governed by powder layer thickness. Table 10 gives the radial dimensions, axial dimensions, and relative API concentrations of each of the regions used for 3DP fabrication of dosage forms, with height dimension referring to the height after compression. The line-to-line spacing used was 120 micrometers and the layer height used during three-dimensional printing was 305 micrometers. Dimensions after compression of the dosage form were shrunken in the direction of compression by an expected amount that was calculated into the design. FIG. 24 shows a schematic of the vertical cross section of a 3D-Release Zero-order dosage form. FIG. 24 includes dashed lines indicating the individual powder layers used in the 3DP printing of this dosage form.

TABLE 10

Concentration, radii, and heights of concentration regions in 3D-Release Zero-order Dosage forms

| Region | Concentration | Outer radius (mm) | Outer height (mm) |
|---|---|---|---|
| 1 | $C_1$ | 5.28 | 4.37 |
| 2 | $2C_1$ | 3.72 | 3.20 |
| 3 | $3C_1$ | 3.00 | 2.59 |
| 4 | $4C_1$ | 2.64 | 2.28 |
| 5 | $5C_1$ | 2.4 | 1.98 |

The printed API solution was 18.0 wt % diclofenac sodium/1 wt % PVP, and 81-wt % methanol. The powder consisted of 70 wt % lactose and 30-wt % HPMC K4M. A total of 31 layers were printed with layer thickness of 305 micrometers for an overall dosage form height of ~9.2 mm (before compression). The printing parameters used during the fabrication are given in the last Example. Dosage forms were allowed to dry for 36 hours in a nitrogen glove box, and were then pressed at 15000 psi in an 11 mm diameter tablet die to an average of 4.37+/−0.03 mm in height. Table 11 gives the concentrations and dosages printed into each of the five regions. The overall loading of diclofenac sodium printed into each dosage form was 71.65 milligrams.

TABLE 11

3D-Release Zero-Order Dosage Forms: Printed API Distribution

| Section | Volume (mm$^3$) | Concentration (mg/mm$^3$) | Loading (mg) |
|---|---|---|---|
| 1 | 256.23 | 0.110 | 28.19 |
| 2 | 60.63 | 0.220 | 13.34 |
| 3 | 21.21 | 0.330 | 6.99 |
| 4 | 13.07 | 0.440 | 5.75 |
| 5 | 31.59 | 0.550 | 17.38 |
| Total | | | 71.65 mg |

Figure 26:
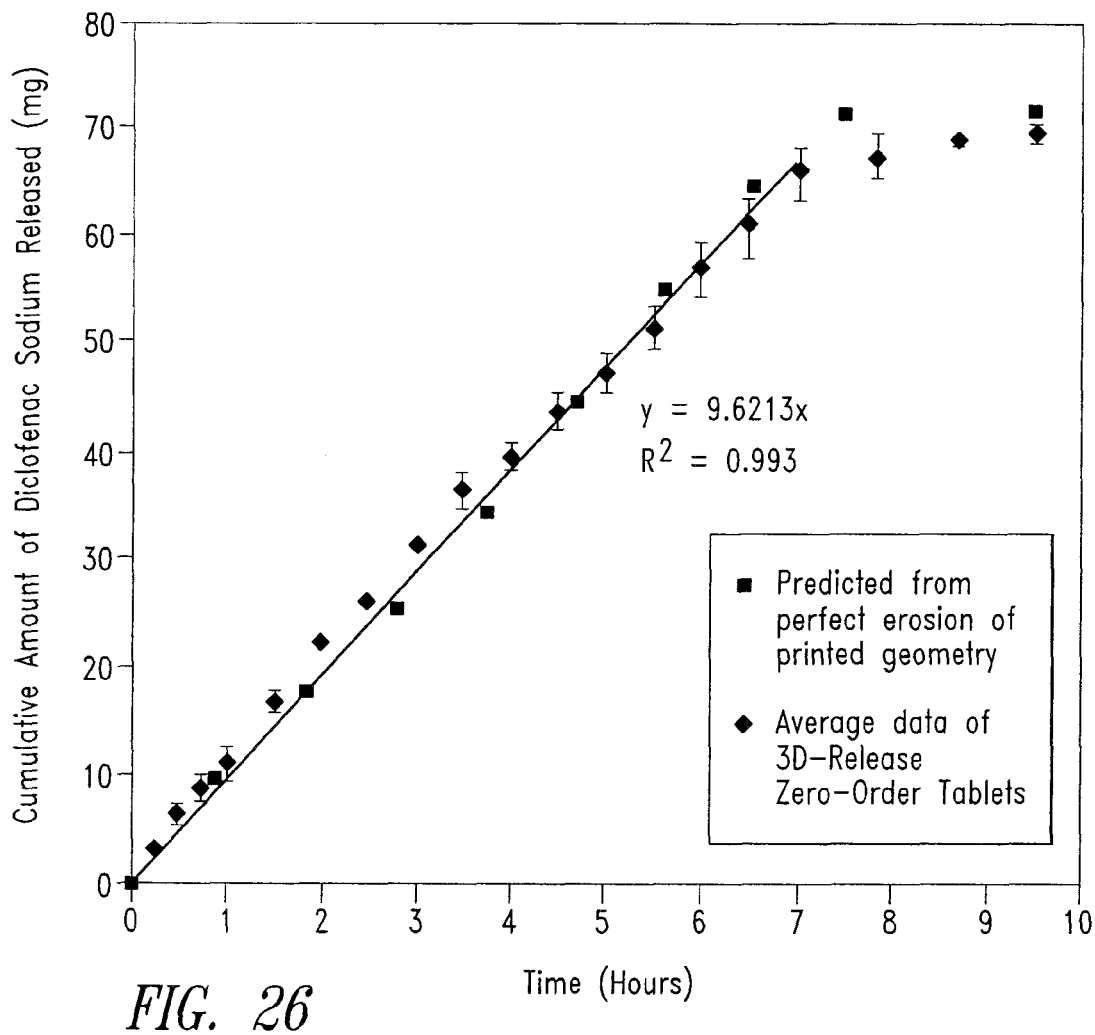
FIG. 26 graphically illustrates the measured and predicted release of diclofenac sodium from the 3D-release dosage form of FIG. 25 as a function of time in accordance with principles of the present invention.

Two 3D-Release Zero-order dosage forms, represented in Table 6.8, were dissolved in 1000 mL of phosphate buffer solution, pH 7.4, at 37° C. in a USP Type I dissolution apparatus (Logan Instruments D400) using the USP I basket method at 100 rotations/minute. UV absorbance measurements were taken as a function of time at a wavelength of 275 nm, which is the peak absorbance wavelength for diclofenac sodium. FIG. 26 shows the cumulative release of diclofenac sodium from the 3D-Release Zero-order dosage forms as a function of time. The results of the dissolution showed that the dosage forms released over a 10-hour period. The cumulative API release measured in the contents of the bath, 68.7 mg, agreed to within 2.6% with the predicted overall dosage of 71.65 mg determined from printing parameters. FIG. 26 also shows the predicted release profile calculated assuming perfect erosion of the dosage form design from all of the surfaces with a surface erosion or recession rate of 0.32 mm/hr.

These dosage forms were able to achieve approximately zero-order release over a period of approximately 8 hours without the use of end-caps or membranes. An essentially constant release rate of 9.62 mg/hour was measured as the release rate of diclofenac sodium from dosage form geometry releasing from all three surfaces of the dosage form. The release data correlates well with the predicted release from a dosage form undergoing perfect erosion at 0.32 mm/hr with the concentration distribution given in Table 11.

It is likely that in the dosage form described and dimensioned in this example, there was not simultaneous extinction of particular walls in the radial direction and in the axial direction. It would also be possible to design 3-D release cylindrical dosage form such that for each respective region, the radial wall thickness of each individual region (except for the innermost region, which does not have a wall thickness) substantially equaled the axial wall thickness of the respective region. This would assure that the degradation front progressed from one region to another in the radial direction at substantially the same time as it progressed from one region to another in the axial direction. A set of dosage form dimensions illustrating this design strategy is illustrated in Table 12:

TABLE 12

Dosage Form Dimensions for Equal Radial Wall Thickness and Axial Wall Thickness

| Region | Concentration | Outer Radius (mm) | Outer Height (mm) |
|---|---|---|---|
| 1 | $C_1$ | 5.28 | 4.37 |
| 2 | $2C_1$ | 4.56 | 2.93 |
| 3 | $3C_1$ | 4.04 | 1.89 |
| 4 | $4C_1$ | 3.67 | 1.15 |
| 5 | $5C_1$ | 3.43 | 0.67 |

Example 7

3-D Release Dosage Forms with Inert Innermost Region

This Example is the same as the previous Example except that the innermost region is left free of API in order to improve the linearity of API release during the very last portion of the release profile. Table 12 gives the concentrations and dosages printed into each of the five regions.

TABLE 13

3D-Release Zero-order Dosage forms with inert innermost region: Printed API Distribution

| Section | Volume (mm$^3$) | Concentration (mg/mm$^3$) | Loading (mg) |
|---|---|---|---|
| 1 | 256.23 | 0.110 | 28.19 |
| 2 | 60.63 | 0.220 | 13.34 |
| 3 | 21.21 | 0.330 | 6.99 |
| 4 | 13.07 | 0.440 | 5.75 |
| 5 | 31.59 | 0.0 | 0 |
| Total | | | 54.27 |

Example 8

Escalating Release Dosage Forms

A dosage form of this Example can use any of the geometries discussed elsewhere herein and can use a stepwise approximation of a desired API concentration distribution as described elsewhere herein. In order to achieve an escalating release, the API concentration distribution, or a stepwise approximation thereof, may increase, as the front progresses closer to the center of the dosage form, more rapidly than a distribution that gives zero-order release that was already described in earlier Examples. For example, in the case of a cylindrical radial-release dosage form, the API concentration may increase more rapidly than 1/r or may be a stepwise approximation of a distribution that increases with decreasing radius more rapidly than a 1/r distribution. It would also be possible to construct a dosage form as just described but with its innermost region containing no API.

Example 9

Decreasing Release Dosage Forms

A dosage form of this Example can use any of the geometries discussed elsewhere herein and can use a stepwise approximation of a desired API concentration distribution. In order to achieve a decreasing release, the API concentration distribution, or a stepwise approximation thereof, may increase, in the direction from the exterior of the dosage form toward the center of the dosage form, less rapidly than a distribution that gives zero-order release. For example, in the case of a cylindrical radial-release dosage form, the API concentration may increase less rapidly than 1/r or may be a stepwise approximation of a distribution that increases with decreasing radius less rapidly than a 1/r distribution. The API concentration distribution may be a distribution that decreases, or may be a stepwise approximation of a distribution that decreases as one goes in the direction from the exterior of the dosage form toward the center of the dosage form. It would also be possible to construct a dosage form as just described but with its innermost region containing no API.

Example 10

Dual-Release Dosage Forms

Using Rate Constants and Surface Degradation Mechanism to Design Dual Release Dosage Forms Fabricated by 3DP It is also possible to construct a dosage form which includes a portion having nested regions similar to what has already been described, and at least one additional non-nested region at least one of which may contain API. It is also possible for at least one of the nested regions to contain no API.

The above information about the surface degradation mechanism and rate constants of the dosage form compositions was used to design dual release dosage forms to be fabricated by 3DP. The ability of these dosage forms to degrade at the surface allows for the design of dosage forms that will release from the exterior of the dosage form inward according to the API distribution profile. 3DP has the ability to fabricate dosage forms with non-uniform API distribution, and therefore the design of dosage forms for complex release is possible.

Two dosage forms were designed to be dual release dosage forms for fabrication by 3DP. The cross-sectional design of these two dosage forms are shown in FIG. 26. The first is a diclofenac sodium dual release dosage form, and the second is a chlorpheniramine maleate dual release dosage form.

These dosage forms were designed with three API-containing regions. The thin top and bottom API-containing regions were one layer tall, and extended the entire diameter of the dosage form, 11 mm. These two regions were designed to release quickly upon initial imbibition and outer surface deterioration. The center concentric region was 14 layers tall, 7 mm in diameter and it was designed for a secondary delayed and controlled release. The dosage form was designed to be 36 layers overall, with a non-uniform API distribution described in Table 14.

TABLE 14

API Distribution Along Vertical Axis in Dual Release Designs

| N | Dosage | Diclofenac sodium Dosage forms (mgs) | Chlorpheniramine maleate Dosage forms (mgs) |
|---|---|---|---|
| 2 layers | — | — | — |
| 1 layer | $N \epsilon \Delta z \delta \pi (0.55 \text{ cm})^2$ | 3.26 | 2.90 |
| 10 layers | — | — | — |
| 14 layers | $N \epsilon \Delta z \delta \pi (0.35 \text{ cm})^2$ | 19.30 | 17.18 |
| 10 layers | — | — | — |
| 1 layer | $N \epsilon \Delta z \delta \pi (0.55 \text{ cm})^2$ | 3.26 | 2.90 |
| 2 layers | — | — | — |

$\epsilon$ represents the compression factor, $\Delta z$ is the layer height, and $C_p$ is the printed concentration in that layer. Table 13 also shows actual dosage forms fabricated with this design, as discussed below for two samples, diclofenac sodium dual release dosage forms and chlorpheniramine maleate dual release dosage forms. For these dosage forms, the compression factor was 0.55, the layer thickness at the time of printing was 200 micrometers, and $\delta$ (diclofenac sodium) was 312 mg/cc and $\delta$ (chlorpheniramine maleate) was 277 mg/cc.

Figure 27:
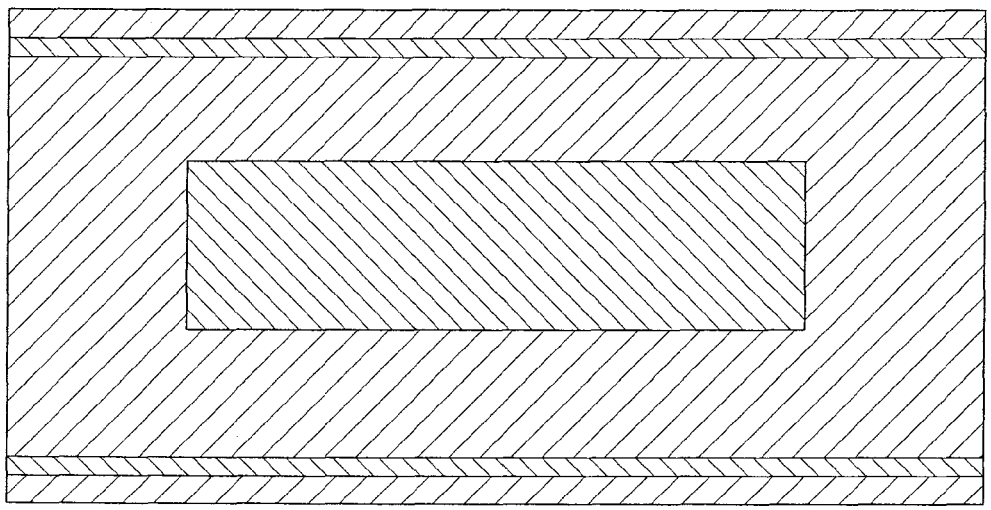
FIG. 27 is a schematic of a dosage form of Example 10 having nested regions and also having API-containing cap-regions that are not nested in accordance with principles of the present invention.

Numerical methods were used to predict theoretical release profiles based on the above design and the erosion rate constants for dosage forms of 70% lactose 30% HPMC for both compounds, and an initial layer thickness of 200 micrometers. The numerical methods used a spreadsheet to iteratively integrate a cylinder of reducing volume using time steps of 0.1 hour. It was assumed that the erosion rates were constant and therefore the degradation front movement into the sample was constant in both the radial and vertical directions. The resulting theoretical release plots, both incremental release vs. time and cumulative release vs. time, for chlorpheniramine maleate dual release dosage forms are shown in FIG. 27. Note that because equal time divisions were used, the incremental release also represents the release rate over time.

Both diclofenac sodium and chlorpheniramine maleate dosage forms were fabricated by 3DP (CJ CD OSP) using 36 layers of 200 micrometer layer thickness. The powder was 70-wt % 53-74 micrometer lactose and 30-wt % 53-74 micrometer HPMC K4M. The binder solution used for both was 5 wt % L100 in ethanol and the API solutions were respectively 18 wt % diclofenac sodium in methanol and 20 wt % chlorpheniramine maleate in 80:20 ethanol:deionized water. Post printed samples were allowed to dry for two days in a nitrogen glove box and then were pressed in a tablet die of 11 mm in inside diameter to final heights of 3.25 (+/−0.04) mm as determined by digital calipers. Table 13 above shows the overall API distribution printed into these dosage forms. The last Example includes the printing parameters for these samples.

Two each of the diclofenac sodium and chlorpheniramine maleate dual release dosage forms were characterized by USP dissolution basket method in simulated intestinal fluid of pH 7.4 at a temperature of 37° C. and basket rotation speed of 100 rotations/minute. The two dissolution profiles for each API were averaged together and were compared with the respective theoretical release profile. The results are shown in FIGS. 28-31.

Each of the release profiles for the diclofenac sodium dosage forms and the chlorpheniramine maleate samples do follow the theoretical release profiles as calculated from each system's respective erosion rate constants such as are found in Example 2. There are three small differences, however, between the empirical and predicted curves in these figures.

Figure 28:
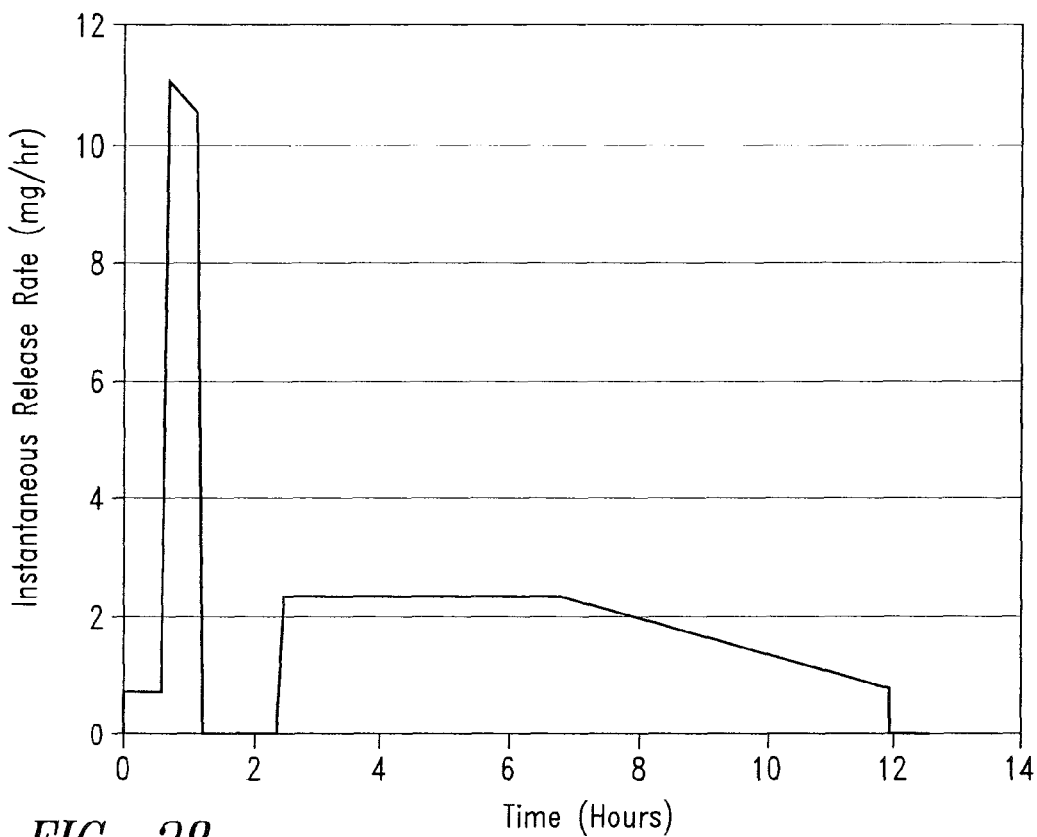
FIG. 28 graphically illustrates a theoretically predicted instantaneous release plot for the dosage form of FIG. 27 containing Chlorpheniramine Maleate in accordance with principles of the present invention.
Figure 30:
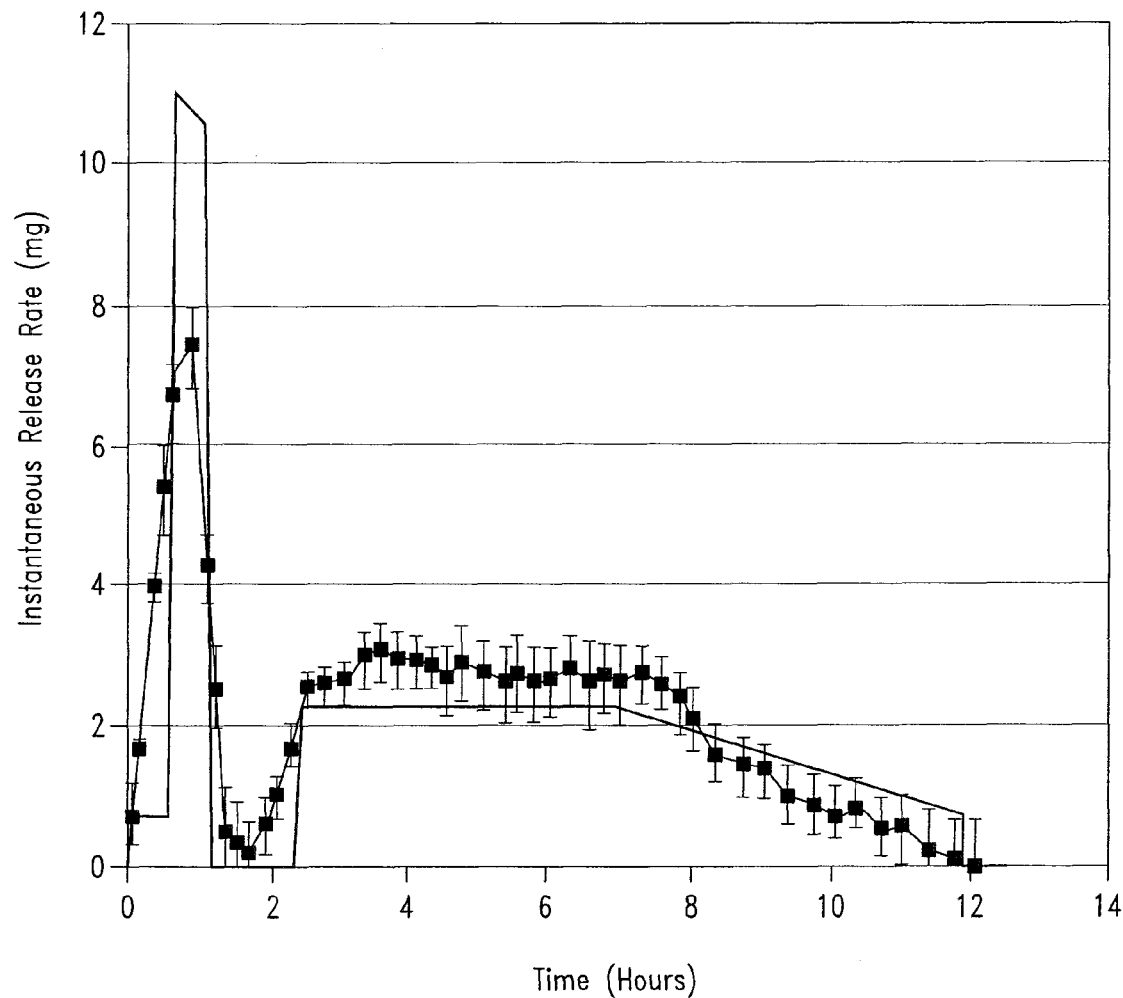
FIG. 30 graphically illustrates both measured and predicted instantaneous release for the dosage form of FIG. 27 containing Chlorpheniramine Maleate in accordance with principles of the present invention.

The first effect that can be seen especially in the incremental release plots, FIGS. 28 and 30, is a burst effect. API was released from the outermost API regions prematurely as the initial gel layer was still being formed. This effect was illustrated in FIG. 15, where the erosion rate was not constant during the first approximately 30 min. of dissolution. The theoretical model assumes constant erosion rate throughout the dosage form, which explains why the theoretical plot shows lower release during the first 30 minutes. The entire first peak is shifted to the left as the API from the top and bottom sections is released sooner than predicted.

The second effect is a broadening of the release peaks. The actual release profiles above do not follow the strict, sharp release profile of the model dosage form. The release peaks are wider, release begins sooner than predicted, and the release tends to end later. This can be partly attributed to API migration in the powder bed during printing. It is known that spatial resolution of articles manufactured by 3DP is limited by capillary effects in the powder bed. Such effects are needed to knit together the finite layers of the printed structure. The theoretical "model" dosage form has been modeled neglecting such effects. It was modeled with a sharp stepped API distribution profile.

Figure 29:
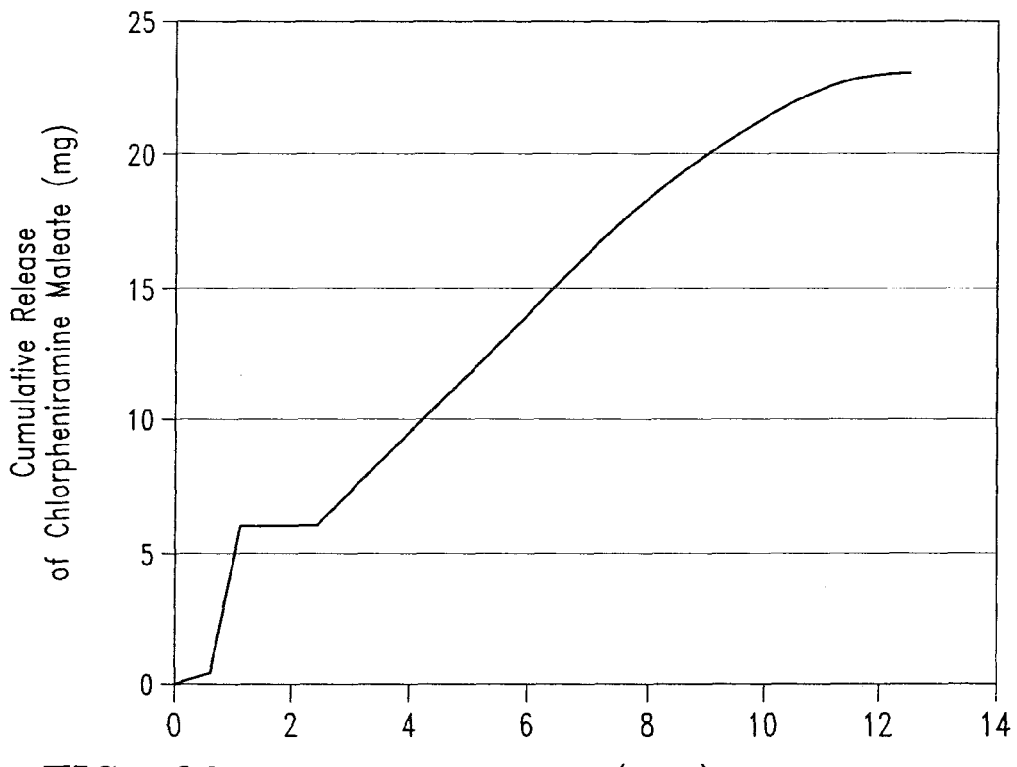
FIG. 29 graphically illustrates the theoretically predicted cumulative release plot for the dosage form of FIG. 27 containing Chlorpheniramine Maleate in accordance with principles of the present invention.
Figure 31:
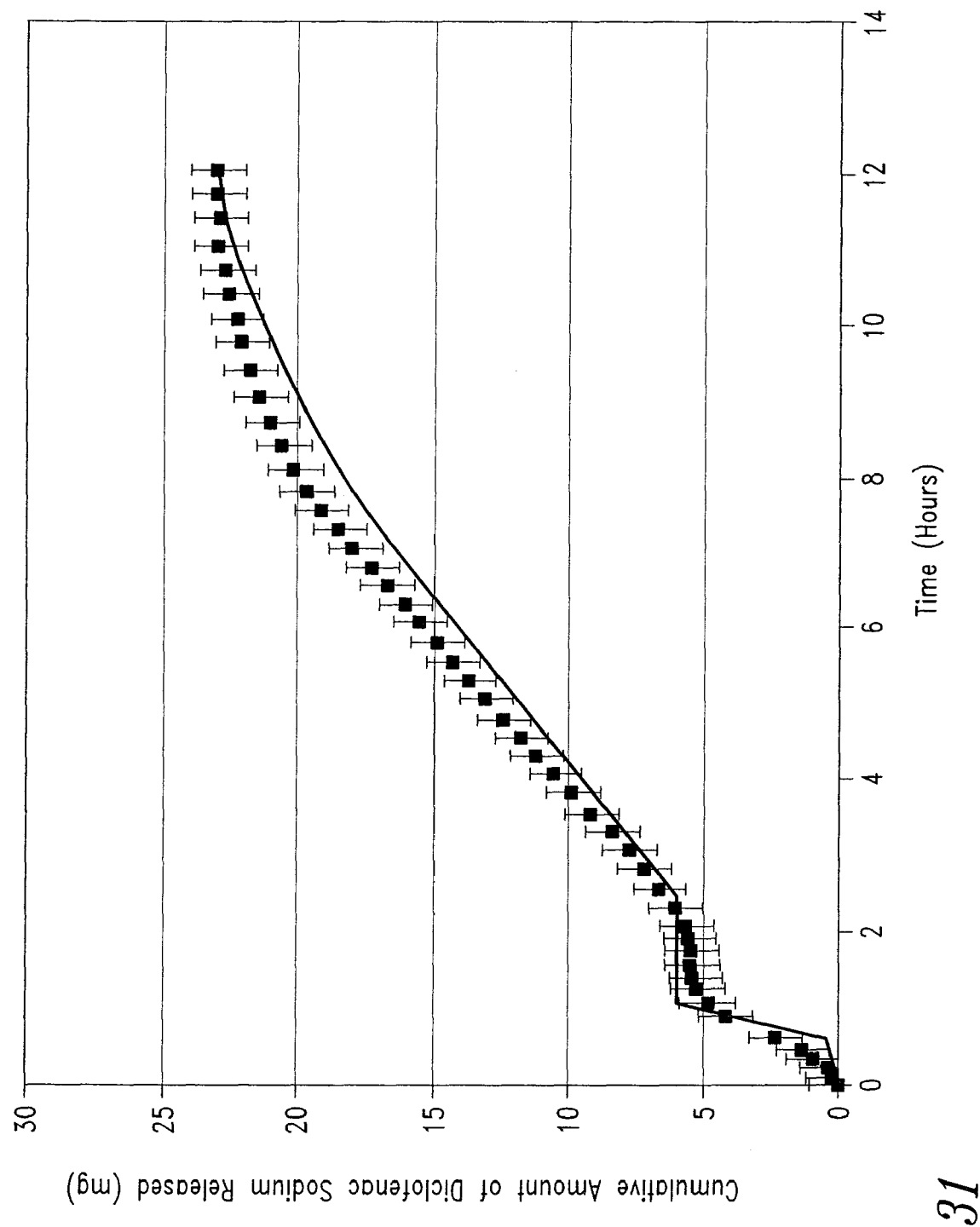
FIG. 31 graphically illustrates both measured and predicted cumulative release for the dosage form of FIG. 27 containing Chlorpheniramine Maleate in accordance with principles of the present invention.
Figure 32:
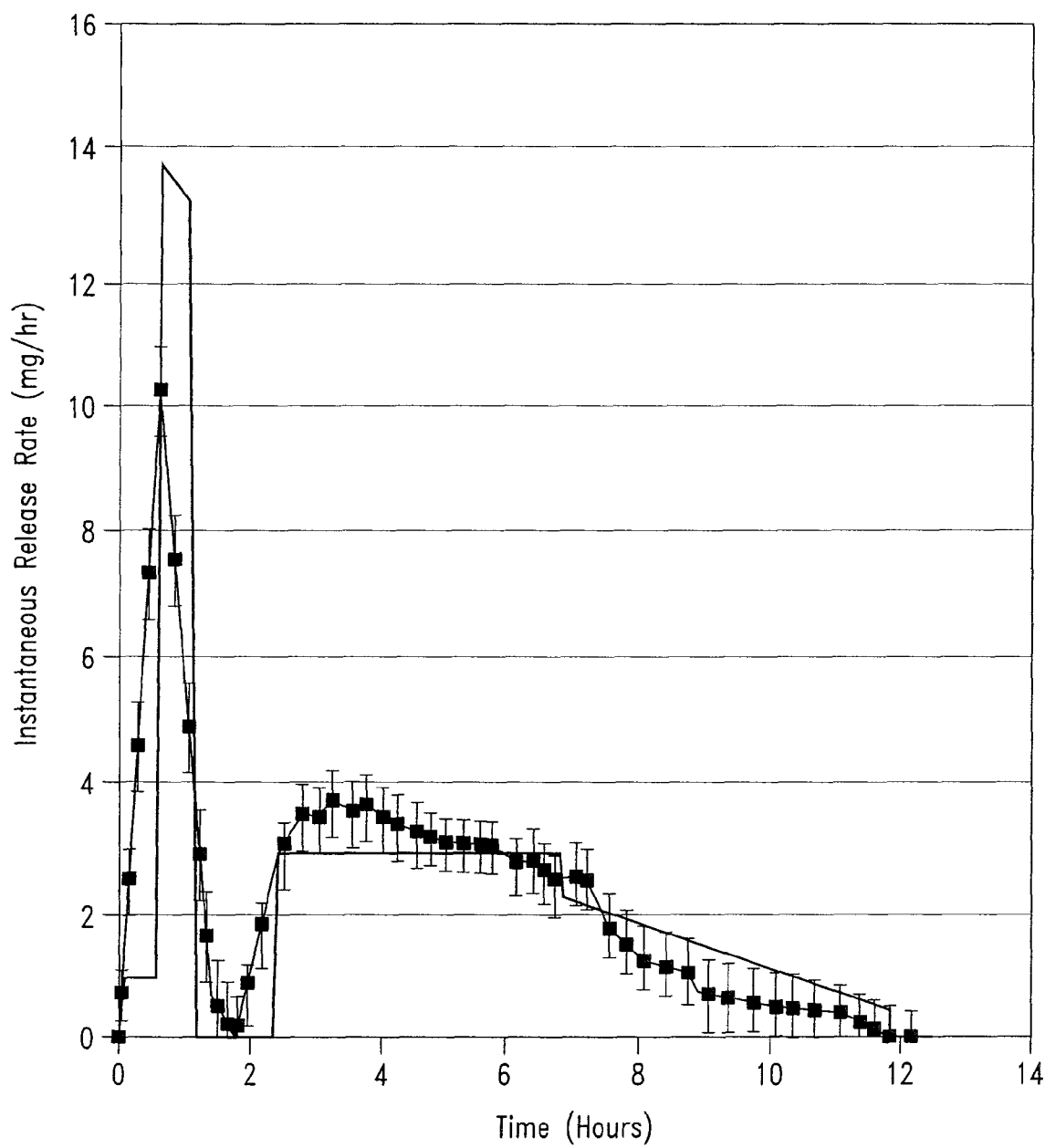
FIG. 32 graphically illustrates both measured and predicted instantaneous release for the dosage form of FIG. 27 containing Diclofenac Sodium in accordance with principles of the present invention.
Figure 33:
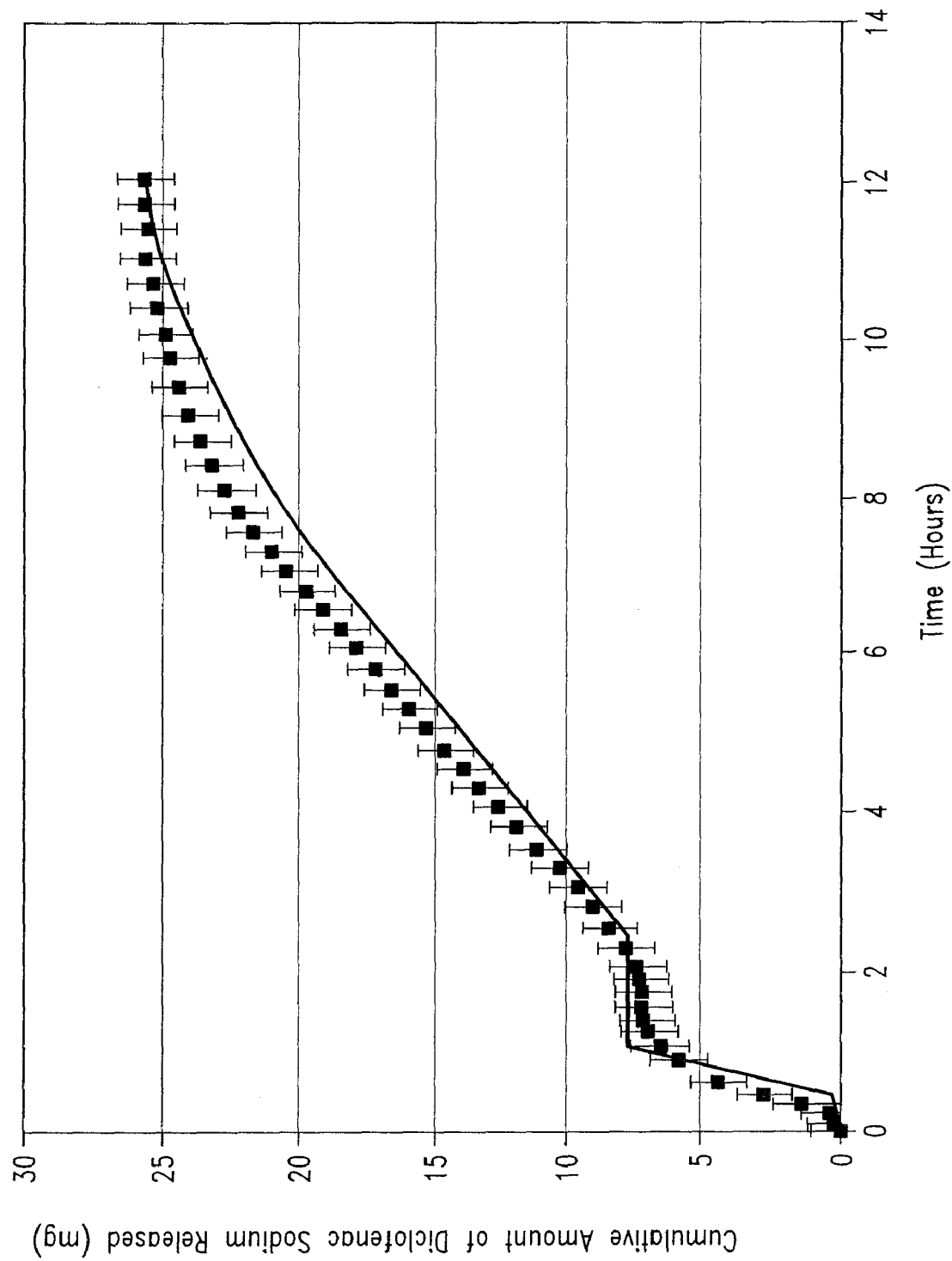
FIG. 33 graphically illustrates both measured and predicted cumulative release for the dosage form of FIG. 27 containing Diclofenac Sodium in accordance with principles of the present invention.

The third difference can be best observed from FIGS. 29 and 31, the cumulative release profiles. The actual release seems to expire before that of the model dosage forms. The actual release curves are shifted somewhat to the left as compared to the model. This may be due to differences in the release rates between conventional tablets and 3DP dosage forms. The parameters used to establish the model system came from Table 2, for conventional tablets. These conventional tablets were pressed together from mixed powder mixtures, and were not printed. The conventional tablets were constructed with approximately the same API concentration as the API sections of the printed samples, they were approximately the same size, and they were tested under the same conditions. The only difference is the fabrication technique. It should be noted, however, that the information acquired from the conventional tablets is a good approximation, and provides a fast and easy alternative to data collection from 3DP dosage forms.

Example 11

Design of Surround-Region so as to Eliminate the "Burst Effect"

This Example describes a dosage form having an outermost region, which may be called a surround-region, which is designed so as to eliminate or substantially reduce the "burst effect." This surround-region may surround all of the rest of the dosage form, with the rest of the dosage form being designed according to any of the designs described herein, which may include either fully-nested or other more complicated designs. As an example of other more complicated designs, the design of Example 10 could be surrounded by a surround-region for this purpose. In Example 1, the "burst effect" was shown to occur during the early part of exposure of a dosage form to water, when the gel region was just becoming established and had not yet reached a quasi-steady state such as would persist during most of the process of erosion/degradation of the dosage form. In Example 1 it was shown that during initial formation of the gel region, the recession rate of the solid/hydration front was unusually rapid. This can be associated with unusually rapid release of API contained in the outermost region of the dosage form. Accordingly, that unusually rapid release can be completely eliminated by manufacturing the surround-region so as to contain no API. The thickness of the surround-region may be chosen so as to delay the start of release of any API until a time when the gel region is well established at or almost at its quasi-steady-state configuration. However, this of course means that a patient would not begin receiving API until a certain period of time after administration of the dosage form, which may or may not be acceptable. Alternatively, a calculated API release during the period of the "burst effect" can be obtained by manufacturing the surround-region with an appropriate concentration so that release during the early period is what is desired, given the occurrence during the early release period of processes which are not typical of the more ordinary part of the release process. A surround-region may also be used with dosage forms of the radial-release end-capped design (Examples 3, 4 and 5), with the understanding that the surround-region only has to surround the central portion where API is contained, and surrounding of the end caps by the surround-region is optional.

Example 12

Description of Manufacturing Techniques

Dosage forms of the present invention were printed using three-dimensional printing using a continuous-jet-with-deflection printhead.

For some of the Examples, both diclofenac sodium dosage forms and chlorpheniramine maleate dosage forms were fabricated. The powder was 70 wt % 53-74 micrometer lactose and 30 wt % 53-74 micrometer HPMC K4M or, in other cases a Lactose:HPMC ratio of 80:20.

For some portions (end caps) of some dosage forms as described elsewhere herein, powder containing pure HPMC was used.

The printing parameters included a layer thickness of 200 micrometers.

The binder solution used for both was 5 wt % L100 in ethanol and the API solutions were respectively 18 wt % diclofenac sodium in methanol and 20 wt % chlorpheniramine maleate in 80:20 ethanol:deionized water.

After completion of three-dimensional printing, printed dosage forms were allowed to dry for two days in a nitrogen glove box and then were pressed in a tablet die of 11 mm inside diameter. After completion of three-dimensional printing and drying, all dosage forms reported here were compressed, although in some situations it might be possible to practice the present invention without compression. Compression was done at a pressure of 15,000 lbf/inch^2 (psi) as described elsewhere herein. Digital calipers measured final heights of dosage forms after compression.

For the data reported in Example 1 and some of the data reported in Example 2, powder was simply compressed in a die without being three-dimensionally printed.

Further details are given below.

Printing Parameters for Dosage Forms Printed for Observation in Glass Slide Assembly (Example 1)

| PRINTING PARAMETER | |
|---|---|
| Powder System | 70 wt % HPMC K4M 30 wt % Lactose Monohydrate |
| Powder Size (μm) | 53-74 |
| Layer Thickness (μm) | 300 |
| Packing Fraction | 0.412 |
| BINDER | |
| Binder Solution Solutes | N/A |
| Binder solution solvent | — |
| Solution density g/cc | — |
| Weight fraction | — |
| Line Spacing (um) | — |
| Nozzle Orifice (um) | — |
| Flow Rate (g/min) | — |
| Modulation Frequency (KHz) | — |
| ACTIVE | Diclofenac Sodium |
| Drug Solution Solutes | 18 wt % diclofenac, 1 wt % PVP, 0.05 wt % fluorescein |
| Drug Solution Solvent | Methanol |
| Solution density g/cc | 0.90 |
| Line Spacing (um) | 120 |
| Nozzle Orifice (um) | 50.4 |
| Flow Rate (g/min) | 0.97 |
| Modulation Frequency (KHz) | 42 |
| SATURATION (% of void space filled per pass) | 0.566 |
| Overall number of passes | 3 |
| Drug Volume Fraction | 0.15 |
| DOSAGE | |
| Total mgs printed per tablet | 101.8 |
| COMPRESSION (yes/no) | Yes |
| Compression Force (psi) | 15000 |
| % Vertical compression | N/A |
| Dosage per unit tablet volume δ mg/cc | 325 |

Printing Parameters for Dosage Forms of Example 10 Containing Diclofenac Sodium

| PRINTING PARAMETER | |
|---|---|
| Powder System | 70 wt % HPMC K4M 30 wt % Lactose Monohydrate |
| Powder Size (μm) | 53-74 |
| Layer Thickness (μm) | 200 |
| Packing Fraction | 0.412 |
| BINDER | |
| Binder Solution Solutes | Eudragit ™ L100 |
| Binder solution solvent | Ethanol |
| Solution density g/cc | 0.82 |
| Weight fraction | 5 wt % L100 |
| Line Spacing (um) | 120 |
| Nozzle Orifice (um) | 50.4 |
| Flow Rate (g/min) | 0.97 |
| Modulation Frequency (KHz) | 42.8 |
| ACTIVE | Diclofenac Sodium |
| Drug Solution Solutes | 18 wt % diclofenac, 1 wt % PVP, 0.05 wt % fluorescein |
| Drug Solution Solvent | Methanol |
| Solution density g/cc | 0.90 |
| Line Spacing (um) | 120 |
| Nozzle Orifice (um) | 50.4 |

-continued

| | |
|---|---|
| Flow Rate (g/min) | 0.92 |
| Modulation Frequency (KHz) | 48 |
| Apparent Saturation | 1.86 |
| DOSAGE | |
| Total mgs printed per tablet | 25.8 |
| COMPRESSION (yes/no) | Yes |
| Compression Force (psi) | 15000 |
| % Vertical compression | 55.0 |
| Dosage per unit tablet volume δ mg/cc | 312 |

Printing Parameters for Dosage Forms of Example 10 Containing Chlorpheniramine Maleate

| PRINTING PARAMETER | |
|---|---|
| Powder System | 70 wt % HPMC K4M 30 wt % Lactose Monohydrate |
| Powder Size (μm) | 53-74 |
| Layer Thickness (μm) | 200 |
| Packing Fraction | 0.412 |
| BINDER | |
| Binder Solution Solutes | Eudragit ™ L100 |
| Binder solution solvent | Ethanol |
| Solution density g/cc | 0.82 |
| Weight fraction | 5 wt % L100 |
| Line Spacing (um) | 120 |
| Nozzle Orifice (um) | 50.4 |
| Flow Rate (g/min) | 0.93 |
| Modulation Frequency (KHz) | 48.4 |
| Binder Saturation | |
| ACTIVE | Chlorpheniramine Maleate |
| Drug Solution Solutes | 20 wt % Chlorpheniramine Maleate |
| Drug Solution Solvent | 80% ethanol 20% D.I. water |
| Solution density g/cc | 1.15 |
| Line Spacing (um) | 120 |
| Nozzle Orifice (um) | 50.4 |
| Flow Rate (g/min) | 0.98 |
| Modulation Frequency (KHz) | 45.7 |
| Apparent Saturation | 1.46 |
| DOSAGE (Total mgs printed per tablet) | 23.0 |
| COMPRESSION (yes/no) | Yes |
| Compression Force (psi) | 15000 |
| % Vertical compression | 55.0 |
| Dosage per unit tablet volume δ mg/cc | 277 |

Printing Parameters for Dosage Forms of Example 2 Containing Constant Uniform Distribution of Diclofenac Sodium

| PRINTING PARAMETER | |
|---|---|
| Powder System | 70 wt % HPMC K4M 30 wt % Lactose Monohydrate |
| Powder Size (μm) | 53-74 |
| Layer Thickness (μm) | 300 |
| Packing Fraction | 0.412 |
| BINDER | N/A |
| Binder Solution Solutes | — |
| Binder solution solvent | — |
| Solution density g/cc | — |
| Weight fraction | — |
| Line Spacing (um) | — |
| Nozzle Orifice (um) | — |
| Flow Rate (g/min) | — |
| Modulation Frequency (KHz) | — |
| ACTIVE | Diclofenac Sodium |
| Drug Solution Solutes | 18 wt % diclofenac, 1 wt % PVP, 0.05 wt % fluorescein |
| Drug Solution Solvent | Methanol |
| Solution density g/cc | 0.90 |
| Line Spacing (um) | 120 |
| Nozzle Orifice (um) | 50.4 |
| Flow Rate (g/min) | 0.97 |
| Modulation Frequency (KHz) | 42 |
| SATURATION (% of void space filled per pass) | 0.56 |
| Overall number of passes | 1 |
| Polymer Volume Fraction | N/A |
| DOSAGE | |
| Total mgs printed per tablet | 44.1 |
| COMPRESSION (yes/no) | Yes |
| Compression Force (psi) | 15000 |
| % Vertical compression | 50.0 |
| Dosage per unit tablet volume δ mg/cc | 107 |

Printing Parameters for 80% Lactose 20% HPMC Radial-Release Non-Uniform Distribution Dosage Forms

| PRINTING PARAMETER | |
|---|---|
| Powder System | 80 wt % HPMC K4M 20 wt % Lactose Monohydrate |
| Powder Size (μm) | 53-74 |
| Layer Thickness (μm) | 300 |
| Packing Fraction | 0.425 |
| BINDER | N/A |
| Binder Solution Solutes | — |
| Binder solution solvent | — |
| Solution density g/cc | — |
| Weight fraction | — |
| Line Spacing (um) | — |
| Nozzle Orifice (um) | — |
| Flow Rate (g/min) | — |
| Modulation Frequency (KHz) | — |
| ACTIVE | Diclofenac Sodium |
| Drug Solution Solutes | 18 wt % diclofenac, 1 wt % PVP, 0.05 wt % fluorescein |

-continued

| PRINTING PARAMETER | | | | | |
|---|---|---|---|---|---|
| Drug Solution Solvent | Methanol | | | | |
| Solution density g/cc | 0.90 | | | | |
| Line Spacing (um) | 120 | | | | |
| Nozzle Orifice (um) | 50.4 | | | | |
| Flow Rate (g/min) | 0.98 | | | | |
| Modulation Frequency (KHz) | 45.7 | | | | |
| Fast axis speed cm/sec | 150 | | | | |
| SATURATION (% of void space filled per pass) | 0.584 | | | | |
| | Region 1 | Region 2 | Region 3 | Region 4 | Region 5 |
| Overall number of passes | 1 | 2 | 3 | 4 | 5 |
| DOSAGE per zone in mgs | 22.34 | 14.72 | 11.08 | 9.09 | 44.58 |
| Total mgs printed per tablet | | | 101.8 | | |
| COMPRESSION (yes/no) | | | Yes | | |
| Compression Force (psi) | | | 15000 | | |
| % Vertical compression | | | 50.0 | | |
| Dosage per unit tablet volume δ mg/cc | 108 | 217 | 325 | 434 | 542 |

Printing Parameters for 70% Lactose 30% HPMC Radial-Release Non-Uniform Distribution Dosage Forms 25

| PRINTING PARAMETER | | | | | |
|---|---|---|---|---|---|
| Powder System | 70 wt % HPMC K4M 30 wt % Lactose Monohydrate | | | | |
| Powder Size (μm) | 53-74 | | | | |
| Layer Thickness (μm) | 300 | | | | |
| Packing Fraction | 0.412 | | | | |
| BINDER | N/A | | | | |
| Binder Solution Solutes | — | | | | |
| Binder solution solvent | — | | | | |
| Solution density g/cc | — | | | | |
| Weight fraction | — | | | | |
| Line Spacing (um) | — | | | | |
| Nozzle Orifice (um) | — | | | | |
| Flow Rate (g/min) | — | | | | |
| Modulation Frequency (KHz) | — | | | | |
| ACTIVE | Diclofenac Sodium | | | | |
| Drug Solution Solutes | 18 wt % diclofenac, 1 wt % PVP, 0.05 wt % fluorescein | | | | |
| Drug Solution Solvent | Methanol | | | | |
| Solution density g/cc | 0.90 | | | | |
| Line Spacing (um) | 120 | | | | |
| Nozzle Orifice (um) | 50.4 | | | | |
| Flow Rate (g/min) | 0.97 | | | | |
| Modulation Frequency (KHz) | 42 | | | | |
| Fast axis speed cm/sec | 150 | | | | |
| SATURATION (% of void space filled per pass) | 0.566 | | | | |
| | Region 1 | Region 2 | Region 3 | Region 4 | Region 5 |
| Overall number of passes | 1 | 2 | 3 | 4 | 5 |
| DOSAGE per zone in mgs | 22.1 | 14.56 | 10.96 | 8.99 | 44.10 |
| Total mgs printed per tablet | | | 100.7 | | |
| COMPRESSION (yes/no) | | | Yes | | |
| Compression Force (psi) | | | 15000 | | |
| % Vertical compression | | | 50.0 | | |
| Dosage per unit tablet volume δ mg/cc | 107 | 215 | 322 | 429 | 536 |

Printing Parameters for 70% Lactose 30% HPMC 3D-Release Non-Uniform Distribution Dosage Forms

| PRINTING PARAMETER | | | | | |
|---|---|---|---|---|---|
| Powder System | 70 wt % HPMC K4M 30 wt % Lactose Monohydrate | | | | |
| Powder Size (μm) | 53-74 | | | | |
| Layer Thickness (μm) | 305 | | | | |
| Packing Fraction | 0.412 | | | | |
| BINDER | N/A | | | | |
| Binder Solution Solutes | — | | | | |
| Binder solution solvent | — | | | | |
| Solution density g/cc | — | | | | |
| Weight fraction | — | | | | |
| Line Spacing (um) | — | | | | |
| Nozzle Orifice (um) | — | | | | |
| Flow Rate (g/min) | — | | | | |
| Modulation Frequency (KHz) | — | | | | |
| ACTIVE | Diclofenac Sodium | | | | |
| Drug Solution Solutes | 18 wt % diclofenac, 1 wt % PVP | | | | |
| Drug Solution Solvent | Methanol | | | | |
| Solution density g/cc | 0.90 | | | | |
| Line Spacing (um) | 120 | | | | |
| Nozzle Orifice (um) | 50.4 | | | | |
| Flow Rate (g/min) | 0.96 | | | | |
| Modulation Frequency (KHz) | 45.6 | | | | |
| Fast axis speed cm/sec | 150 | | | | |
| SATURATION (% of void space filled per pass) | 0.573 | | | | |
| | Region 1 | Region 2 | Region 3 | Region 4 | Region 5 |
| Overall number of passes | 1 | 2 | 3 | 4 | 5 |
| DOSAGE per zone in mgs | 28.19 | 13.34 | 6.99 | 5.75 | 17.38 |
| Total mgs printed per tablet | | | 71.65 | | |
| COMPRESSION (yes/no) | | | Yes | | |
| Compression Force (psi) | | | 15000 | | |
| % Vertical compression | | | 47.7 | | |
| Dosage per unit tablet volume δ mg/cc | 110 | 220 | 330 | 440 | 550 |

Further details are given in Fabrication of Complex Oral Drug Delivery Forms by Three-Dimensional Printing, by Wendy E. Katstra, PhD thesis at Massachusetts Institute of Technology, 2001, herein incorporated in its entirety by reference.

Further Considerations and Summary and Advantages

It can be appreciated that virtually any spatial distribution of API concentration can be deposited into the dosage form according to the present invention. Any such API distribution could be modeled and designed and manufactured using the techniques already described. Active Pharmaceutical Ingredient should be understood to refer to at least one Active Pharmaceutical Ingredient (or similar additive), not just one. Different API could be deposited into different places within the dosage form, or could be deposited into the same regions as each other. The release profile for one API could be different from the release profile for another API. Within a single dosage form, and occupying the same dosage form, the regions defining the concentration distribution of one API could be defined differently from the regions defining the concentration distribution for another API. Saturation parameters for 3DP could be different at different places within the dosage form and could be different for one printed substance as compared to another substance printed with a different binder liquid.

While the experiments conducted have pertained to oral dosage forms, it should be understood that the same principles apply to implantable drug delivery devices. The time scale of release for implantables will likely be longer than that for oral dosage forms, and the materials may be different (such as biodegradable polymers). However, the dosage form designs and methods of design would be similar to those already described.

It should also be understood that while API release has been described in terms of erosion and has described diffusion as being a somewhat contrasting situation, real API release may involve a combination of both processes being active simultaneously. The main features of the release phenomenon that allow the design methodology to work are that the surface or, more generally, the release-determining feature of the dosage form recedes as a function of time and that the instantaneous release rate is proportional to a concentration of the API present at the surface or, more generally, the release-determining feature. While these characteristics are most associated with erosive release, they may also be found, at least to a sufficient degree of accuracy, in dosage forms that are not purely erosive.

All patents and patent applications and publications cited above are incorporated by reference in their entirety. Furthermore, identify co-filed (same day applications) (if any) and incorporate them by reference also. The above description of illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. Aspects of the invention can be modified, if necessary, to employ the process, apparatuses and concepts of the various patents and applications described above to provide yet further embodiments of the invention. These and other changes can be made to the invention in light of the above detailed description. In general, in the following claims, the terms used should not be construed to limit the invention to the specific embodiments disclosed in the specification and the claims, but should be construed to include all dosage forms that operate under the claims. Accordingly, the invention is not limited by the disclosure, but instead the scope of the invention is to be determined entirely by the following claims.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A dosage form comprising:
   a first end cap;
   a second end cap; and
   a three-dimensionally printed radially-nested region in contact with and axially extending between the first end cap and the second end cap, the radially-nested region comprising:
   an innermost region comprising a first regional concentration of at least one Active Pharmaceutical Ingredient; and
   plural three-dimensionally printed non-innermost regions in radially-nested arrangement about the innermost region and comprising:
   a) one or more radially-nested internal regions each comprising a respective regional concentration of at least one Active Pharmaceutical Ingredient, wherein an internal region radially surrounds and is in radial contact with the innermost region, and any other internal region present radially surrounds another internal region located to the interior thereof; and
   b) an outermost region radially surrounding an internal region and comprising a respective regional concentration of at least one Active Pharmaceutical Ingredient,
   wherein the internal and outermost regions are in radially-nested arrangement, the regional concentration of Active Pharmaceutical Ingredient in a region is different from the regional concentration of Active Pharmaceutical Ingredient in another region adjacent to it, the regional concentration of Active Pharmaceutical Ingredient in an internal region is non-zero, the regional concentration of Active Pharmaceutical Ingredient in plural regions is non-zero, and the respective regional concentrations are selected so that the at least one Active Pharmaceutical Ingredient is released according to an approximately zero-order release profile after exposure of the dosage form to an aqueous environment of use.

2. A dosage form comprising:
   a first end cap;
   a second end cap; and
   a three-dimensionally printed radially-nested region in contact with and axially extending vertically between the first end cap and the second end cap, the radially-nested region comprising:
   an innermost region comprising a first regional concentration of at least one Active Pharmaceutical Ingredient; and
   plural three-dimensionally printed non-innermost regions in radially-nested arrangement about the innermost region and comprising:
   a) one or more radially-nested internal regions each comprising a respective regional concentration of at least one Active Pharmaceutical Ingredient, wherein an internal region radially surrounds and is in radial contact with the innermost region, and any other internal region present radially surrounds another internal region located to the interior thereof; and
   b) an outermost region radially surrounding an internal region and comprising a respective regional concentration of at least one Active Pharmaceutical Ingredient,
   wherein the internal and outermost regions are in radially-nested arrangement, the regional concentration of Active Pharmaceutical Ingredient in a region is different from the regional concentration of Active Pharmaceutical Ingredient in another region adjacent to it; the regional concentration of Active Pharmaceutical Ingredient in an internal region is non-zero; the regional concentration of Active Pharmaceutical Ingredient in plural regions is non-zero; the respective regional concentrations are selected so that the at least one Active Pharmaceutical Ingredient is released according to an approximately zero-order release profile after exposure of the dosage form to an aqueous environment of use; the end caps do not release API; and the end caps are three-dimensionally printed.

3. The dosage form of claim 1, wherein each additional region except the innermost region is annular and has a respective radial distance from a central axis of the dosage form, and the respective regional concentrations are approximately proportional to the inverse of the respective radial distance of the region from the axis.

4. The dosage form of claim 1, wherein each additional region except the innermost region is annular and has a respective radial distance from a central axis of the dosage form, and the respective regional concentrations are approximately proportional to the inverse of the square of the respective radial distance of the region from the axis.

5. The dosage form of claim 1, wherein the innermost region has the shape of a rectangular prism and each region except the innermost region has a shape of a rectangular shell.

6. The dosage form of claim 1, wherein the innermost region has substantially no content of at least one Active Pharmaceutical Ingredient.

7. The dosage form of claim 1 wherein the innermost region has substantially no content of any Active Pharmaceutical Ingredient.

8. The dosage form of claim 1 wherein the end caps comprise hydroxypropyl methylcellulose and the regions comprise hydroxypropyl methylcellulose and an adjuvant.

9. The dosage form of claim 1, wherein the dosage form has a shape selected from the group consisting of: cylindrical of any aspect ratio with flat ends; cylindrical of any aspect ratio with rounded ends; rectangular prismatic; substantially spherical; and substantially ellipsoidal.

10. The dosage form of claim 1, wherein the dosage form has a void fraction less than 5%.

11. The dosage form of claim 1 further comprising a surround-region radially surrounding the most exterior additional region and having a wall thickness, whereby the surround-region controls the release of drug from the dosage form during an initial period after exposure of the dosage form to a bodily fluid.

12. The dosage form of claim 11, wherein the surround-region does not comprise any Active Pharmaceutical Ingredient.

13. The dosage form of claim 11, wherein the surround-region has a concentration of a surround-region Active Pharmaceutical Ingredient that is selected in accordance with the behavior of the dosage form during an initial period of exposure of the dosage form to a liquid.

14. The dosage form of claim 1, wherein the dosage form is manufactured by three-dimensional printing.

* * * * *